United States Patent
Sanders et al.

(10) Patent No.: US 9,700,424 B2
(45) Date of Patent: Jul. 11, 2017

(54) JOINT ARTHROPLASTY SYSTEMS, METHODS, AND COMPONENTS

(71) Applicant: Foot Innovations, LLC, Tampa, FL (US)

(72) Inventors: Roy W Sanders, Tampa, FL (US); Sergio Gutierrez, Tampa, FL (US)

(73) Assignee: Foot Innovations, LLC, Tampa, FL (US)

( * ) Notice: Subject to any disclaimer, the term of this patent is extended or adjusted under 35 U.S.C. 154(b) by 437 days.

(21) Appl. No.: 14/219,676

(22) Filed: Mar. 19, 2014

(65) Prior Publication Data
US 2014/0207244 A1    Jul. 24, 2014

Related U.S. Application Data

(63) Continuation of application No. 13/670,664, filed on Nov. 7, 2012, now abandoned.

(51) Int. Cl.
*A61F 2/42*    (2006.01)
*A61F 2/30*    (2006.01)

(52) U.S. Cl.
CPC .......... *A61F 2/4225* (2013.01); *A61F 2/4202* (2013.01); *A61F 2002/30387* (2013.01); *A61F 2002/30578* (2013.01); *A61F 2002/30878* (2013.01); *A61F 2002/30884* (2013.01); *A61F 2002/4207* (2013.01); *A61F 2002/4217* (2013.01)

(58) Field of Classification Search
CPC ....................................................... A61F 2/42
USPC .......... 623/20.18, 22.38, 22.11, 21.11, 21.18
See application file for complete search history.

(56) References Cited

U.S. PATENT DOCUMENTS

| | | |
|---|---|---|
| 5,484,439 A | 1/1996 | Olson et al. |
| 5,800,551 A | 9/1998 | Williamson et al. |
| 6,464,728 B1 | 10/2002 | Murray |
| 6,508,840 B1 | 1/2003 | Rockwood, Jr. et al. |
| 6,514,287 B2 * | 2/2003 | Ondrla ................. A61F 2/4081 623/19.13 |
| 6,679,916 B1 | 1/2004 | Frankle et al. |
| 6,790,234 B1 | 9/2004 | Frankle |
| 6,875,234 B2 | 4/2005 | Lipman et al. |
| 6,916,323 B2 | 7/2005 | Kitchens |
| 6,942,699 B2 | 9/2005 | Stone et al. |
| 7,044,973 B2 | 5/2006 | Rockwood, Jr. et al. |
| 7,431,736 B2 | 10/2008 | Maroney et al. |

(Continued)

OTHER PUBLICATIONS

USPTO, Office Action for U.S. Appl. No. 12/732,509, mailed on May 23, 2012, p. 1-13.

(Continued)

*Primary Examiner* — Christopher D Prone
*Assistant Examiner* — Christine Nelson
(74) *Attorney, Agent, or Firm* — Shabbi Khan; Foley & Lardner LLP

(57) ABSTRACT

Surgical implant systems, methods, and components are described herein. More particularly, the disclosure relates to joint arthroplasty systems, methods, and components. Particular embodiments described herein can be used to modify the subtalar joint (e.g., posterior facet of the subtalar joint), calcaneocuboid, talonavicular, and any other suitable joint. An exemplary implant system comprises a first implant component, a second implant component, and an insert.

13 Claims, 48 Drawing Sheets

(56) References Cited

U.S. PATENT DOCUMENTS

| | | |
|---|---|---|
| 7,534,246 B2 | 5/2009 | Reiley et al. |
| 7,604,665 B2 | 10/2009 | Iannotti et al. |
| 7,699,853 B2 | 4/2010 | Durand-Allen et al. |
| 7,780,670 B2 | 8/2010 | Bonutti |
| 7,854,768 B2 | 12/2010 | Wiley et al. |
| 7,931,680 B2 | 4/2011 | Myerson et al. |
| 2001/0047210 A1 | 11/2001 | Wolf |
| 2002/0016634 A1 | 2/2002 | Maroney et al. |
| 2003/0100952 A1 | 5/2003 | Rockwood, Jr. et al. |
| 2004/0122520 A1 | 6/2004 | Lipman et al. |
| 2004/0210317 A1 | 10/2004 | Maroney et al. |
| 2005/0107796 A1 | 5/2005 | Gerlach et al. |
| 2005/0245808 A1 | 11/2005 | Carson |
| 2006/0142870 A1* | 6/2006 | Robinson ............. A61B 17/14 623/21.18 |
| 2007/0027547 A1 | 2/2007 | Rydell et al. |
| 2007/0260321 A1 | 11/2007 | Stchur |
| 2008/0200989 A1 | 8/2008 | Cachia |
| 2008/0208348 A1 | 8/2008 | Fitz |
| 2008/0269908 A1 | 10/2008 | Warburton |
| 2009/0062923 A1 | 3/2009 | Swanson |
| 2009/0125113 A1 | 5/2009 | Guederian et al. |
| 2010/0016975 A1 | 1/2010 | Iannotti et al. |
| 2010/0130978 A1 | 5/2010 | Orbay et al. |
| 2010/0137865 A1 | 6/2010 | Frankle et al. |
| 2010/0137925 A1 | 6/2010 | Durand-Allen et al. |
| 2010/0217399 A1 | 8/2010 | Groh |
| 2010/0222886 A1 | 9/2010 | Wiley et al. |
| 2010/0241235 A1 | 9/2010 | Basamania et al. |
| 2010/0280625 A1 | 11/2010 | Sanders et al. |
| 2011/0106266 A1 | 5/2011 | Schwyzer et al. |
| 2011/0118846 A1* | 5/2011 | Katrana ............. A61F 2/4014 623/19.13 |
| 2012/0253467 A1 | 10/2012 | Frankle |

OTHER PUBLICATIONS

USPTO, Office Action for U.S. Appl. No. 12/732,509, mailed on Nov. 15, 2012, p. 1-12.

USPTO, Office Action for U.S. Appl. No. 12/410,367, mailed on Jun. 19, 2012, p. 1-21.

* cited by examiner

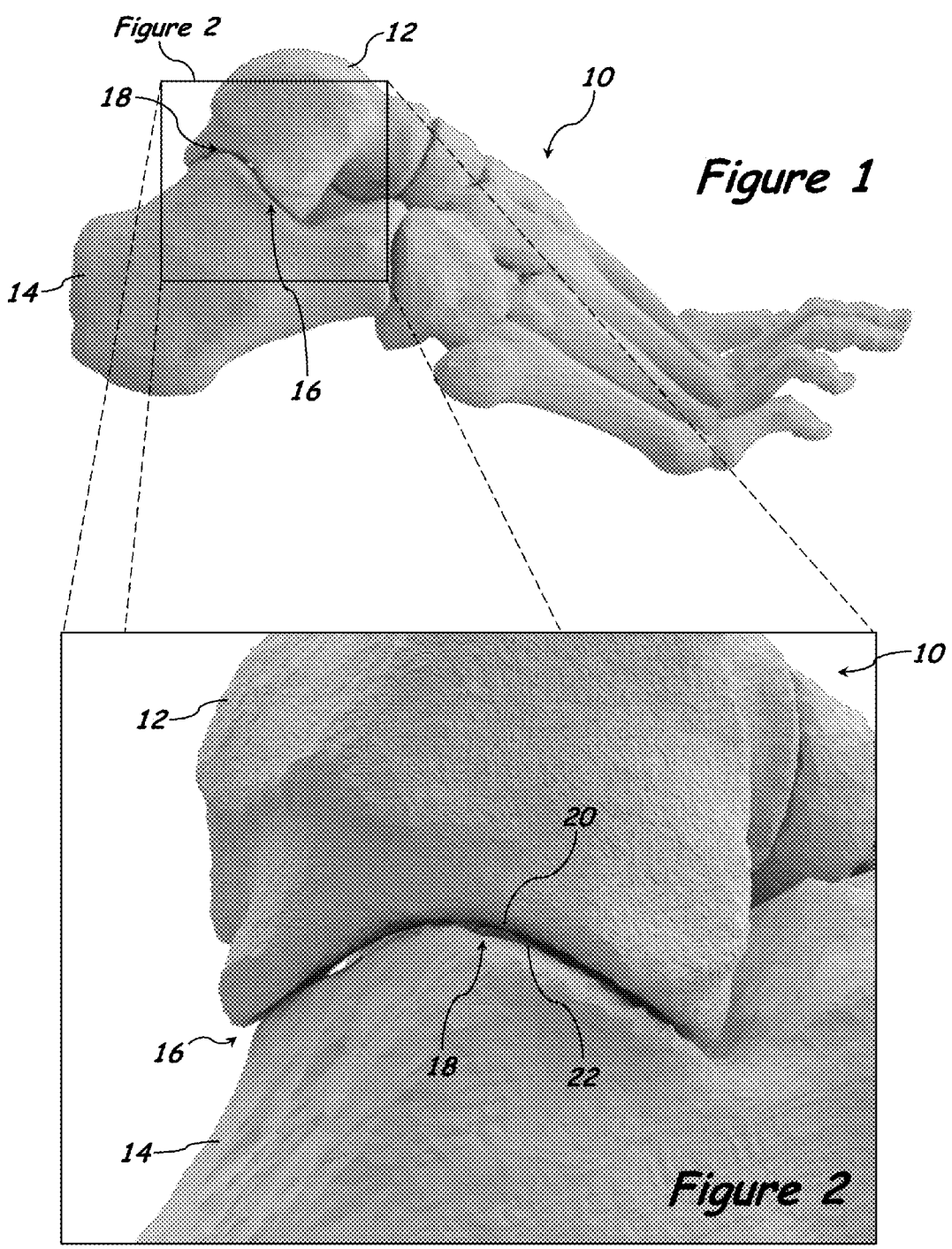

Figure 15
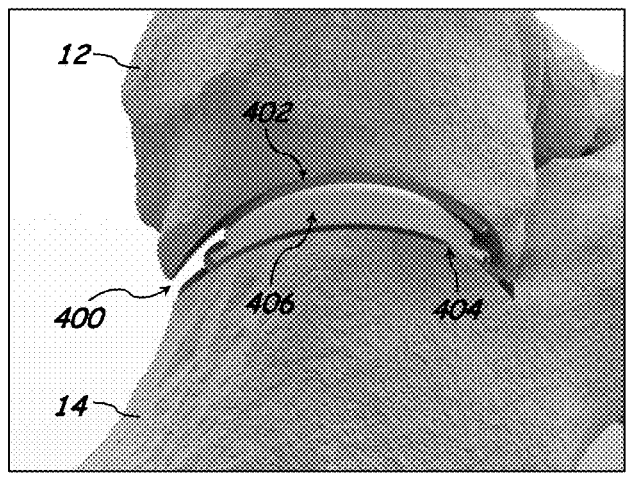
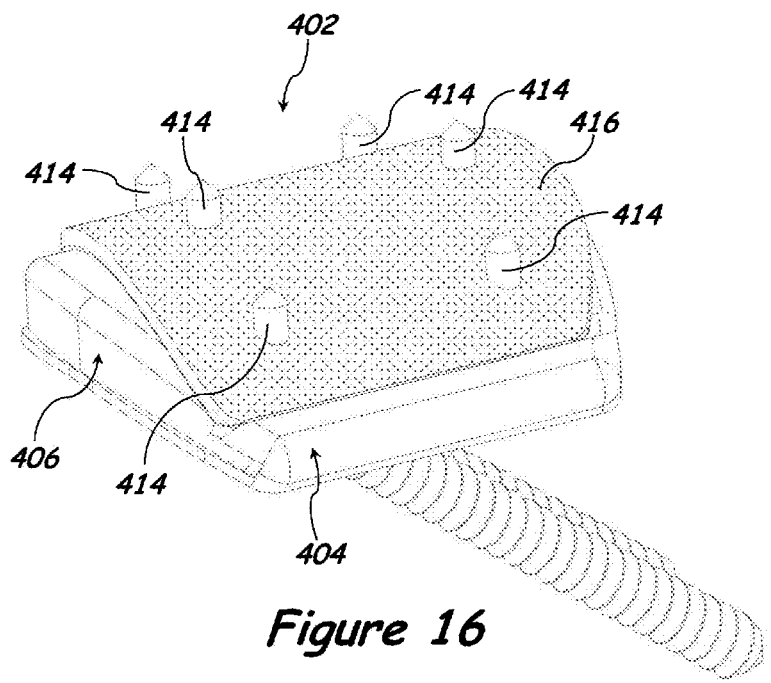
Figure 16

Figure 30
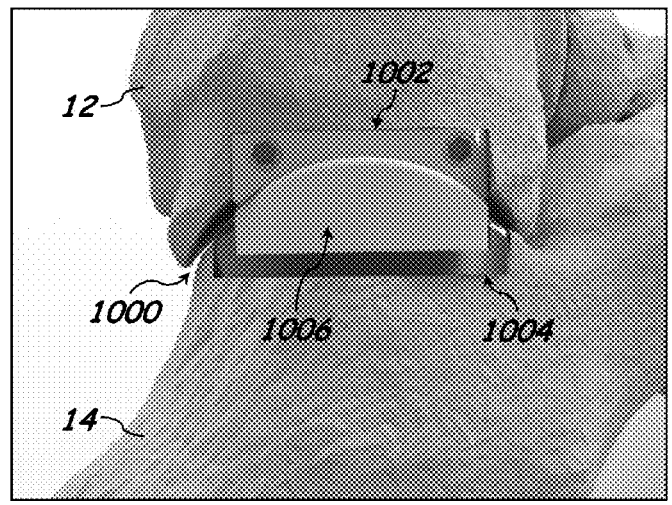
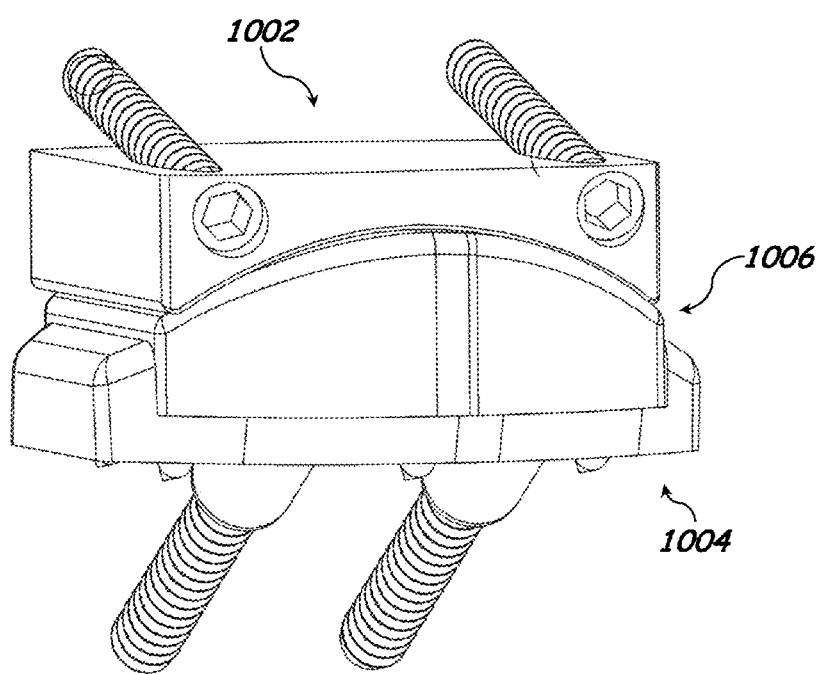
Figure 31

Figure 42
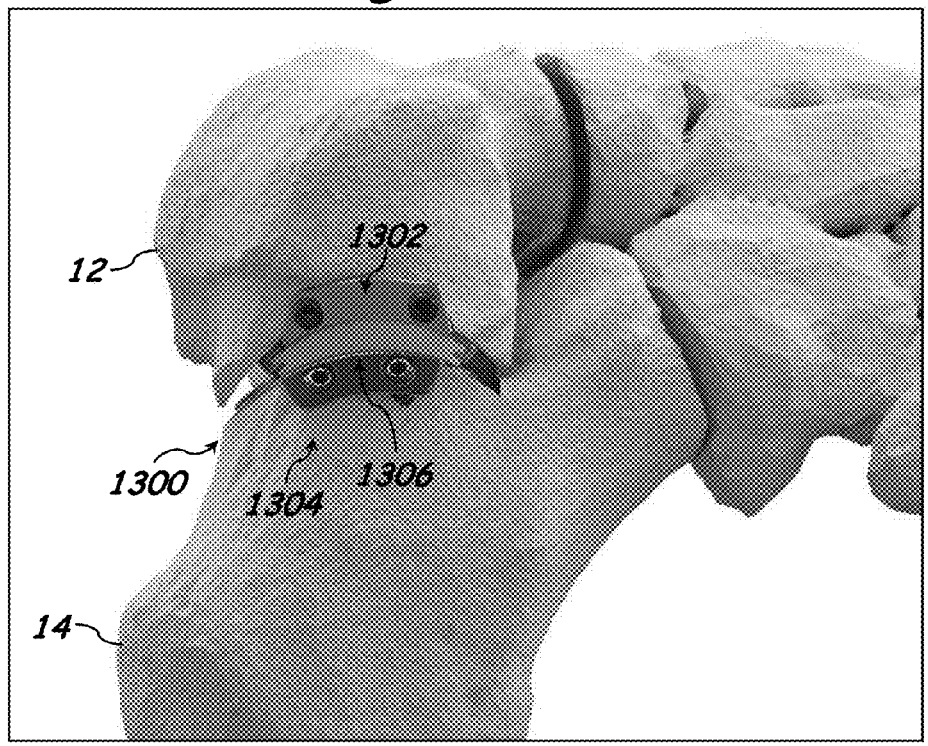
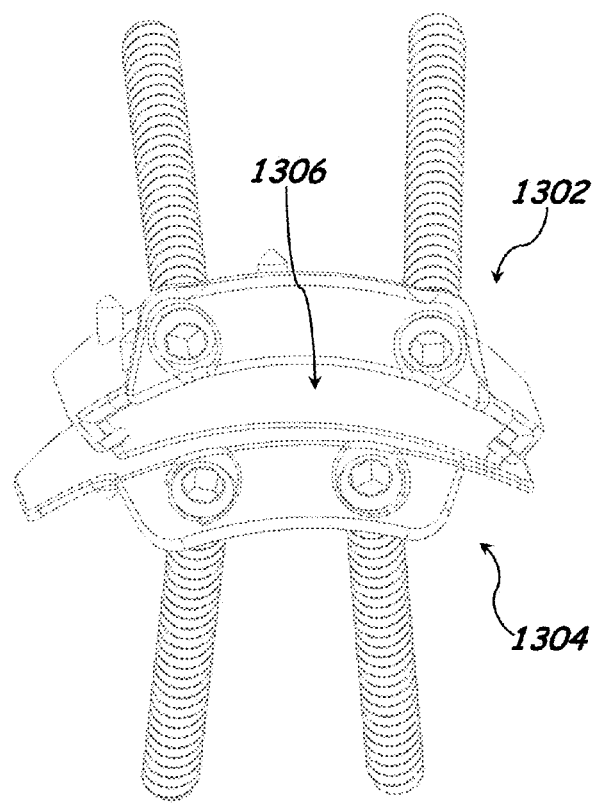
Figure 43

JOINT ARTHROPLASTY SYSTEMS, METHODS, AND COMPONENTS

RELATED APPLICATION DATA

This application is a continuation of U.S. application Ser. No. 13/670,664, filed Nov. 7, 2012, hereby incorporated by reference.

FIELD

The disclosure relates generally to surgical implant systems, methods, and components. More particularly, the disclosure relates to joint arthroplasty systems, methods, and components. Particular embodiments described herein can be used to modify the subtalar joint (e.g., posterior facet of the subtalar joint), calcaneocuboid, talonavicular, and any other suitable joint.

BACKGROUND

The subtalar joint is a joint in the foot formed between the talus and calcaneus and it serves several important roles in human gait. For example, the subtalar joint allows for inversion and eversion of the rear portion of the foot about the lengthwise axis of the foot and abduction and adduction relative to the vertical axis of the tibia. In addition, the subtalar joint allows both pronation and supination to occur and serves to translate rotation of the foot to the tibia and vice versa. The subtalar joint is composed of three articulating facets between the talus and the calcaneus: the anterior, middle, and posterior facets. The anterior and middle facets produce a gliding motion whereas the posterior facet produces a complex triaxial movement due to its saddle shape.

Commonly, inflammatory arthritis, such as rheumatoid arthritis, affects the subtalar joint and requires treatment. Rheumatoid arthritis is known to destroy the subtalar joint through synovitis and, in some cases, directly damages the cartilage in the joint or the tendons around the ankle. In addition to inflammatory arthritis, other afflictions can also affect the subtalar joint, such as eccentric forces that act on the subtalar joint and erode the joint causing pain and discomfort.

Various forms of treatment can be used to treat the afflictions that affect the subtalar joint. For example, various non-operative treatments, such as activity modification, weight-loss, prescription shoes, and/or medication can be used. Alternatively, when non-operative treatments are not successful at providing adequate treatment, operative treatments can be used, such as arthrodesis—the fusing of the talus to the calcaneus. Arthrodesis is generally accomplished by removing any remnants of cartilage from the subtalar joint and placing screws and/or bone grafts across the subtalar joint. This treatment, however, presents several disadvantages. For example, it permanently fixes the talus to the calcaneus, eliminating movement between these bones, and sometimes results in pain and discomfort requiring the performance of subsequent procedures to address these issues.

Therefore, a need exists for improved surgical implant systems, methods, and components for use in joint arthroplasty.

SUMMARY

Various exemplary implant systems, methods, and components are described herein.

A first exemplary implant system for use in a joint arthroplasty comprises a first implant component, a second implant component, and an insert. The first implant component has a first implant proximal end, a first implant distal end, and a first implant body. The first implant body defines a substantially flat first implant surface, a substantially concave first articulating surface opposably facing the first implant surface, a first implant protuberance, and a passageway. The first implant protuberance extends outward and away from the first implant surface and toward the first implant distal end from a first implant protuberance first end to a first implant protuberance second end. The passageway extends from a first opening defined on the first implant proximal end to a second opening defined on the first implant protuberance second end. The second implant component has a second implant proximal end, a second implant distal end, and a second implant body. The second implant body defines a substantially flat second implant surface, a recess that extends into the second implant body from a side opposably facing the second implant surface to a recess base, a second implant protuberance, and a passageway. The second implant protuberance extends outward and away from the second implant surface and toward the second implant distal end from a second implant protuberance first end to a second implant protuberance second end. The passageway extends from a first opening defined on the recess base to a second opening defined on the second implant protuberance second end. The insert is adapted to be releasably attached to the second implant component and has an insert articulating surface that is substantially convex and adapted to articulate with the first articulating surface.

A second exemplary implant system for use in a joint arthroplasty comprises a first implant component, a second implant component, and an insert. The first implant component has a first implant proximal end, a first implant distal end, and a first implant body. The first implant body defines a substantially flat first implant surface, a substantially concave first articulating surface opposably facing the first implant surface, a first implant protuberance, and a passageway. The first implant protuberance extends outward and away from the first implant surface and toward the first implant distal end from a first implant protuberance first end to a first implant protuberance second end. The passageway extends from a first opening defined on the first implant proximal end to a second opening defined on the first implant protuberance second end. The second implant component has a second implant proximal end, a second implant distal end, and a second implant body. The second implant body defines a substantially flat second implant surface, a recess, a second implant protuberance, and a passageway. The recess extends into the second implant body from a side opposably facing the second implant surface to a recess base and from the second implant proximal end toward the second implant distal end. The second implant protuberance extends outward and away from the second implant surface and toward the second implant distal end from a second implant protuberance first end to a second implant protuberance second end. The passageway extends from a first opening defined on the recess base to a second opening defined on the second implant protuberance second end. The recess has a recess first portion that extends from the recess base and away from the second implant surface and a recess second portion that extends from the recess first portion and away from the second implant surface. The insert is adapted to be releasably attached to the second implant component and has an insert articulating surface that is substantially convex and adapted to articulate with the first articulating surface.

A third exemplary implant system for use in a joint arthroplasty comprises a first implant component, a second implant component, and an insert. The first implant component has a first implant proximal end, a first implant distal end, and a first implant body. The first implant body defines a substantially flat first implant surface, a substantially concave first articulating surface opposably facing the first implant surface, a first implant protuberance, and a passageway. The first implant protuberance extends outward and away from the first implant surface and toward the first implant distal end from a first implant protuberance first end to a first implant protuberance second end. The passageway extends from a first opening defined on the first implant proximal end to a second opening defined on the first implant protuberance second end. The second implant component has a second implant proximal end, a second implant distal end, and a second implant body. The second implant body defines a substantially flat second implant surface, a recess, a second implant protuberance, and a passageway. The recess extends into the second implant body from a side opposably facing the second implant surface to a recess base and from the second implant proximal end toward the second implant distal end. The second implant protuberance extends outward and away from the second implant surface and toward the second implant distal end from a second implant protuberance first end to a second implant protuberance second end. The passageway extends from a first opening defined on the recess base to a second opening defined on the second implant protuberance second end. The recess has a recess first portion that extends from the recess base and away from the second implant surface and a recess second portion that extends from the recess first portion and away from the second implant surface. The insert is adapted to be releasably attached to the second implant component and has an insert articulating surface that is substantially convex and adapted to articulate with the first articulating surface. The recess first portion has a recess first portion width along the second implant proximal end and the recess second portion has a recess second portion width along the second implant proximal end. The recess first portion width is different than the recess second portion width.

Additional understanding of the exemplary surgical implant systems, methods, and components can be obtained by review of the detailed description, below, and the appended drawings.

BRIEF DESCRIPTION OF THE FIGURES

FIG. 1 is a lateral view of an exemplary human foot highlighting the subtalar joint.

FIG. 2 is a magnified view of the area indicated in FIG. 1.

FIG. 15 is a perspective view of a fourth exemplary implant system disposed in the subtalar joint of a human foot.

FIG. 16 is a perspective view of the fourth exemplary implant system illustrated in FIG. 15, free of the subtalar joint.

FIG. 30 is a perspective view of an eighth exemplary implant system disposed in the subtalar joint of a human foot.

FIG. 31 is a perspective view of the eighth exemplary implant system illustrated in FIG. 30, free of the subtalar joint.

FIG. 42 is a perspective view of an eleventh exemplary implant system disposed in the subtalar joint of a human foot.

FIG. 43 is a perspective view of the eleventh exemplary implant system illustrated in FIG. 42, free of the subtalar joint.

DETAILED DESCRIPTION

Figure 3:
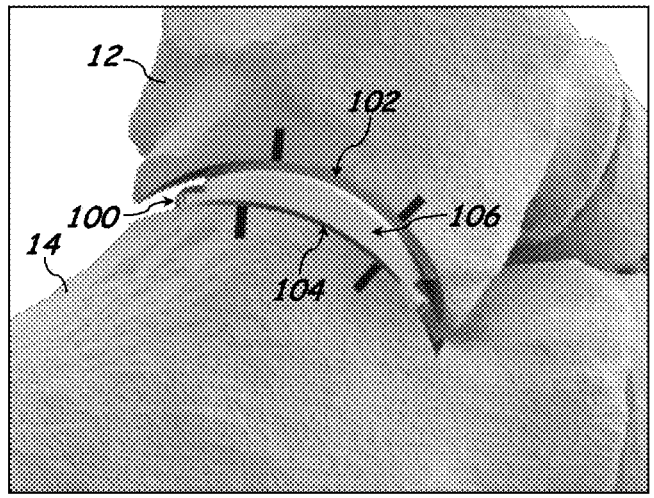
FIG. 3 is a perspective view of a first exemplary implant system disposed in the subtalar joint of a human foot.
Figure 4:
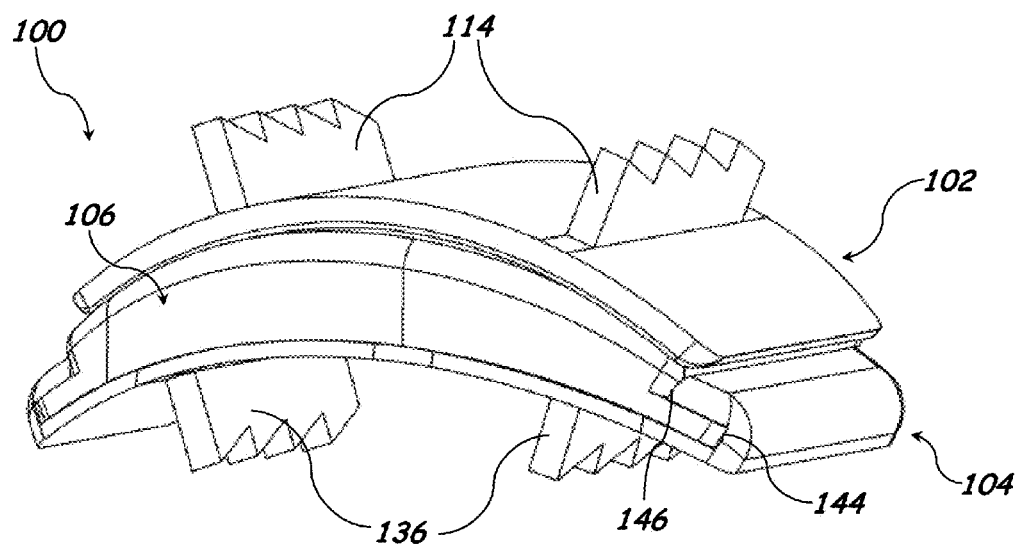
FIG. 4 is a perspective view of the first exemplary implant system illustrated in FIG. 3, free of the subtalar joint.

The following detailed description and the appended drawings describe and illustrate various exemplary surgical implant systems, methods, and components. The description and drawings are exemplary in nature and are provided to enable one skilled in the art to make and use one or more exemplary surgical implant systems and/or components, and/or practice one or more exemplary methods. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "exemplary" refers to "an example of" and is not intended to convey a meaning of an ideal or preferred embodiment. The use of "attached" and grammatically related terms refers to the fixed, releasable, or integrated association of two or more elements and/or devices. Thus, the term "attached" and grammatically related terms includes releasably attaching or fixedly attaching two or more elements and/or devices. As used herein, the terms "proximal" and "distal" are used to describe opposing axial ends of the particular elements or features being described.

FIGS. 1 and 2 illustrate an exemplary human foot 10 comprising a talus 12, calcaneus 14, and subtalar joint 16. The posterior facet 18 of the subtalar joint 16 is formed by a concave, or substantially concave, surface 20 on the talus 12 and a convex, or substantially convex, surface 22 on the calcaneus 14, as shown in FIG. 2.

While the systems, methods, and components described herein are exemplified by systems and methods for modifying the posterior facet of the subtalar joint in a human foot, the systems, methods, and components described and illustrated herein can by used to treat any suitable ailment or joint within the body of an animal, including, but not limited to, humans. Skilled artisans will be able to select a suitable ailment and/or joint within the body of an animal to utilize a system and/or method described herein according to a particular embodiment based on various considerations, including the type of ailment and/or the structural arrangement at a treatment site. Example joints considered suitable to utilize a system, method, and/or component described herein include, but are not limited to, the subtalar joint, the talonavicular joint, and the calcaneocuboid joint.

FIGS. 3, 4, 5, and 6 illustrate an exemplary surgical implant system 100 comprising a first implant component 102, a second implant component 104, and an insert 106. First implant component 102 is adapted to be attached to the talus 12 and second implant component 104 is adapted to be attached to the calcaneus 14.

First implant component 102 and second implant component 104 can be formed of any suitable material, and skilled artisans will be able to select a suitable material to form a first implant component and/or second implant component according to a particular embodiment based on various considerations, including the structural arrangement at an implant site and/or the material forming the insert of an implant system. Example materials considered suitable to form a first implant component and/or second implant component include, but are not limited to, biocompatible materials, materials that can be made biocompatible, ceramics, polymers, polyethylene, ultra-high-molecular-weight polyethylene (UHMWPE), metals, tantalum, titanium (Ti), and cobalt alloys (e.g., cobalt-chromium (CoCr), cobalt-chromium-molybdenum (CoCrMo)). It is considered advantageous to form a first implant component and/or second implant component of titanium or ultra-high-molecular-weight polyethylene (UHMWPE) at least because these materials have properties that limit adverse reactions after being implanted and have high wearability.

In the illustrated embodiment, first implant component 102 comprises a first implant proximal end 108, first implant distal end 110, first implant body 112, and a plurality of first implant projections 114.

First implant body 112 defines a convex, or substantially convex, first implant surface 116 and an opposably facing, or substantially opposably facing, concave, or substantially concave, first articulating surface 118. Each of the first implant surface 116 and first articulating surface 118 has a radius of curvature that extends from the first implant proximal end 108 to the first implant distal end 110. First implant surface 116 is smooth, substantially smooth, or uninterrupted and first articulating surface 118 is smooth, substantially smooth, or uninterrupted, such that articulation between articulating surface 118 and insert 106 can be accomplished, as described in more detail herein.

While first implant surface 116 has been described as convex, or substantially convex, and first articulating surface 118 has been described as concave, or substantially concave, the first implant surface and/or first articulating surface of a first implant component can have any suitable structural arrangement. Skilled artisans will be able to select a suitable structural arrangement for the first implant surface and/or first articulating surface of a first implant component according to a particular embodiment based on various considerations, including the structural arrangement at a desired implant site. Example structural arrangements considered suitable for the first implant surface and/or first articulating surface of a first implant component include, but are not limited to, curved, nonuniform, uniform, flat, substantially flat, concave, substantially concave, convex, substantially convex, and any other structural arrangement considered suitable for a particular application.

First implant surface 116 and first articulating surface 118 can have any suitable radius of curvature and first implant component can have any suitable dimensions, and skilled artisans will be able to select a suitable radius of curvature for an implant surface and first articulating surface of a first implant component and/or suitable dimensions for a first implant component according to a particular embodiment based on various considerations, including the structural arrangement at a desired implant site. For example, one or more first implant components can be provided in a kit such that one, two, at least two, or a plurality of the implant components has/have a different radius of curvature on an implant surface and/or first articulating surface and/or different dimensions. It is considered advantageous to provide a variety of differently sized first implant components at least because this provides a mechanism for matching a first implant component with the anatomy at an implant site. It is considered advantageous for a first implant component to have a thickness that is able to withstand the forces placed on the first implant component and/or an implant site (e.g., subtalar joint) during use (e.g., walking, running) and prevent, or substantially prevent, fracture of and/or damage to the first implant component.

While each of the first implant surface 116 and first articulating surface 118 has been described as having a radius of curvature that extends from the first implant proximal end 108 to the first implant distal end 110, the first implant body of a first implant component can define a radius of curvature along any suitable length of a surface. Skilled artisans will be able to select a suitable length to define a radius of curvature on a surface according to a particular embodiment based on various considerations, including the structural configuration at an implant site. Example lengths considered suitable to define a radius of curvature on the surface of a first implant component include, but are not limited to, from the first implant proximal end to the first implant distal end of a first implant component, from a location distal to the first implant proximal end to the first implant distal end of a first implant component, between the first implant proximal end and the first implant distal end of a first implant component, and from the first implant proximal end to a location proximal to the first implant distal end of a first implant component.

While first implant surface 116 has been described as smooth, substantially smooth, or uninterrupted, the first implant surface of a first implant component can comprise any suitable texture, roughness, and/or porosity and skilled artisans will be able to select a suitable texture, roughness, and/or porosity for the first implant surface of a first implant component according to a particular embodiment based on various considerations, including the desired amount of bone ingrowth desired between a first implant component and the bone at an implant site. For example, alternative to first implant surface comprising a smooth, substantially smooth, or uninterrupted surface, the first implant surface of a first implant component can comprise a porous, or substantially porous, surface. It is considered advantageous for the first implant surface of a first implant component to have a porous, or substantially porous, surface to increase the amount of bone ingrowth between a first implant component and the bone at an implant site.

In the illustrated embodiment, each projection of the plurality of first implant projections 114 has a first implant projection proximal end 120, first implant projection distal end 122, and extends outward and away, or radially outward, from first implant surface 116 at a 90 degree, or substantially 90 degree, angle from a first implant projection first end 124 to a first implant projection second end 126. Each projection of the plurality of first implant projections 114 is elongated, is disposed between first implant proximal end 108 and first implant distal end 110, and defines a serrated first implant projection second end 126. It is considered advantageous for each projection of the plurality of first implant projections 114 to define a serrated first implant projection second end 126 at least because this structural configuration provides a mechanism for increasing the amount of attachment between first implant component 102 and the surface at an implant site.

The serrated first implant projection second end 126 of each projection of the plurality of first implant projections 114 is configured such that it has a plurality of projection declining surfaces 127. Each projection declining surface of the plurality of projection declining surfaces 127 extends from a first end 127' toward first implant distal end 110 to a second end 127". The first end 127' is disposed a first projection distance from first implant surface 116 and the second end 127" is disposed a second projection distance from first implant surface 116. The first projection distance is greater than the second projection distance. This configuration is considered advantageous at least because it provides a mechanism for reducing the complexity of implanting first implant component 102 at an implant site while also preventing, or substantially preventing, first implant component 102 from becoming loose after being implanted. For example, during implantation, first implant component 102 can be introduced at in implant site without the serrated first implant projection second end 126 of each projection of the plurality of projections 114 increasing resistance, or substantially increasing resistance. In addition, after implantation, the serrated first implant projection second end 126 of each projection of the plurality of projections 114 will be forced into the treatment site upon the application of force on first articulating surface 118 and/or toward first implant proximal end 108.

While each projection of the plurality of first implant projections 114 has been illustrated and described as disposed between the first implant proximal end 108 and first implant distal end 110, a projection can be positioned at any suitable location on the implant component and can extend any suitable length along the implant component. Skilled artisans will be able to select a suitable location to position a projection on an implant component and a suitable length for a projection according to a particular embodiment based on various considerations, including the structural arrangement of the desired implant site. Example positions and lengths considered suitable for a projection of an implant component include, but are not limited to, a projection that is disposed on the implant surface of an implant component and extends from the first implant proximal end to the first implant distal end, a projection that is disposed on the implant surface of an implant component and extends from the first implant proximal end to a location proximal to the first implant distal end, a projection that is disposed on the implant surface of an implant component and extends between the first implant proximal end and the first implant distal end, and a projection that is disposed on the implant surface of an implant component and extends from a location between the first implant proximal end and the first implant distal end to the first implant distal end.

While a plurality of first implant projections 114 has been described and illustrated, any suitable number of projections can be included on a first implant component, and skilled artisans will be able to select a suitable number of projections for inclusion on a first implant component according to a particular embodiment based on various considerations, including the structural arrangement at a desired implant site. Example number of projections considered suitable to include on a first implant component include, but are not limited to, one, at least one, two, three, four, five, a plurality, and any other number considered suitable for a particular application. If more than one implant projection is included on a first implant component, the implant projections can be disposed on a first implant surface in any suitable structural configuration. For example, the implant projections can be disposed linearly between a first implant proximal end and a first implant distal end and/or staggered between a first implant proximal end and a first implant distal end.

While the first implant projection second end 126 of each projection of the plurality of first implant projections 114 has been described and illustrated as serrated, the first implant projection second end of a projection can have any suitable structural configuration. Skilled artisans will be able to select a suitable structural configuration for the first implant projection second end of a projection according to a particular embodiment based on various considerations, including the structural arrangement of a desired implant site. Example structural configurations considered suitable for the first implant projection second end of a projection include, but are not limited to, tapered, pointed, smooth, substantially smooth, porous, substantially porous, serrated, serrated having one or more identical teeth, serrated having a first tooth and a second tooth with a different structural configuration, serrated having at least two teeth with different structural configurations, serrated having a first set of teeth with a first configuration and a second set of teeth with a second structural configuration different than the first structural configuration, and any other structural configuration considered suitable for a particular application. For example, a projection declining surface of the plurality of projection declining surfaces 127 and/or any other portion of a first implant projection of the plurality of first implant projections 114 can include one or more cavities or comprise a porous, or substantially porous, surface to allow for bone ingrowth. Example structural configurations for a tooth of a serrated first implant projection second end include, but are not limited to, triangular, square, circular, curved, and any other structural configuration considered suitable for a particular application.

In the illustrated embodiment, second implant component 104 comprises a second implant proximal end 130, second implant distal end 132, second implant body 134, and a plurality of second implant projections 136.

Second implant body 134 defines a concave, or substantially concave, second implant surface 138, recess 139, and a plurality of recess projections 140. Second implant surface 138 is smooth, substantially smooth, or uninterrupted and has a radius of curvature that extends from the second implant proximal end 130 to the second implant distal end 132.

Recess 139 is adapted to receive a portion, or the entirety, of insert 106, as described in more detail herein. Recess 139 has a recess length 141, recess base 142, recess distal end 143, recess first portion 144, and a recess second portion 146. Recess 139 extends into second implant body 134 from a side opposably facing second implant surface 138 to recess base 142 and from the second implant proximal end 130 toward the second implant distal end 132 to recess distal end 143 disposed between second implant proximal end 130 and second implant distal end 132. Recess length 141 extends from the second implant proximal end 130 toward the second implant distal end 132 to recess distal end 143.

Each projection of the plurality of recess projections 140 extends into recess 139 along a portion, or the entirety, of recess length 141 and has a tapered edge that is adapted to interact with a portion of insert 106 to releasably attach insert 106 to second implant component 104. Recess base 142 is opposably facing, or substantially opposably facing, second implant surface 138, is convex, or substantially convex, and is smooth, substantially smooth, or uninterrupted. Recess base 142 has a radius of curvature that extends from the second implant proximal end 130 to recess distal end 143. Recess first portion 144 extends from recess base 142 and away from the second implant surface 138 to the plurality of recess projections 140 and has a recess first portion width 145 along the second implant proximal end 130. Recess second portion 146 extends from the recess first portion 144 and away from the second implant surface 138 and has a recess second portion width 147 along the second implant proximal end 130 that is measured from a first recess projection of the plurality of recess projections 140 to a second recess projection of the plurality of recess projections 140. The recess first portion width 145 is different than the recess second portion width 147. In the illustrated embodiment, recess first portion width 145 is greater than the recess second portion width 147. However, recess first portion width 145 can have any suitable width. Example widths considered suitable for a recess first portion width include, but are not limited to, equal to, substantially equal to, greater than, or less than, a recess second portion width.

While second implant surface 138 has been described as concave, or substantially concave, and recess base 142 has been described as convex, or substantially convex, the second implant surface and recess base of a second implant component can have any suitable structural arrangement. Skilled artisans will be able to select a suitable structural arrangement for the second implant surface and/or recess base of a second implant component according to a particular embodiment based on various considerations, including the structural arrangement at a desired implant site and/or the structural arrangement of the insert of an implant system. Example structural arrangements considered suitable for the second implant surface and/or recess base of a second implant component include, but are not limited to, curved, nonuniform, uniform, flat, substantially flat, convex, substantially convex, concave, substantially concave, and any other structural arrangement considered suitable for a particular application.

Second implant surface 138 and recess base 142 can have any suitable radius of curvature and second implant component can have any suitable dimensions, and skilled artisans will be able to select a suitable radius of curvature for an implant surface and recess base of a second implant component and/or suitable dimensions for a second implant component according to a particular embodiment based on various considerations, including the structural arrangement at a desired implant site. For example, one or more second implant components can be provided in a kit such that one, two, at least two, or a plurality of the implant components has/have a different radius of curvature on an implant surface and/or recess base and/or different dimensions. It is considered advantageous to provide a variety of differently sized second implant components at least because this provides a mechanism for matching a second implant component with the anatomy at an implant site. It is considered advantageous for a second implant component to have a thickness that is able to withstand the forces placed on the second implant component and/or an implant site (e.g., subtalar joint) during use (e.g., walking, running) and prevent, or substantially prevent, fracture of and/or damage to the second implant component.

While second implant surface 138 has been described as having a radius of curvature that extends from the second implant proximal end 130 to the second implant distal end 132 and recess base 142 has been described as having a radius of curvature that extends from the second implant proximal end 130 to recess distal end 143, the second implant body can define a radius of curvature along any suitable length of a surface. Skilled artisans will be able to select a suitable length to define a radius of curvature on the surface of a second implant component according to a particular embodiment based on various considerations, including the structural configuration at an implant site. Example lengths considered suitable to define a radius of curvature on the surface of a an implant component include, but are not limited to, from the second implant proximal end to the second implant distal end of a second implant component, from a location distal to the second implant proximal end to the second implant distal end of a second implant component, between the second implant proximal end and the second implant distal end of a second implant component, from the second implant proximal end to a location proximal to the second implant distal end of a second implant component, from the second implant proximal end to the recess distal end of a second implant component, from a location distal to the second implant proximal end to the recess distal end of a second implant component, between the second implant proximal end and the recess distal end of a second implant component, and from the second implant proximal end to a location proximal to the recess distal end of a second implant component.

While second implant surface 138 has been described as smooth, substantially smooth, or uninterrupted, the second implant surface of a second implant component can comprise any suitable texture, roughness, and/or porosity and skilled artisans will be able to select a suitable texture, roughness, and/or porosity for the second implant surface of a second implant component according to a particular embodiment based on various considerations, including the desired amount of bone ingrowth desired between a second implant component and the bone at an implant site. For example, alternative to second implant surface comprising a smooth, substantially smooth, or uninterrupted surface, the second implant surface of a second implant component can comprise a porous, or substantially porous, surface. It is considered advantageous for the implant surface of a second implant component to have a porous, or substantially porous, surface to increase the amount of bone ingrowth between a second implant component and the bone at an implant site.

While second implant body 134 has been described as defining a recess 139 with a recess length 141, recess first portion 144, and a recess second portion 146 and defining a plurality of recess projections 140, the body of an implant component can define a recess having any suitable structural arrangement to provide a mechanism for attaching an insert to an implant component. Skilled artisans will be able to select a suitable structural arrangement for an implant component and/or recess of an implant component according to a particular embodiment based on various considerations, including the structural arrangement at an implant site and/or the structural arrangement of the insert of an implant system. For example, the body of an implant component can define a recess having only a single portion extending along a recess length that is equal to, or substantially equal to, a portion, or the entirety, of the length of the implant component (e.g., recess can extend the entire axial length of an implant component from the implant proximal end to the implant distal end).

While each projection of the plurality of recess projections 140 has been described and illustrated as having a tapered configuration, a recess projection can have any suitable structural configuration, and skilled artisans will be able to select a suitable structural configuration for a recess projection according to a particular embodiment based on various considerations, including the material forming the insert of an implant system. Example structural arrangements considered suitable for a projection include, but are not limited to, flat, or substantially flat, tapered, curved, serrated, and any other structural arrangement considered suitable for a particular application.

In the illustrated embodiment, each projection of the plurality of second implant projections 136 has a second implant projection proximal end 150, second implant projection distal end 152, and extends outward and away, or radially outward, from second implant surface 138 at a 90 degree, or substantially 90 degree, angle from a second implant projection first end 154 to a second implant projection second end 156. Each projection of the plurality of second implant projections 136 is elongated, is disposed between second implant proximal end 130 and second implant distal end 132, and defines a serrated second implant projection second end 156. It is considered advantageous for each projection of the plurality of second implant projections 136 to define a serrated second implant projection second end 156 at least because this structural configuration provides a mechanism for increasing the amount of attachment between the second implant component 104 and the surface at an implant site.

The serrated second implant projection second end 156 of each projection of the plurality of second implant projections 136 is configured such that it has a plurality of projection declining surfaces 157. Each projection declining surface of the plurality of projection declining surfaces 157 extends from a first end 157' toward second implant distal end 132 to a second end 157". The first end 157' is disposed a first projection distance from second implant surface 138 and the second end 157" is disposed a second projection distance from second implant surface 138. The first projection distance is greater than the second projection distance. This configuration is considered advantageous at least because it provides a mechanism for reducing the complexity of implanting second implant component 104 at an implant site while also preventing, or substantially preventing, second implant component 104 from becoming loose after being implanted. For example, during implantation, second implant component 104 can be introduced at in implant site without the serrated second implant projection second end 156 of each projection of the plurality of projections 136 increasing resistance, or substantially increasing resistance. In addition, after implantation, the serrated second implant projection second end 156 of each projection of the plurality of projections 136 will be forced into the treatment site upon the application of force on second implant body 134 and/or toward second implant proximal end 130.

While each projection of the plurality of second implant projections 136 has been illustrated and described as disposed between the second implant proximal end 130 and second implant distal end 132, a projection can be positioned at any suitable location on an implant component and can extend any suitable length along the implant surface of the implant component. Skilled artisans will be able to select a suitable location to position a projection and a suitable length for a projection according to a particular embodiment based on various considerations, including the structural arrangement of the desired implant site. Example positions and lengths considered suitable for a projection include, but are not limited to, a projection that is disposed on the implant surface of an implant component and extends from the second implant proximal end to the second implant distal end, a projection that is disposed on the implant surface of an implant component and extends from the second implant proximal end to a location proximal to the second implant distal end, a projection that is disposed on the implant surface of an implant component and extends between the second implant proximal end and the second implant distal end, and a projection that is disposed on the implant surface of an implant component and extends from a location between the second implant proximal end and the second implant distal end to the second implant distal end.

While a plurality of second implant projections 136 has been described and illustrated, any suitable number of projections can be included on a second implant component, and skilled artisans will be able to select a suitable number of projections for inclusion on a second implant component according to a particular embodiment based on various considerations, including the structural arrangement at a desired implant site. Example number of projections considered suitable to include on a second implant component include, but are not limited to, one, at least one, two, three, four, five, a plurality, and any other number considered suitable for a particular application. If more than one implant projection is included on a second implant component, the implant projections can be disposed on a second implant surface in any suitable structural configuration. For example, the implant projections can be disposed linearly between a second implant proximal end and a second implant distal end and/or staggered between a second implant proximal end and a second implant distal end.

While the second implant projection second end 156 of each projection of the plurality of second implant projections 136 has been described and illustrated as serrated, the second implant projection second end of a projection can have any suitable structural configuration. Skilled artisans will be able to select a suitable structural configuration for the second implant projection second end of a projection according to a particular embodiment based on various considerations, including the structural arrangement of the desired implant site. Example structural configurations considered suitable for the second implant projection second end of a projection include, but are not limited to, tapered, pointed, smooth, substantially smooth, porous, substantially porous, serrated, serrated having one or more identical teeth, serrated having a first tooth and a second tooth with a different structural configuration, serrated having at least two teeth with different structural configurations, serrated having a first set of teeth with a first configuration and a second set of teeth with a second structural configuration different than the first structural configuration, and any other structural configuration considered suitable for a particular application. For example, a projection declining surface of the plurality of projection declining surfaces 157 and/or any other portion of a second implant projection of the plurality of second implant projections 136 can include one or more cavities or comprise a porous, or substantially porous, surface to allow for bone ingrowth. Example structural configurations for a tooth of a serrated second implant projection second end include, but are not limited to, triangular, square, circular, curved, and any other structural configuration considered suitable for a particular application.

In the illustrated embodiment, a first projection of the plurality of first implant projections 114 is disposed parallel, or substantially parallel, to a second projection of the plurality of first implant projections 114 and a first projection of the plurality of second implant projections 136 is disposed parallel, or substantially parallel, to a second projection of the plurality of second implant projections 136. It is considered advantageous to position a first projection of the plurality of first implant projections 114 parallel, or substantially parallel, to a second projection of the plurality of first implant projections 114 and a first projection of the plurality of second implant projections 136 parallel, or substantially parallel, to a second projection of the plurality of second implant projections 136 at least because this configuration allows for the first implant component 102 and/or second implant component 104 to be seated properly at the implant site and provides a mechanism for reducing the complexity of the implant procedure during the introduction of the first implant component 102 and/or second implant component 104.

While first implant component 102 has been illustrated and described as having a first projection of the plurality of first implant projections 114 being disposed parallel, or substantially parallel, to a second projection of the plurality of first implant projections 114 and second implant component 104 has been illustrated and described as having a first projection of the plurality of second implant projections 136 being disposed parallel, or substantially parallel, to a second projection of the plurality of first implant projections 136, a first projection of a plurality of implant projections can be disposed at any suitable angle to a second projection of the plurality of implant projections. Skilled artisans will be able to select a suitable angle to position a first projection of a plurality of implant projections with respect to a second projection of the plurality of implant projections, according to a particular embodiment based on various considerations, including the number of projections disposed on a first implant component and/or the structural arrangement at a desired implant site.

While each implant projection of the plurality of first implant projections 114 has been illustrated and described as extending outward and away from first implant surface 116 at a 90 degree, or substantially 90 degree, angle, and each projection of the plurality of second implant projections 136 has been illustrated and described as extending outward and away from second implant surface 138 at a 90 degree, or substantially 90 degree, angle, a projection can extend outward and away from an implant surface at any suitable angle and comprise any suitable length. Skilled artisans will be able to select a suitable angle and length for a projection to extend outward and away from an implant surface of an implant component according to a particular embodiment based on various considerations, including the structural arrangement at a desired implant site. Example angles considered suitable for a projection to extend outward and away from an implant surface of an implant component include, but are not limited to, a 90 degree angle, a substantially 90 degree angle, a 45 degree angle, a substantially 45 degree angle, an acute angle, an obtuse angle, an angle such that the projection is normal to the implant surface, an angle such that the projection is substantially normal to the implant surface, and any other angle considered suitable for a particular application. It is considered advantageous for a projection to extend outward and away from a first implant surface and/or second implant surface at least a length that will provide resistance to sliding after implantation and reduces interference during implantation of the component.

Insert 106 can be formed of any suitable material, and skilled artisans will be able to select a suitable material to form an insert of an implant system according to a particular embodiment based on various considerations, including the material forming a first implant component and/or second implant component of an implant system. Example materials considered suitable to form an insert include, but are not limited to, biocompatible materials, materials that can be made biocompatible, ceramics, polymers, polyethylene, and ultra-high-molecular-weight polyethylene (UHMWPE), metals, tantalum, titanium (Ti), and cobalt alloys (e.g., cobalt-chromium (CoCr), cobalt-chromium-molybdenum (CoCrMo)). It is considered advantageous to form insert 106 of ultra-high-molecular-weight polyethylene at least because ultra-high-molecular-weight polyethylene can be easily machined or molded into a desired structural arrangement and has increased wearability and biocompatibility as compared to other materials. In addition, ultra-high-molecular-weight polyethylene has decreased frictional properties (e.g., lower coefficient of friction) as compared to other materials and wear particulates are easily phagocytized when compared to particulates formed from other materials.

In the illustrated embodiment, insert 106 comprises an insert proximal end 160, insert distal end 162, and an insert body 164. Insert 106 is adapted to be releasably attached to the second implant component 104, as described in more detail herein.

Insert body 164 defines an insert base 166, insert articulating portion 168, insert recess 170, and an insert shoulder 172. Insert base 166 has an insert base surface 174 and the insert articulating portion 168 has an insert articulating surface 176. Insert base surface 174 has a radius of curvature that extends from insert proximal end 160 to shoulder 172 and insert articulating surface 176 has a radius of curvature that extends from the insert proximal end 160 to the insert distal end 162. Insert base surface 174 is concave, or substantially concave, and is opposably facing, or substantially opposably facing, insert articulating surface 176 which is convex, or substantially convex. Insert base surface 174 is smooth, substantially smooth, or uninterrupted, and is complementary to recess base 142 such that insert 106 is slidable along recess base 142 and releasable attachment between insert 106 and second implant component 104 can be accomplished. Insert articulating surface 176 is smooth, substantially smooth, or uninterrupted, and is complementary to first articulating surface 118 such that insert 106 can articulate with first implant component 102. Thus, insert articulating surface 176 is adapted to articulate with first articulating surface 118.

Insert base 166 has an insert base width 167 along insert proximal end 160 and insert articulating portion 168 has an insert articulating width 169 along insert proximal end 160. Insert base width 167 is equal to, substantially equal to, less than, or greater than, recess first portion width 145. Insert articulating width 169 is equal to, substantially equal to, less than, or greater than, recess second portion width 147. It is considered advantageous to include an insert 106 having an insert base width 167 that is equal to, substantially equal to, or greater than, the recess first portion width 145 at least because this structural arrangement provides a mechanism for introducing insert base 166 into recess first portion 144 and provides a mechanism for achieving a friction fit between insert and second implant component 104. It is considered advantageous to include an insert 106 having a insert articulating width 169 that is equal to, substantially equal to, or greater than, the recess second portion width 147 at least because this structural arrangement provides a mechanism for achieving a friction fit between insert 106 and second implant component 104. Thus, each of insert base 166 and insert articulating portion 168 is adapted to interact with recess 139 (e.g., each projection of the plurality of recess projections 140) to create a friction fit between insert 106 and second implant component 104.

Insert recess 170 extends into insert body 164 from insert distal end 162 and toward insert proximal end 160 and from insert base surface 174 toward insert articulating surface 176 to define insert shoulder 172. Insert shoulder 172 is disposed between insert proximal end 160 and insert distal end 162 and is disposed a distance from insert proximal end 160 that is equal to, or substantially equal to, recess length 141. Thus, insert base 166 extends from the insert proximal end 160 toward the insert distal end 162 to insert shoulder 172 a distance that is equal to, or substantially equal to, recess length 141. Insert articulating surface 176 extends from insert proximal end 160 to insert distal end 162. This structural arrangement is considered advantageous at least because insert shoulder 172 provides a mechanical stop to distal axial movement of insert 106 when it is being introduced into recess 139. It is considered advantageous for insert articulating surface 176 to extend from insert proximal end 160 to insert distal end 162 at least because this structural arrangement provides additional structure distal to insert shoulder 172 and recess 139 when insert 106 is releasably attached to second implant component 104, that can be utilized for articulation purposes.

Figure 5:
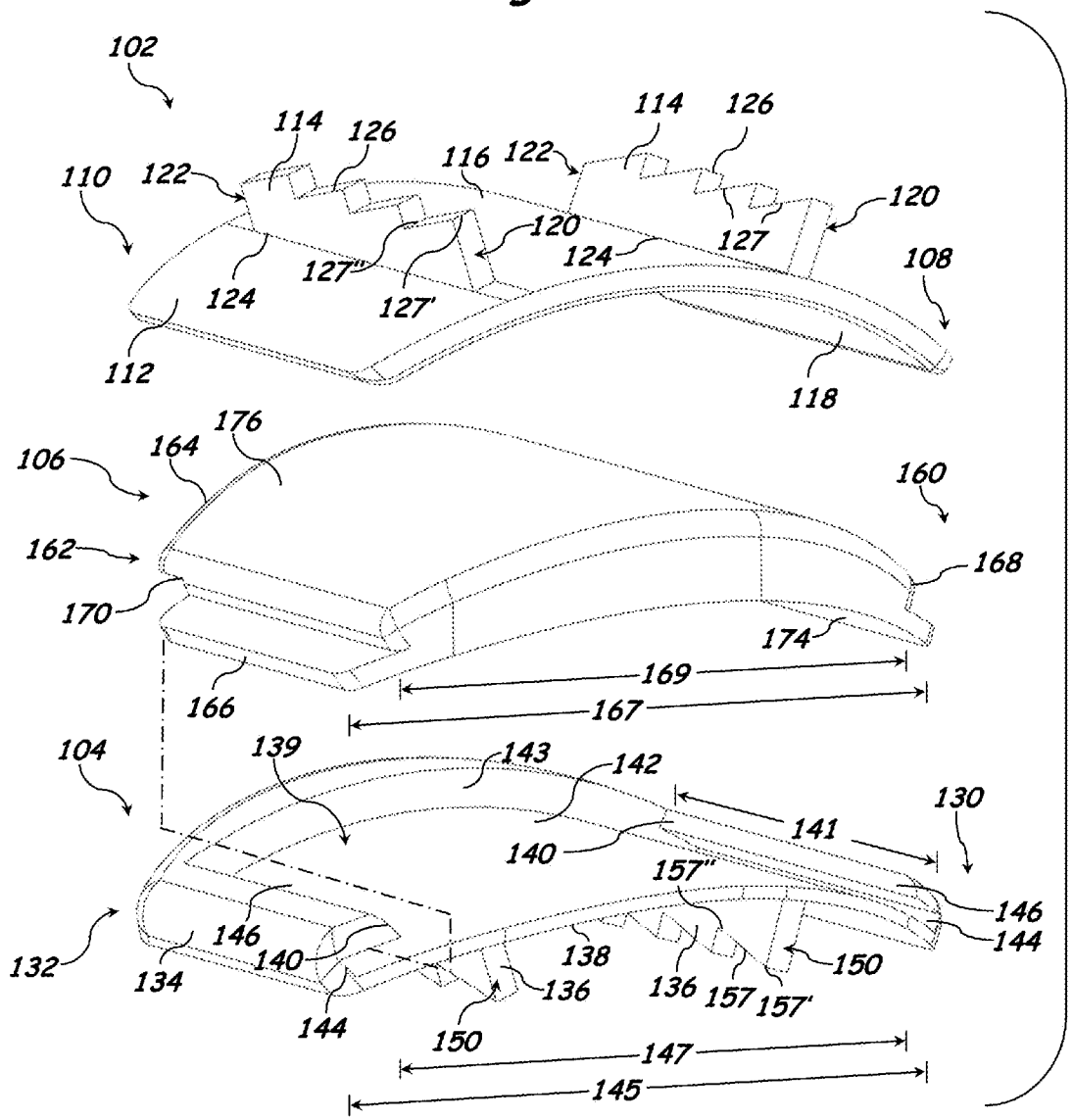
FIG. 5 is an exploded view of the exemplary implant system illustrated in FIG. 4.
Figure 6:
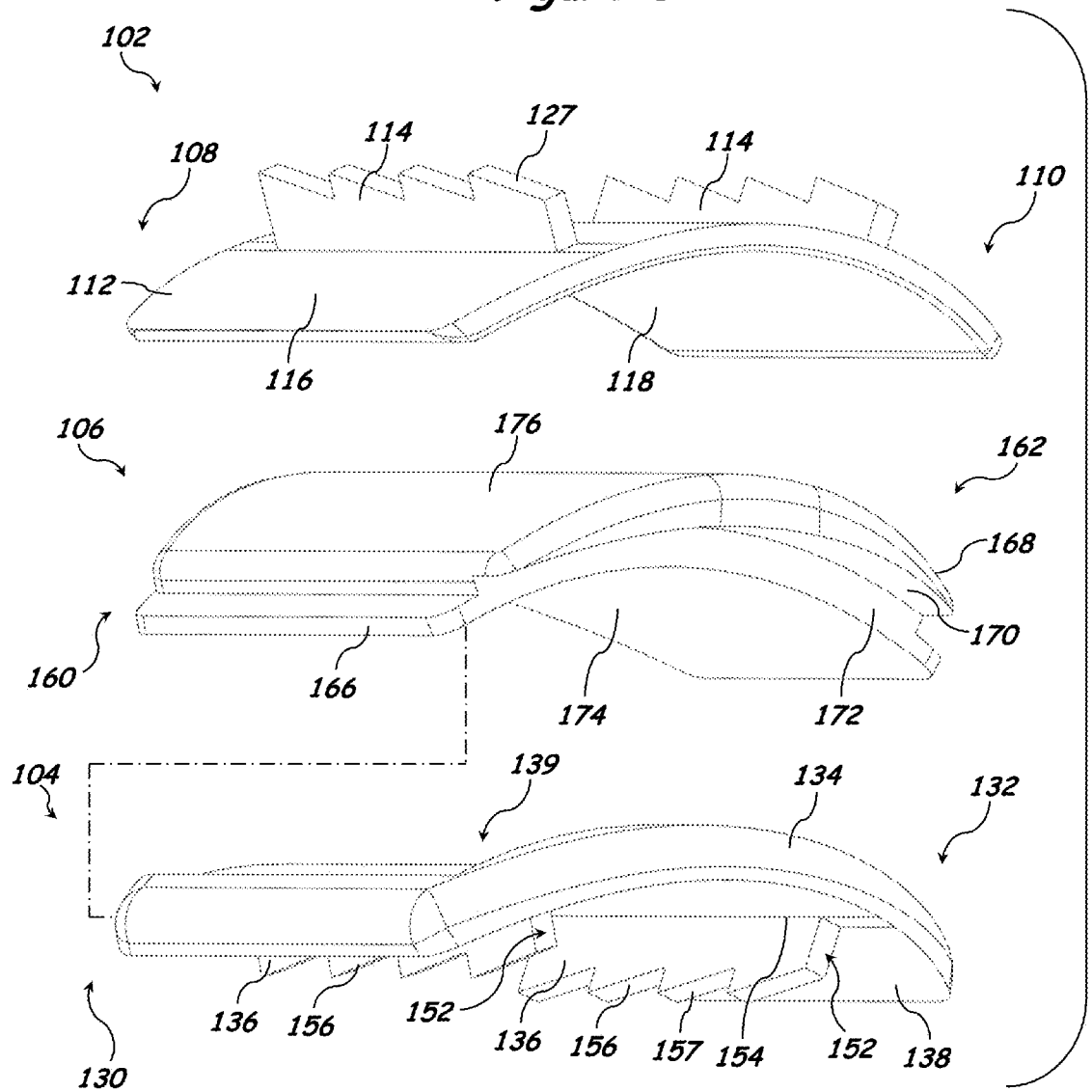
FIG. 6 is another exploded view of the exemplary implant system illustrated in FIG. 4.
Figure 7:
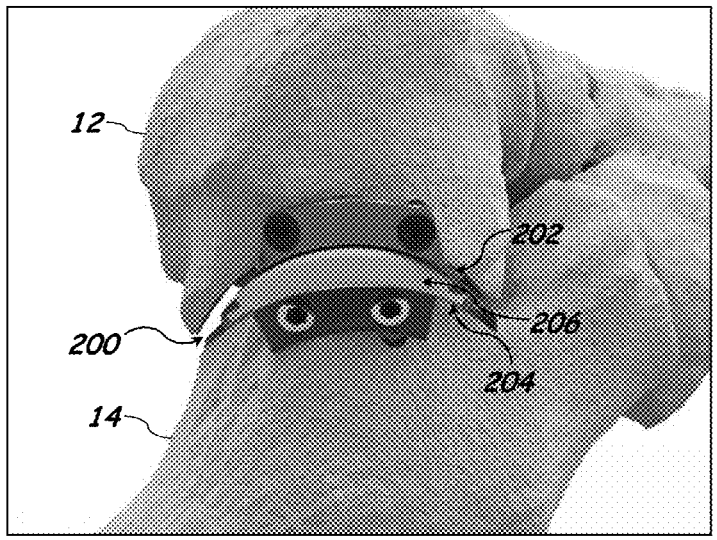
FIG. 7 is a perspective view of a second exemplary implant system disposed in the subtalar joint of a human foot.
Figure 8:
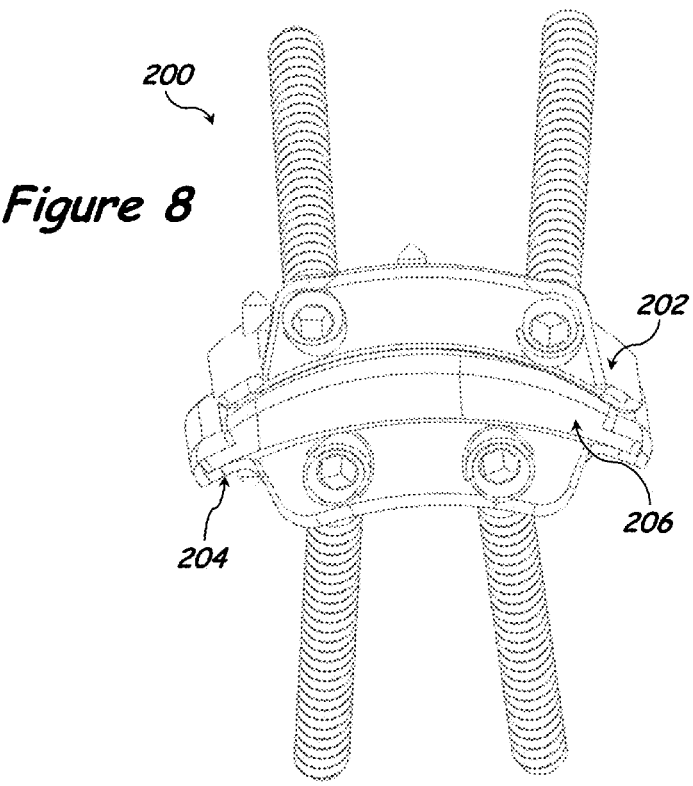
FIG. 8 is a perspective view of the second exemplary implant system illustrated in FIG. 7, free of the subtalar joint.
Figure 9:
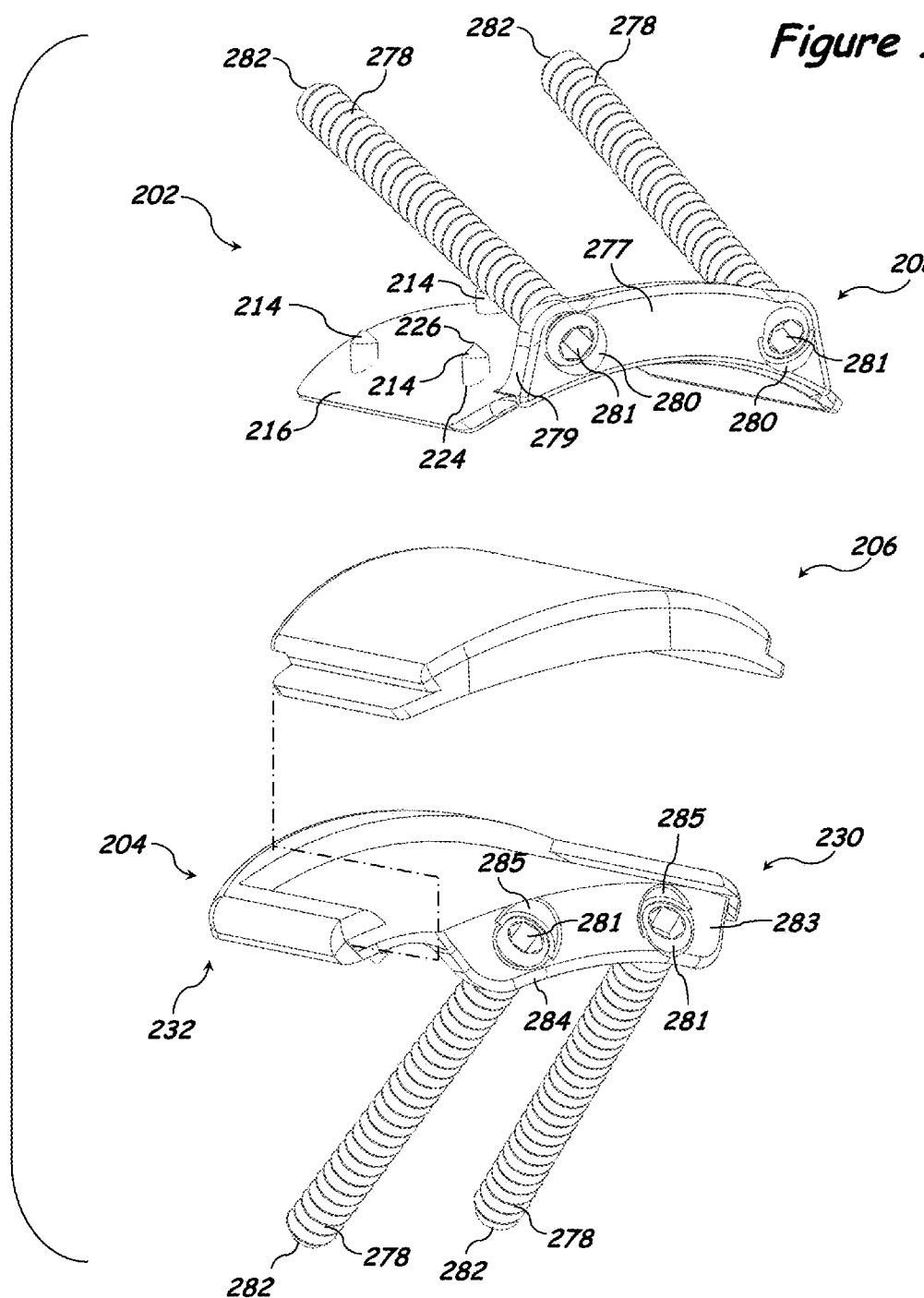
FIG. 9 is an exploded view of the exemplary implant system illustrated in FIG. 8.
Figure 10:
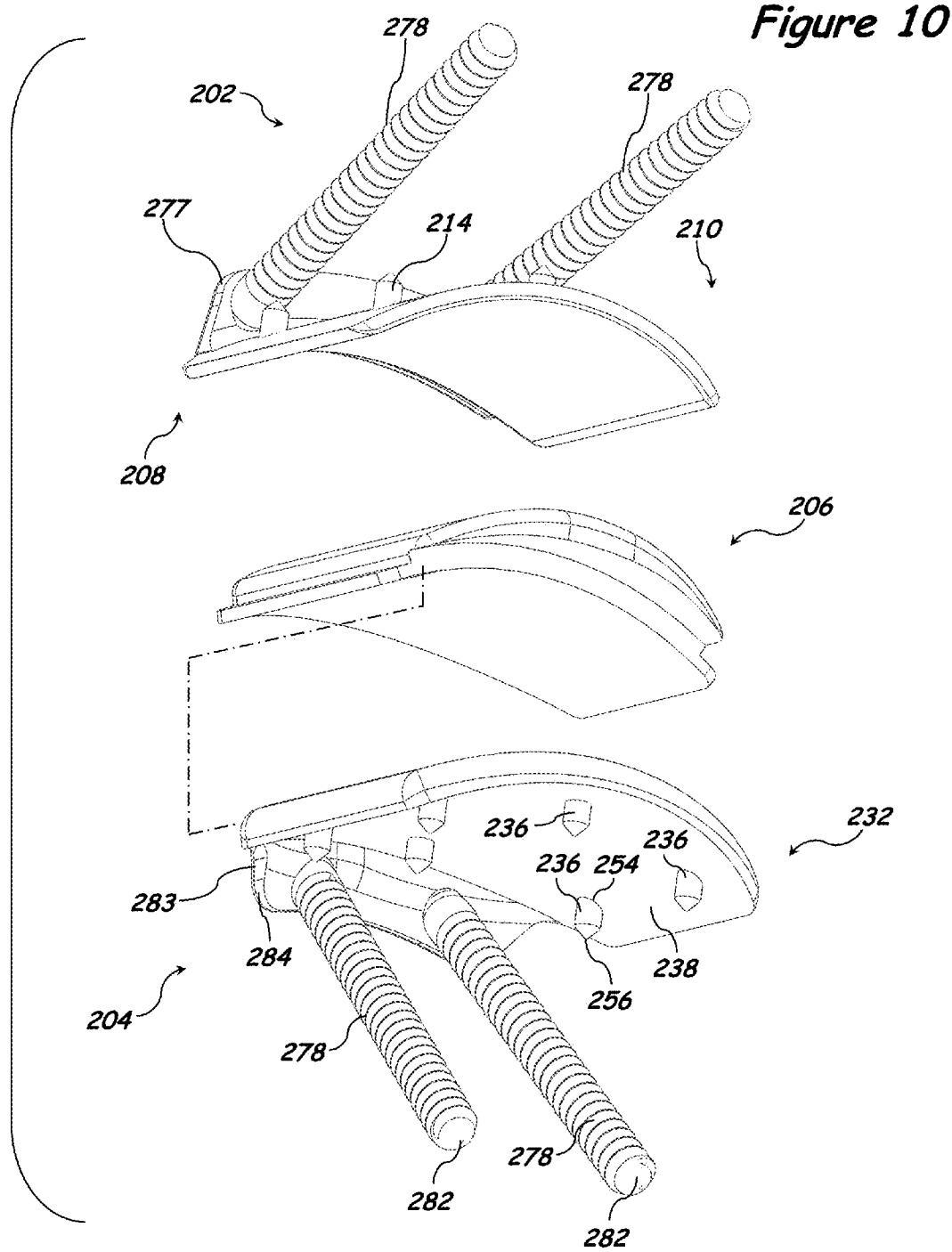
FIG. 10 is another exploded view of the exemplary implant system illustrated in FIG. 8.
Figure 11:
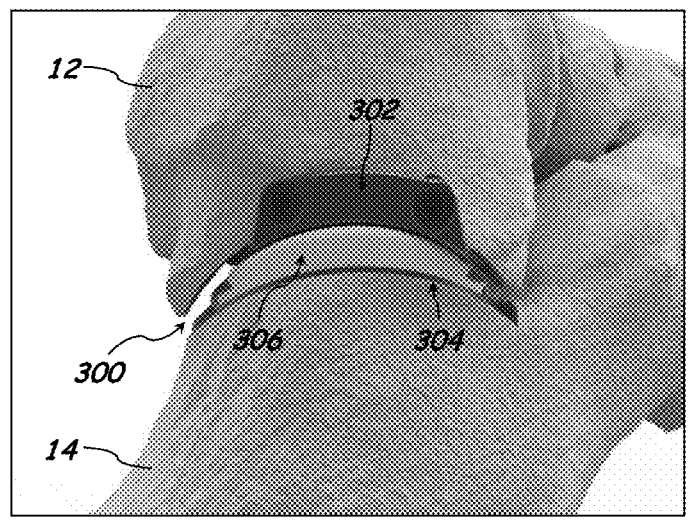
FIG. 11 is a perspective view of a third exemplary implant system disposed in the subtalar joint of a human foot.
Figure 12:
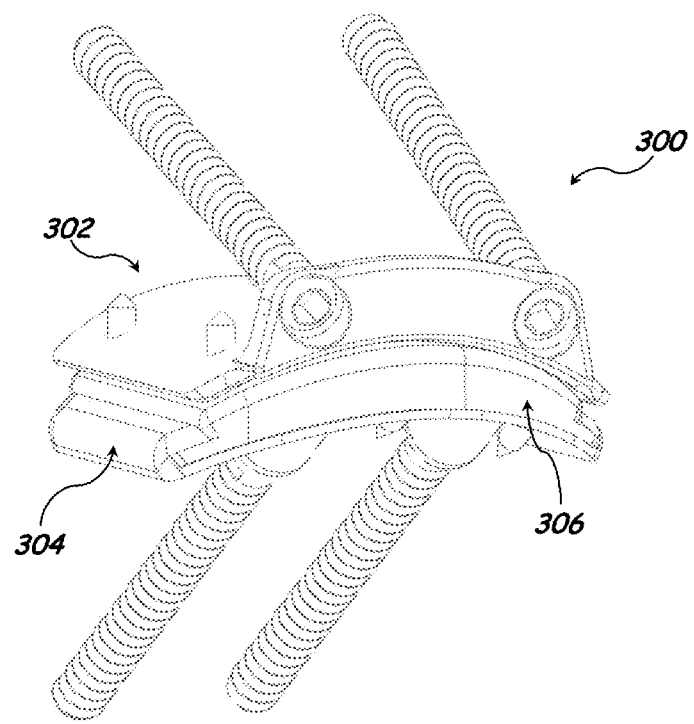
FIG. 12 is a perspective view of the third exemplary implant system illustrated in FIG. 11, free of the subtalar joint.
Figure 13:
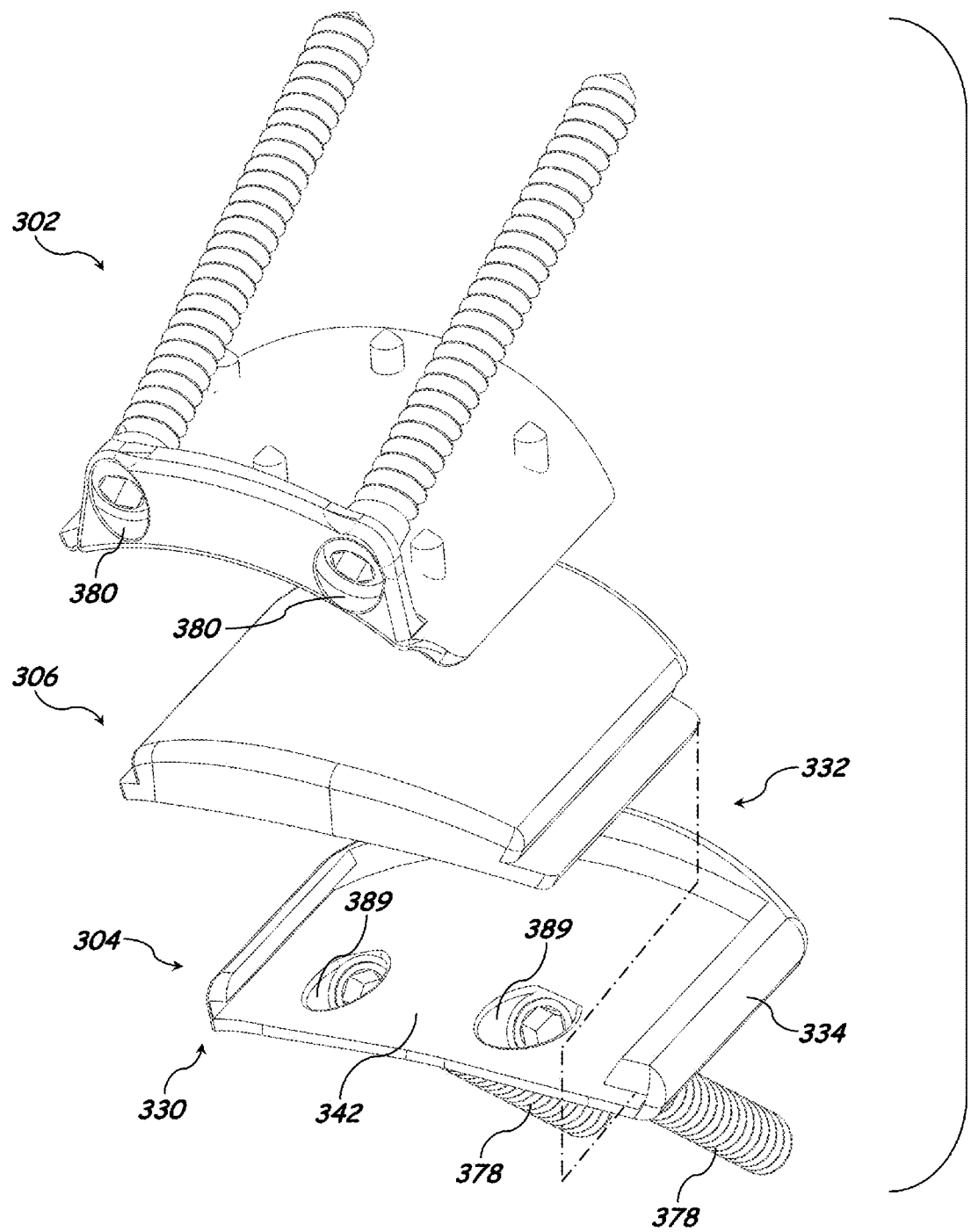
FIG. 13 is an exploded view of the exemplary implant system illustrated in FIG. 12.
Figure 14:
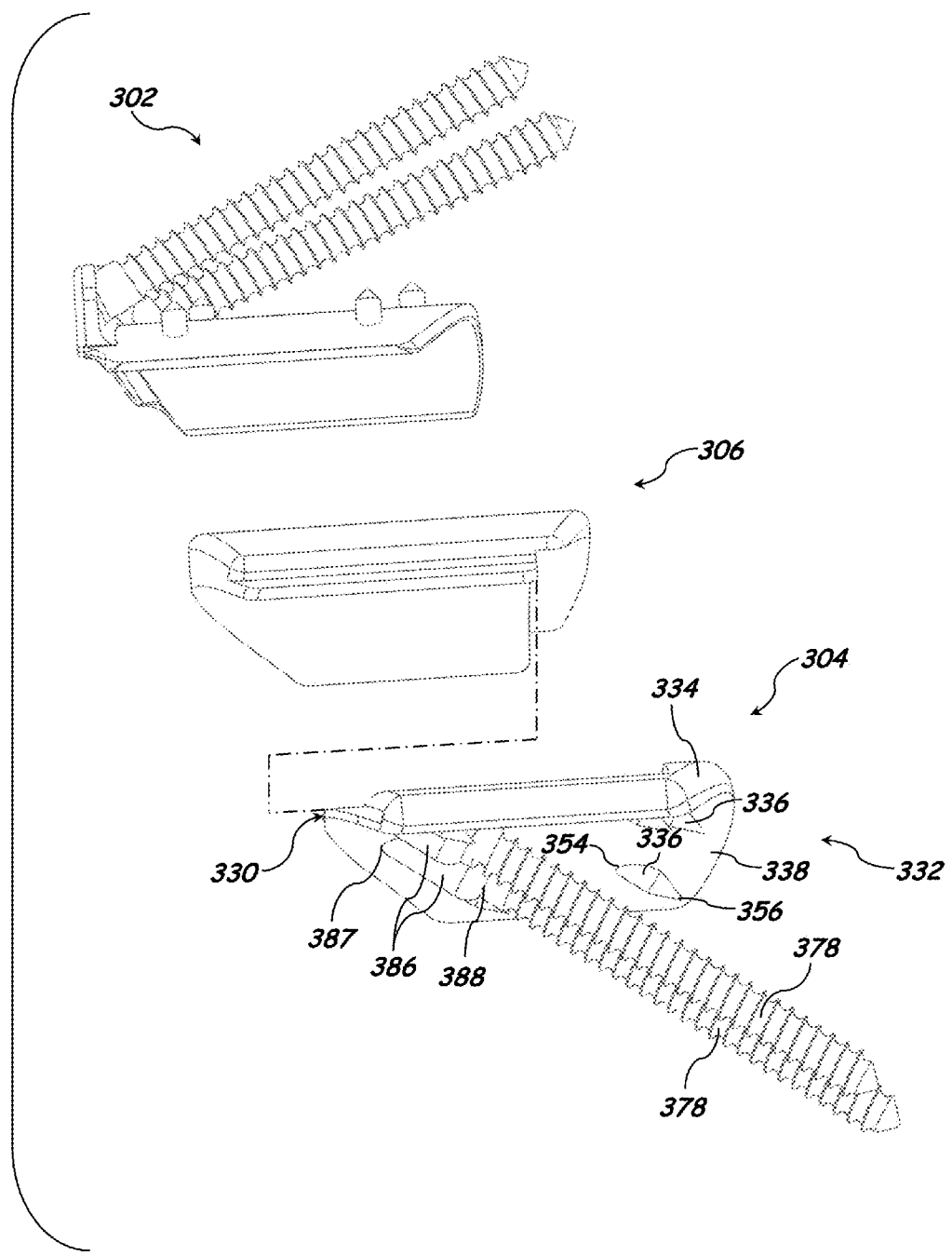
FIG. 14 is another exploded view of the exemplary implant system illustrated in FIG. 12.
Figure 17:
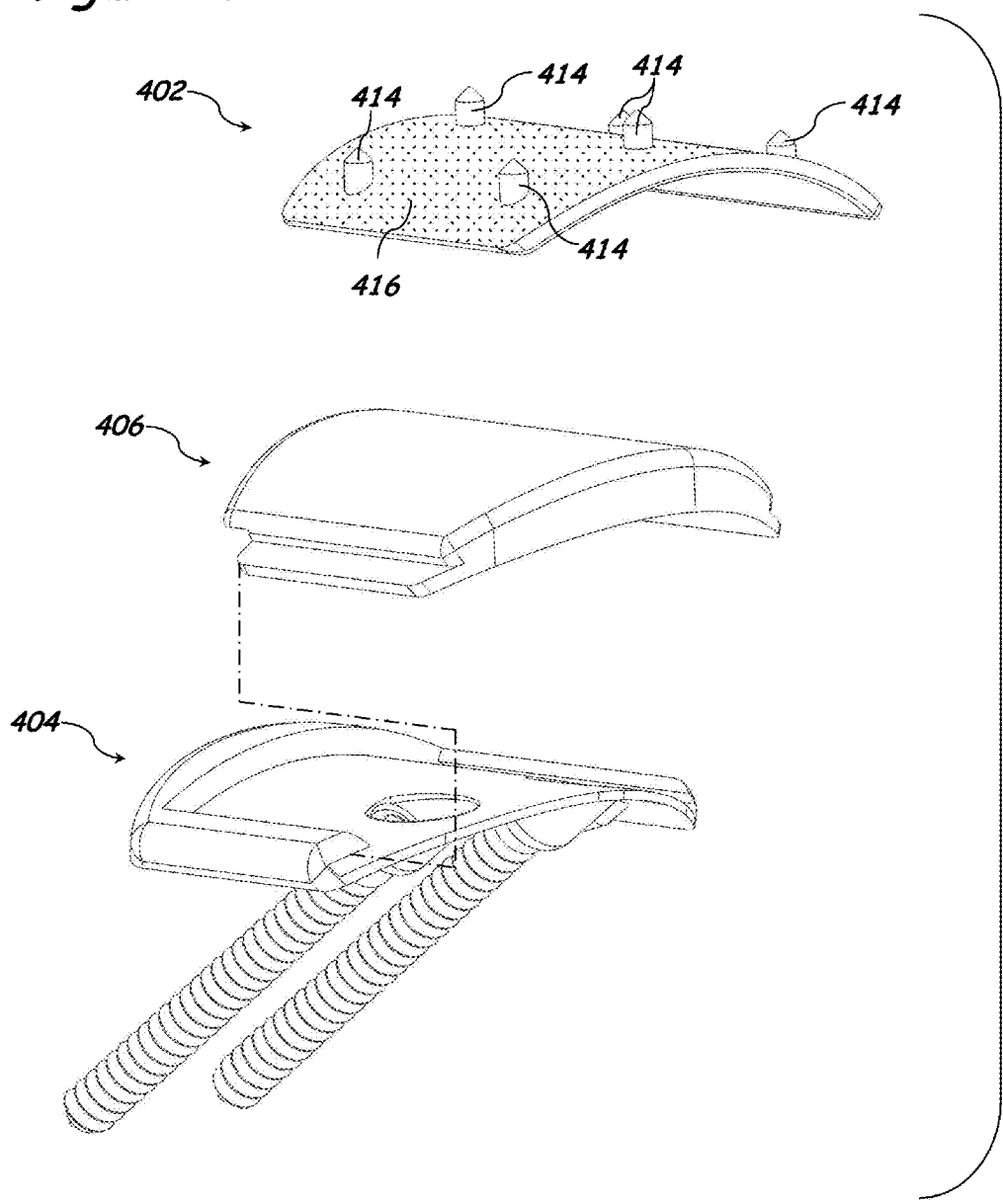
FIG. 17 is an exploded view of the exemplary implant system illustrated in FIG. 16.
Figure 18:
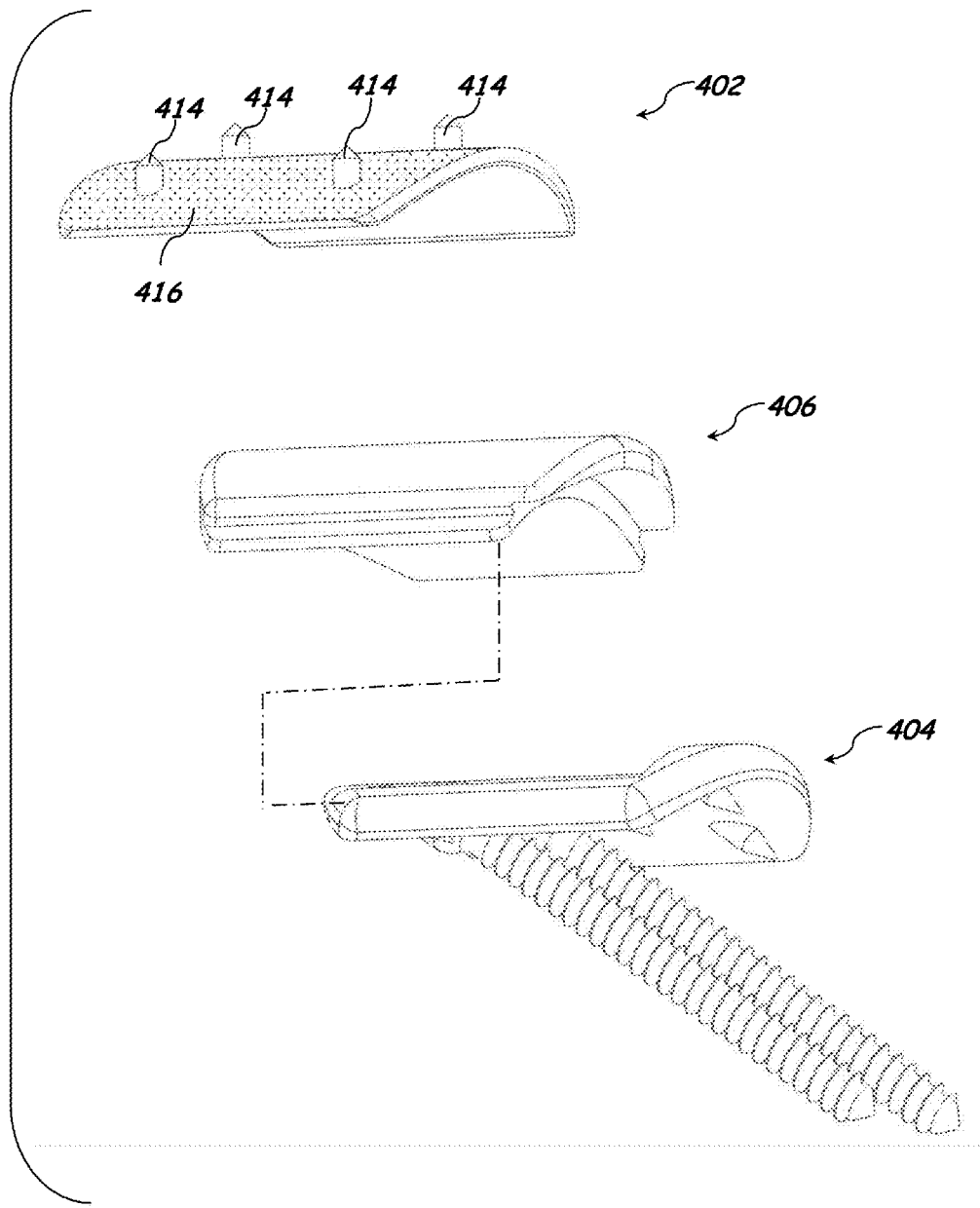
FIG. 18 is another exploded view of the exemplary implant system illustrated in FIG. 16.

Each of FIGS. 5 and 6 illustrates an exploded view of implant system 100 and the relationship between the first implant component 102, second implant component 104, and insert 106. In use, each of the first implant component 102 and second implant component 104 is adapted to be attached at a treatment site such that first articulating surface 118 and recess 139 (e.g., recess base 142) are facing, or substantially facing, each other. Insert 106 is releasably attached to the second implant component 104 by sliding insert base 166 into recess first portion 144 and applying a distally directed axial movement on insert 106 until insert shoulder 172, which is adapted to interact with recess distal end 143, contacts recess distal end 143 and prevents additional distal axial movement of insert 106. Insert articulating surface 176 is adapted to articulate with first articulating surface 118 to provide a range of movement between the insert 106 and first implant component 102.

While insert 106 has been illustrated and described as being releasably attached to an implant component that is attached to the calcaneus, the insert of an implant system can alternatively be attached to an implant component that is attached to the talus such that articulation between the insert and an implant component attached to the calcaneus can be accomplished, as described in more detail herein.

While insert 106 has been described as being releasably attached to second implant component 104 via friction fit between second implant component 104 and insert 106, any suitable method of attachment between an insert and an implant component can be used. Skilled artisans will be able to select a suitable method of attachment between an insert and an implant component according to a particular embodiment based on various considerations, including the materials forming the insert and/or implant component. Example methods of attachment considered suitable between an insert and an implant component include, but are not limited to, using an adhesive, welding, providing a permanent attachment, releasable attachment, fixed attachment, and any other method of attachment considered suitable for a particular application. For example, an insert can be deformed to form to the structural arrangement of an implant component and permanently attached to the implant component. In an additional example, a metal tab can be provided over the insert articulating surface and a fastener (e.g., screw) can be introduced through the tab and the insert to prevent, or substantially prevent, the insert from becoming free of an implant component after implantation. In yet another example, an insert can be attached to an implant component using a fastener (e.g., screw) that passes through a portion, or the entirety, of the insert and the implant component, and optionally to the implant site. Subsequent to implantation, a first insert is adapted to be exchanged with a second insert by removing the first insert and introducing the second insert, as described herein.

While insert 106 has been described as having a particular structural arrangement, the insert of an implant system can have any suitable structural arrangement that accomplishes attachment between the insert and a first implant component and provides articulation between the insert and a second implant component. Skilled artisans will be able to select a suitable structural arrangement for the insert of an implant system according to a particular embodiment based on various considerations, including the structural arrangement of a first implant component and/or second implant component. For example, an insert can be adapted to extend the entire length of an implant component from the implant component proximal end to the implant component distal end.

Insert base surface 174 and insert articulating surface 176 can have any suitable radius of curvature and insert 106 can have any suitable dimensions, and skilled artisans will be able to select a suitable radius of curvature for a base surface and insert articulating surface of an insert and/or suitable dimensions for an insert according to a particular embodiment based on various considerations, including the structural arrangement at a desired implant site. For example, one or more inserts can be provided in a kit such that one, two, at least two, or a plurality of the inserts has/have a different radius of curvature on a base surface and/or an insert articulating surface and/or different dimensions. It is considered advantageous to provide a variety of differently sized inserts at least because this provides a mechanism for matching an insert with the anatomy of an implant site, a first implant component, and/or second implant component.

While the insert base surface 174 has been described as having a radius of curvature that extends from insert proximal end 160 toward the insert distal end 162 to insert shoulder 172 and insert articulating surface 176 has been described as having a radius of curvature that extends from insert proximal end 160 to insert distal end 162, an insert body can define a radius of curvature along any suitable length of the surface of an insert. Skilled artisans will be able to select a suitable length to define a radius of curvature on the surface of an insert according to a particular embodiment based on various considerations, including the structural configuration of an implant component. Example lengths considered suitable to define a radius of curvature on the surface of an insert include, but are not limited to, from the insert proximal end to the insert distal end, from a location distal to the insert proximal end to the insert distal end, between the insert proximal end and the insert distal end, and from the insert proximal end to a location proximal to the insert distal end.

Implant system 100 can be utilized in any suitable manner and in any suitable location in a body. For example, implant system 100 can be utilized in subtalar joint arthroplasty, such as to modify the posterior facet of the subtalar joint, as illustrated in FIG. 3. Implant system 100 can be implanted using any suitable method and/or approach. When modifying the posterior facet of the subtalar joint, it is considered advantageous to introduce implant system 100 using a lateral and posterior approach at least because this approach provides access to the joint and has limited, or reduced, exposure to vital structures as compared to a medial approach.

Alternative to first implant component 102 being adapted to be attached to the talus 12 and second implant component 104 being adapted to be attached to the calcaneus 14, a first implant component and/or second implant component of an implant system, such as those described herein, can be attached to a talus, navicular, and/or cuboid. Skilled artisans will be able to select a suitable implant component to attach to a talus, navicular, and/or cuboid according to a particular embodiment based on various considerations, including the structural arrangement at a treatment site. Example joints considered suitable to utilize an implant system and/or implant method described herein include, but are not limited to, the subtalar joint, the talonavicular joint, and the calcaneocuboid joint.

Alternative to including an insert 106, an implant system can omit the inclusion of an insert and a first implant component can articulate with a second implant component. For example, when a first implant component and a second implant component are each formed of a metal or ceramic, the first implant component can articulate with the second implant component. This can be accomplished by omitting the structure on the first implant component and/or second implant component that is configured to receive a portion, or the entirety, of an insert (e.g., recess 139).

FIGS. 7, 8, 9, and 10 illustrate a second exemplary surgical implant system 200. Implant system 200 is similar to implant system 100 illustrated in FIGS. 3, 4, 5, and 6, and described above, except as detailed below. Reference numbers in FIGS. 7, 8, 9, and 10 refer to the same structural element or feature referenced by the same number in FIGS. 3, 4, 5, and 6, offset by 100. Thus, implant system 200 comprises a first implant component 202, a second implant component 204, and an insert 206.

In the illustrated embodiment, first implant component 202 includes a plurality of first implant projections 214, a first implant tab 277, and a plurality of fasteners 278. Each projection of the plurality of first implant projections 214 extends outward and away from the first implant surface 216 from a first implant projection first end 224 to a first implant projection second end 226. Alternative to elongate projections 114 as illustrated in FIGS. 3, 4, 5, and 6, each projection of the plurality of projections 214 and has a circular, or substantially circular, cross section along its length from the first implant projection first end 224 to the first implant projection second end 226 and extends from the first implant surface 216 at an angle. In addition, each projection of the plurality of first implant projections 214 defines a first implant projection second end 226 that is pointed.

First implant tab 277 comprises a first implant tab wall 279 that defines a plurality of first implant bores 280. First implant tab 277 extends outward and away from first implant surface 216 at an angle and along a portion of first implant proximal end 208. Each bore of the plurality of first implant bores 280 extends through the first implant tab wall 279 from the first implant proximal end 208 toward the first implant distal end 210 at an acute angle to first implant surface 216 and is adapted to receive a portion of a fastener of the plurality of fasteners 278. Optionally, each bore of the plurality of first implant bores 280, or a portion thereof, can be countersunk or counterbored to allow a fastener to sit flush with, or below, the outer surface of first implant tab 277.

Each fastener of the plurality of fasteners 278 has a fastener first end 281 that is adapted to receive a tool used to install the fastener at an implant site and a fastener second end 282 that is threaded and adapted to be received by a pre-drilled bore at the implant site. Each fastener of the plurality of fasteners 278 is adapted to attach, or assist with attaching, an implant component at an implant site. Thus, a first fastener is disposed through a first bore defined by first implant tab wall 279 and a second fastener is disposed through a second bore defined by first implant tab wall 279. A fastener can be disposed through each bore defined by a first implant tab wall.

While first implant tab 277 has been illustrated and described as extending outward and away from first implant surface 216 and along a portion of first implant proximal end 208, the tab of an implant component can extend from any suitable portion of an implant component and along any suitable length of an implant component. Skilled artisans will be able to select a suitable location to position a tab and a suitable length for a tab according to a particular embodiment based on various considerations, including the structural arrangement at a desired implant component. Example locations considered suitable to position a tab include, but are not limited to, along the first implant proximal end of a first implant component, and on the first implant surface of a first implant component. Example lengths considered suitable for a tab include, but are not limited to, a length equal to, or substantially equal to, the length of the first implant proximal end of a first implant component, a length that is less than the length of the first implant proximal end of a first implant component, and a length that is greater than the length of the first implant proximal end of a first implant component.

While each bore of the plurality of first implant bores 280 has been illustrated and described as extending through the first implant tab wall 279 from the first implant proximal end 208 toward the first implant distal end 210 at an acute angle to first implant surface 216, a bore of a first implant component can extend at any suitable angle to the first implant surface of a first implant component. Skilled artisans will be able to select a suitable angle to define a bore according to a particular embodiment based on various considerations, including the structural arrangement of an implant site. Example angles considered suitable to define a bore on the tab of a first implant component include, but are not limited to, at an angle that is acute to the first implant surface of a first implant component, at an angle that is obtuse to the first implant surface of a first implant component, and defining a bore such that it extends parallel, or substantially parallel, to the first implant surface of the a implant component.

While a plurality of first implant bores 280 has been illustrated and described, the wall of a tab can define any suitable number of bores having any suitable diameter, and skilled artisans will be able to select a suitable number of bores for inclusion in a tab and a suitable diameter for each bore according to a particular embodiment based on various considerations, including the structural configuration at an implant site. Example number of bores considered suitable include, but are not limited to, one, at least one, two, three, four, a plurality, and any other number considered suitable for a particular application. An example diameter considered suitable for a bore includes, but is not limited to, a diameter that is capable of receiving a fastener.

In the illustrated embodiment, second implant component 204 includes a plurality of second implant projections 236, a second implant tab 283, and a plurality of fasteners 278. Each projection of the plurality of second implant projections 236 extends outward and away from the second implant surface 238 from a second implant projection first end 254 to a second implant projection second end 256. Alternative to elongate projections 136 as illustrated in FIGS. 3, 4, 5, and 6, each projection of the plurality of second implant projections 236 has a circular, or substantially circular, cross section along its length from the second implant projection first end 254 to the second implant projection second end 256 and extends from the second implant surface 238 at an angle. In addition, each projection of the plurality of second implant projections 236 defines a second implant projection second end 256 that is pointed.

Second implant tab 283 comprises a second implant tab wall 284 that defines a plurality of second implant bores 285. Second implant tab 283 extends outward and away from the second implant surface 238 away from second implant distal end 232 at an obtuse, or substantially obtuse, angle and along a portion of second implant proximal end 230. Each bore of the plurality of second implant bores 285 extends through the second implant tab wall 284 from the second implant proximal end 230 toward the second implant distal end 232 at an acute angle to second implant surface 238 and is adapted to receive a portion of a fastener of the plurality of fasteners 278. Optionally, each bore of the plurality of second implant bores 285, or a portion thereof, can be countersunk or counterbored to allow a fastener to sit flush with, or below, the outer surface of second implant tab 283. A first fastener is disposed through a first bore defined by second implant tab wall 284 and a second fastener is disposed through a second bore defined by second implant tab wall 284. A fastener can be disposed through each bore defined by a second implant tab wall.

In the illustrated embodiment, each bore of the plurality of first implant bores 280 and each bore of the plurality of second implant bores 285 has a bore axis that extends through its center. Each bore axis of the plurality of first implant bores 280 is disposed on a first plane and each bore axis of the plurality of second implant bores 285 is disposed on a second plane that intersects the first plane at an angle. The first plane and second plane can intersect at any suitable angle, and skilled artisans will be able to select a suitable angle for a first plane and a second plane to intersect according to a particular embodiment based on various considerations, including the structural arrangement at a treatment site. Example angles considered suitable for a first plane and a second plane to intersect include, but are not limited to, an angle between about 1 degree and 90 degrees, an angle between about 90 degrees and about 180 degrees, a 90 degree angle, a substantially 90 degree angle, a 45 degree angle, a substantially 45 degree angle, an acute angle, an obtuse angle, and any other angle considered suitable for a particular application. Alternatively, a first plane that contains each bore axis of a plurality of first implant bores can extend parallel, or substantially parallel, to a second plane that contains each bore axis of a plurality of second implant bores.

While second implant tab 283 has been illustrated and described as extending outward and away from second implant surface 238 and along a portion of second implant proximal end 230, the tab of an implant component can extend from any suitable portion of an implant component and along any suitable length of an implant component. Skilled artisans will be able to select a suitable location to position a tab and a suitable length for a tab according to a particular embodiment based on various considerations, including the structural arrangement at a desired implant site. Example locations considered suitable to position a tab include, but are not limited to, along the second implant proximal end of a second implant component, and on the second implant surface of a second implant component. Example lengths considered suitable for a tab include, but are not limited to, a length equal to, or substantially equal to, the length of the second implant proximal end of a second implant component, a length that is less than the length of the second implant proximal end of a second implant component, and a length that is greater than the length of the second implant proximal end of a second implant component.

While each bore of the plurality of second implant bores 285 has been illustrated and described as extending through the second implant tab wall 284 from the second implant proximal end 230 toward the second implant distal end 232 at an acute angle to second implant surface 238, a bore of a second implant component can extend at any suitable angle to an implant surface of the second implant component. Skilled artisans will be able to select a suitable angle to define a bore according to a particular embodiment based on various considerations, including the structural arrangement at an implant site. Example angles considered suitable to define a bore on a second implant component include, but are not limited to, at an angle that is acute to the second implant surface of a second implant component, at an angle that is obtuse to the second implant surface of a second implant component, and defining a bore such that it extends parallel, or substantially parallel, to the second implant surface of a second implant component.

While a plurality of second implant bores 285 have been illustrated and described, the wall of a tab can define any suitable number of bores having any suitable diameter, and skilled artisans will be able to select a suitable number of bores for inclusion in a tab and a suitable diameter for each bore according to a particular embodiment based on various considerations, including the structural configuration at an implant site. Example number of bores considered suitable include, but are not limited to, one, at least one, two, three, four, a plurality, and any other number considered suitable for a particular application. An example diameter considered suitable for a bore includes, but is not limited to, a diameter that is capable of receiving a fastener.

While a plurality of fasteners 278 have been illustrated and described as providing a secondary method of attachment between the first implant component 202 and the surface at an implant site and/or the second implant component 204 and the surface at an implant site, any suitable number of fasteners and/or any suitable method of attachment can be used to attach an implant component at a desired treatment site. Skilled artisans will be able to select a suitable number of fasteners and/or a suitable method of attachment according to a particular embodiment based on various considerations, including the structural configuration at a desired implant site. Example number of fasteners considered suitable include, but are not limited to, one, at least one, two, three, four, five, six, a plurality, and any other number considered suitable for a particular application. The number of fasteners included can be based on the number of bores defined by a first implant component and/or a second implant component. Example methods of attachment considered suitable between a first implant component and/or a second implant component and the surface at a desired treatment site include, but are not limited to, using an adhesive, plugs, screws, compression screws, locking screws, multi-angle screw, cortical screw, cancellous screw, and any other method of attachment considered suitable for a particular application.

Each projection of the plurality of first implant projections 214 and each projection of the plurality of second implant projections 236 can extend outward and away from an implant surface of an implant component at any suitable angle and have any suitable length. Skilled artisans will be able to select a suitable angle and length for a projection to extend outward and away from an implant surface of an implant component according to a particular embodiment based on various considerations, including the structural arrangement at a desired implant site. Example angles considered suitable for a projection to extend outward and away from an implant surface of an implant component include, but are not limited to, a 90 degree angle, a substantially 90 degree angle, a 45 degree angle, a substantially 45 degree angle, an angle less than 45 degrees, an acute angle, an obtuse angle, an angle such that the projection is normal to the implant surface, an angle such that the projection is substantially normal to the implant surface, and any other angle considered suitable for a particular application. It is considered advantageous for a projection to extend outward and away from a first implant surface and/or second implant surface at least a length that will provide resistance to sliding after implantation and reduces interference during implantation of the component.

While first implant tab 277 has been illustrated and described as extending outward and away from the first implant surface 216 at an angle and second implant tab 283 has been illustrated and described as extending outward and away from second implant surface 238 at an obtuse, or substantially obtuse, angle, an implant tab can extend outward and away from an implant surface of an implant component at any suitable angle and have any suitable length. Skilled artisans will be able to select a suitable angle and length for an implant tab to extend from an implant surface of an implant component according to a particular embodiment based on various considerations, including the structural arrangement of a desired implant site. Example angles considered suitable for a tab to extend outward and away from an implant surface of an implant component include, but are not limited to, a 90 degree angle, a substantially 90 degree angle, an acute angle, an obtuse angle, an angle such that the tab is normal to the first implant surface, an angle such that the tab is substantially normal to the first implant surface, and any other angle considered suitable for a particular application. It is considered advantageous to for first implant tab and/or second implant tab to be dimensioned such that it is adapted to accept the fastener first end of a fastener, or a plurality of fasteners, and provide material around the fastener first end of each fastener at least to prevent fatigue and/or failure.

Each bore of the plurality of first implant bores 280 and/or each bore of the plurality of second implant bores 285 can optionally be adapted to receive a multi-angle screw that can include a locking cap on fastener first end 281. Using a multi-angle screw is considered advantageous at least because it provides a mechanism directing the fastener to a desired location at the treatment site. For example, such that distal cortical fixation can be achieved.

FIGS. 11, 12, 13, and 14 illustrate a third exemplary surgical implant system 300. Implant system 300 is similar to implant system 200 illustrated in FIGS. 7, 8, 9, and 10, and described above, except as detailed below. Reference numbers in FIGS. 11, 12, 13, and 14 refer to the same structural element or feature referenced by the same number in FIGS. 7, 8, 9, and 10, offset by 100. Thus, implant system 300 comprises a first implant component 302, a second implant component 304, and an insert 306.

In the illustrated embodiment, second implant component 304 omits the inclusion of a second implant tab, as illustrated and described with respect to FIGS. 7, 8, 9, and 10, and includes a plurality of second implant projections 336 and second implant body 334 defines a plurality of second implant protuberances 386.

Each projection of the plurality of second implant projections 336 extends outward and away from the second implant surface 338 from a second implant projection first end 354 toward the second implant distal end 332 to a second implant projection second end 356 at an acute angle with respect to implant surface 338. This configuration advantageously allows for placement and implantation of second implant component 304 at a distance from an implant surface that is less than that required when a second implant component includes projections that extend at a 90 degree, or substantially 90 degree, angle and have the same length as the plurality of second implant projections 336 (e.g., second implant component 204). Thus, it is considered advantageous to include a plurality of second implant projections 336 that extend at an angle with respect to second implant surface 338 at least to allow second implant component 304 to be implanted at an angle and to reduce the distance required between the second implant component 304 and an implant surface while second implant component 304 is being introduced.

Second implant body 334 defines the plurality of second implant protuberances 386 between the second implant proximal end 330 and the second implant distal end 332. Each protuberance of the plurality of second implant protuberances 386 extends outward and away from the second implant surface 338 toward the second implant distal end 332 from a protuberance first end 387 to a protuberance second end 388. Each protuberance of the plurality of second implant protuberances 386 extends at an acute, or substantially acute, angle with respect to second implant surface 338. The second implant body 334 defines a passageway 389 through each protuberance of the plurality of second implant protuberances 386 that extends from a first opening defined on recess base 342 to second opening defined on protuberance second end 388. Each passageway 389 provides access for passing a portion of a fastener of the plurality of fasteners 378 through a protuberance of the plurality of second implant protuberances 386 to attach, or assist with attaching, second implant component 304 at an implant site. Optionally, each passageway 389 defined by second implant body 334, or a portion thereof, can be countersunk or counterbored to allow a fastener to sit flush with, or below, the outer surface of recess base 342. Thus, a first fastener is disposed through a first passageway defined by second implant body 334 and a second fastener is disposed through a second passageway defined by second implant body 334. A fastener can be disposed through each passageway defined by a second implant body.

In the illustrated embodiment, each bore of the plurality of first implant bores 380 has a bore axis that extends through its center and each passageway 389 defined by second implant body 334 has a passageway axis that extends through its center. Each bore axis of the plurality of first implant bores 380 is disposed on a first plane and each passageway axis of each passageway 389 defined by second implant body 334 is disposed on a second plane that intersects the first plane at an angle. The first plane and second plane can intersect at any suitable angle, and skilled artisans will be able to select a suitable angle for a first plane and a second plane to intersect according to a particular embodiment based on various considerations, including the structural arrangement at a treatment site. Example angles considered suitable for a first plane and a second plane to intersect include, but are not limited to, an angle between about 1 degree and 90 degrees, an angle between about 90 degrees and about 180 degrees, a 90 degree angle, a substantially 90 degree angle, a 45 degree angle, a substantially 45 degree angle, an acute angle, an obtuse angle, and any other angle considered suitable for a particular application. Alternatively, a first plane that contains each bore axis of a plurality of first implant bores can extend parallel, or substantially parallel, to a second plane that contains each passageway axis of each passageway defined by a second implant body.

While a plurality of second implant protuberances 386 have been illustrated and described, the body of an implant component can define any suitable number of protuberances, and skilled artisans will be able to select a suitable number of protuberances for inclusion in an implant component according to a particular embodiment based on various considerations, including the structural configuration at an implant site. Example number of protuberances considered suitable include to include in an implant component include, but are not limited to, one, at least one, two, three, four, a plurality, and any other number considered suitable for a particular application.

While each protuberance of the plurality of second implant protuberances 386 has been illustrated and described as extending at an acute angle with respect to second implant surface 338, a protuberance of an implant component can extend at any suitable angle to the implant surface of the implant component. Skilled artisans will be able to select a suitable angle to define a protuberance according to a particular embodiment based on various considerations, including the structural arrangement at an implant site. Example angles considered suitable to define a protuberance on an implant component include, but are not limited to, an angle that is acute to the implant surface of an implant component, an angle that is obtuse to the implant surface of an implant component, and defining a protuberance such that it extends at a 90 degree, or substantially 90 degree, angle to the implant surface of an implant component.

FIGS. 15, 16, 17, and 18 illustrate a fourth exemplary surgical implant system 400. The implant system 400 is similar to implant system 300 illustrated in FIGS. 11, 12, 13, and 14, and described above, except as detailed below. Reference numbers in FIGS. 15, 16, 17, and 18 refer to the same structural element or feature referenced by the same number in FIGS. 11, 12, 13, and 14, offset by 100. Thus, implant system 400 comprises a first implant component 402, a second implant component 404, and an insert 406.

In the illustrated embodiment, the first implant component 402 omits the inclusion of a first implant tab, as illustrated and described with respect to FIGS. 11, 12, 13, and 14, and includes a plurality of first implant projections 414 and a porous first implant surface 416. It is considered advantageous for first implant component 402 to have a porous, or substantially porous, first implant surface 416 at least because this type of surface increases the amount of bone ingrowth between first implant component 402 and the bone at an implant site. The structural configuration of first implant component 402 (e.g., omitting the inclusion of a first implant tab) is considered advantageous at least because it reduces the overall size of first implant component 402 and reduces the complexity of implanting first implant component 402 at a treatment site.

FIGS. 19, 20, 21, and 22 illustrate a fifth exemplary surgical implant system 500. The implant system 500 is similar to implant system 400 illustrated in FIGS. 15, 16, 17, and 18, and described above, except as detailed below. Reference numbers in FIGS. 19, 20, 21, and 22 refer to the same structural element or feature referenced by the same number in FIGS. 15, 16, 17, and 18, offset by 100. Thus, implant system 500 comprises a first implant component 502, a second implant component 504, and an insert 506.

In the illustrated embodiment, first implant component 502 omits the inclusion of the plurality of first implant projections and alternative to having a first implant surface that is convex, or substantially convex, first implant body 512 defines a flat, or substantially flat, first implant surface 516 and an opposably facing concave, or substantially concave, first articulating surface 518. In addition, first implant body 512 defines a plurality of first implant bores 590. Each bore of the plurality of first implant bores 590 extends from a first opening defined on first implant proximal end 508 to a second opening defined on first implant surface 516. Each bore of the plurality of first implant bores 590 provides access for a fastener of the plurality of fasteners 578, such that attachment between first implant component 502 at an implant site can be accomplished. Optionally, each bore of the plurality of first implant bores 590, or a portion thereof, can be countersunk or counterbored to allow a fastener to sit flush with, or below, the outer surface of first implant 502. Thus, a first fastener is disposed through a first bore defined by first implant body 512 and a second fastener is disposed through a second bore defined by first implant body 512. A fastener can be disposed through each bore defined by a first implant body.

In the illustrated embodiment, and alternative to having a second implant surface that is concave, or substantially concave, and a recess base that is convex, or substantially convex, second implant body 534 defines a flat, or substantially flat, second implant surface 538, a recess 539 that has a flat, or substantially flat, recess base 542, and a plurality of recess protuberances 591. In addition, alternative to second implant body defining a plurality of recess projections, second implant body 534 defines a ridge 592 that extends into recess 539. Thus, second implant component 504 comprises a second implant proximal end 530, second implant distal end 532, and a second implant body 534. Second implant body 534 defines recess 539 that extends into second implant body 534 from the second implant proximal end 530 toward the second implant distal end 532 and a ridge 592 that extends into recess 539.

Each protuberance of the plurality of recess protuberances 591 is disposed along the recess length 541 of recess first portion 544 between the second implant proximal end 530 an recess distal end 543 and extends into recess first portion 544. Each protuberance of the plurality of protuberances 591 tapers from the distal end of the protuberance to the proximal end of the protuberance. A first protuberance of the plurality of protuberances 591 is disposed on a first recess side 593 and a second protuberance of the plurality of protuberances 591 is disposed on a second recess side 594. The first recess side 593 is opposite, or substantially opposite, the second recess side 594 across recess 539. Each of the first recess side 593 and second recess side 594 extends from the second implant proximal end 530 to the recess distal end 543.

Recess first portion 544 extends from recess base 542 to ridge 592 and has a recess first portion width 545 along the second implant proximal end 530. Recess second portion 546 has a recess second portion width 547 along the second implant proximal end 530 that is different than recess first portion width 545. In the illustrated embodiment, recess second portion width 547 is less than recess first portion width 545 an amount that is equal to, or substantially equal to, the distance ridge 592 extends into recess 539 on first recess side 593 and second recess side 594.

Ridge 592 extends into recess 539 about the entirety, or a portion of, the perimeter of recess 539. Thus, ridge 592 extends into recess 539 along the first recess side 593, second recess side 594, and recess distal end 543. The structural arrangement of second implant body 534 and recess 539 is considered advantageous at least because it provides a mechanism for releasably attaching an insert, such as insert 506, to second implant component 504.

In the illustrated embodiment, each bore of the plurality of first implant bores 590 has a bore axis that extends through its center and each passageway 589 defined by second implant body 534 has a passageway axis that extends through its center. Each bore axis of the plurality of first implant bores 590 is disposed on a first plane and each passageway axis of each passageway 589 defined by second implant body 534 is disposed on a second plane that intersects the first plane at an angle. The first plane and second plane can intersect at any suitable angle, and skilled artisans will be able to select a suitable angle for a first plane and a second plane to intersect according to a particular embodiment based on various considerations, including the structural arrangement at a treatment site. Example angles considered suitable for a first plane and a second plane to intersect include, but are not limited to, an angle between about 1 degree and 90 degrees, an angle between about 90 degrees and about 180 degrees, a 90 degree angle, a substantially 90 degree angle, a 45 degree angle, a substantially 45 degree angle, an acute angle, an obtuse angle, and any other angle considered suitable for a particular application. Alternatively, a first plane that contains each bore axis of a plurality of first implant bores can extend parallel, or substantially parallel, to a second plane that contains each passageway axis of each passageway defined by a second implant body.

While each protuberance of the plurality of protuberances 591 has been described and illustrated as having a tapered configuration and as being positioned in the recess first portion 544, a protuberance can have any suitable structural configuration and be positioned at any suitable location on an implant component. Skilled artisans will be able to select a suitable structural configuration for a protuberance and a suitable location to position a protuberance on an implant component according to a particular embodiment based on various considerations, including the material forming an insert and/or implant component. Example locations considered suitable to position a protuberance on an implant component include, but are not limited to, along a portion, or the entirety, of the recess first portion of an implant component, along a portion, or the entirety, of the recess second portion of an implant component, and along a portion, or the entirety, of the recess base of an implant component.

In the illustrated embodiment, and alternative to having an insert base surface that is concave, or substantially concave, insert body 564 defines an insert base surface 574 that is flat, or substantially flat, and that is complementary to recess base 542. In addition, insert body 564 defines a plurality of first insert recesses 595 and second insert recess 596. A first recess of the plurality of first insert recesses 595 extends into insert base 566 on an insert first side 597 and a second recess of the plurality of insert recesses 595 extends into insert base 566 on an insert second side 598. Each recess of the plurality of insert recesses 595 is disposed between the insert proximal end 560 and insert distal end 562 and tapers from the distal end of the recess to the proximal end of the recess. Each recess of the plurality of insert recesses 595 is complementary to a protuberance of the plurality of recess protuberances 591. This configuration is considered advantageous at least because it provides a mechanism for releasably attaching insert 506 to second implant component 504.

In addition to defining shoulder 570, insert body 564 defines second insert recess 596 between insert base 566 and insert articulating surface 576. Second insert recess 596 extends along the entirety, or a portion of, insert distal end 562 and complements ridge 592 along the recess distal end 543. Second insert recess 596 extends into insert body 564 a distance that is equal to, or substantially equal to, less than, or greater than, the distance that ridge 592 extends into recess 539. Thus, second insert recess 596 is adapted to interact with ridge 592 of recess 539.

Figure 19:
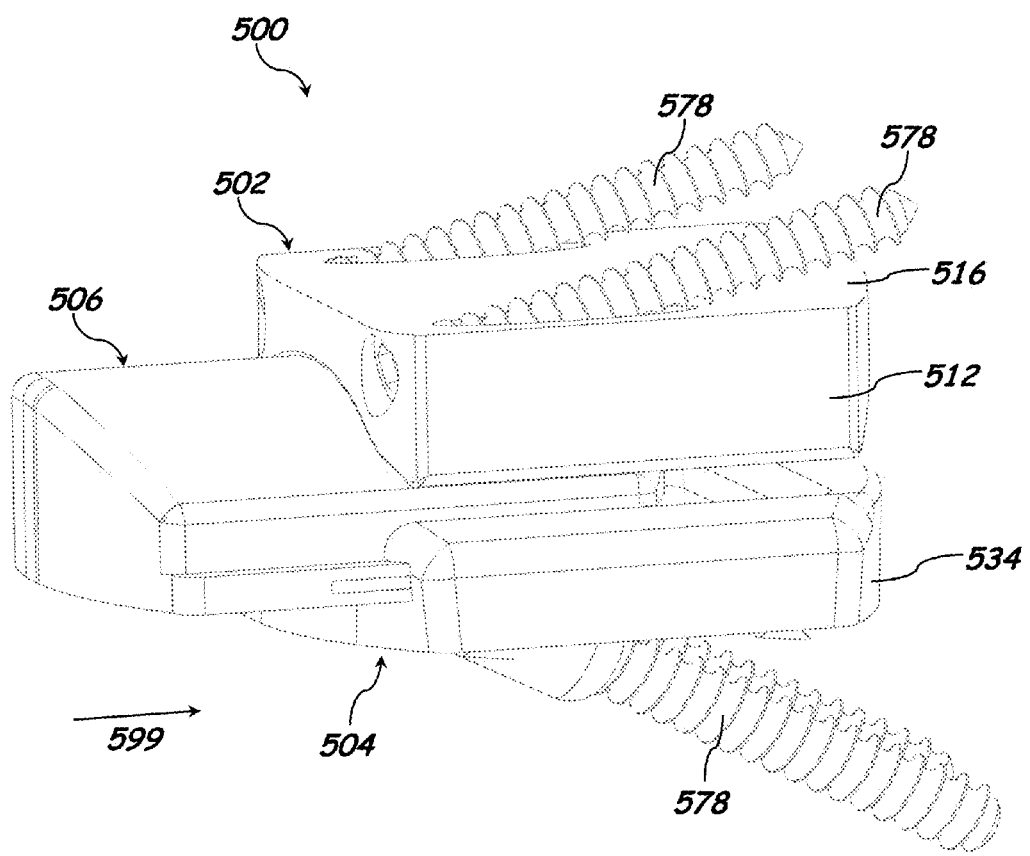
FIG. 19 is a perspective view of a fifth exemplary implant system with the insert partially disposed in the second implant component.
Figure 20:
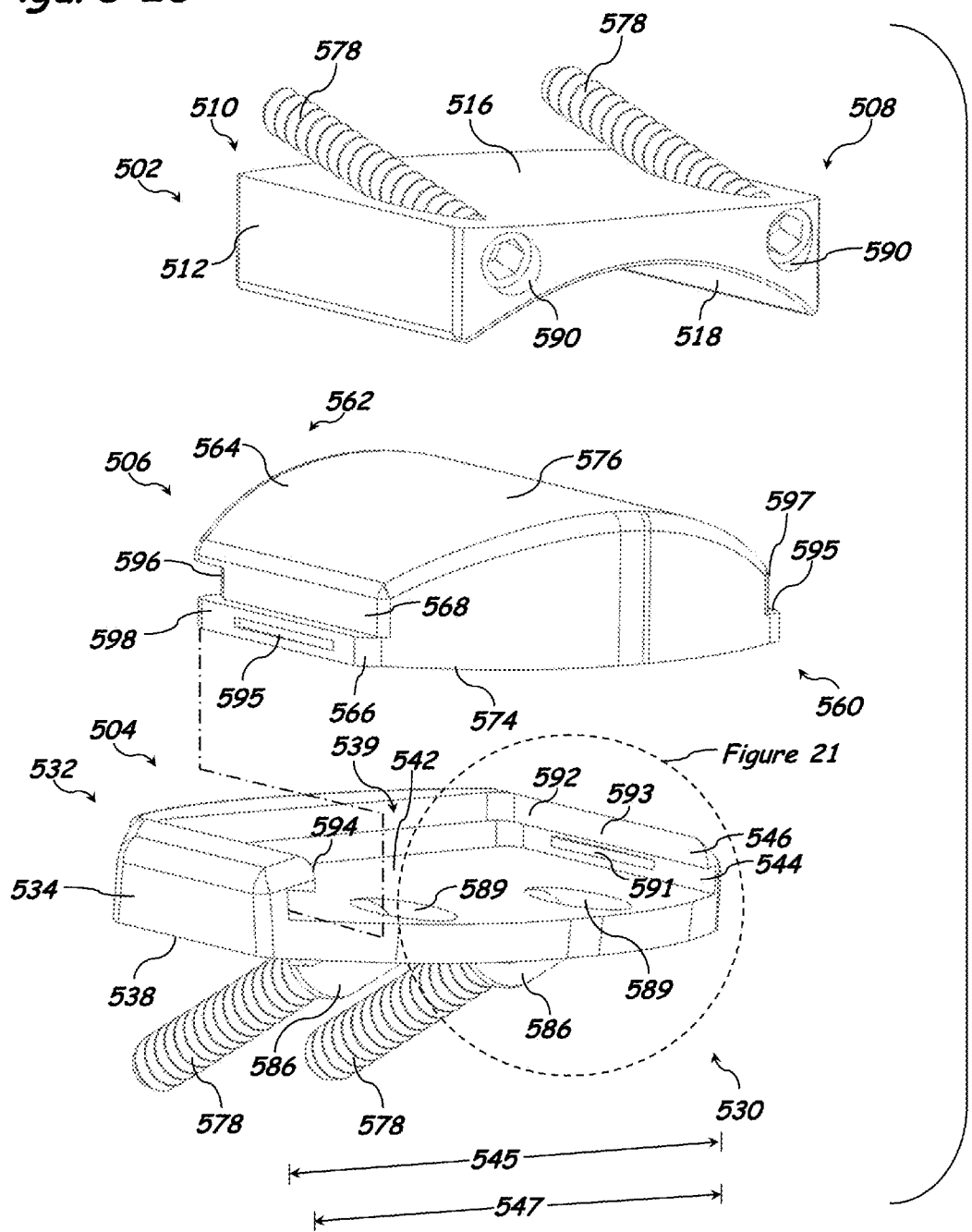
FIG. 20 is an exploded view of the exemplary implant system illustrated in FIG. 19.
Figure 21:
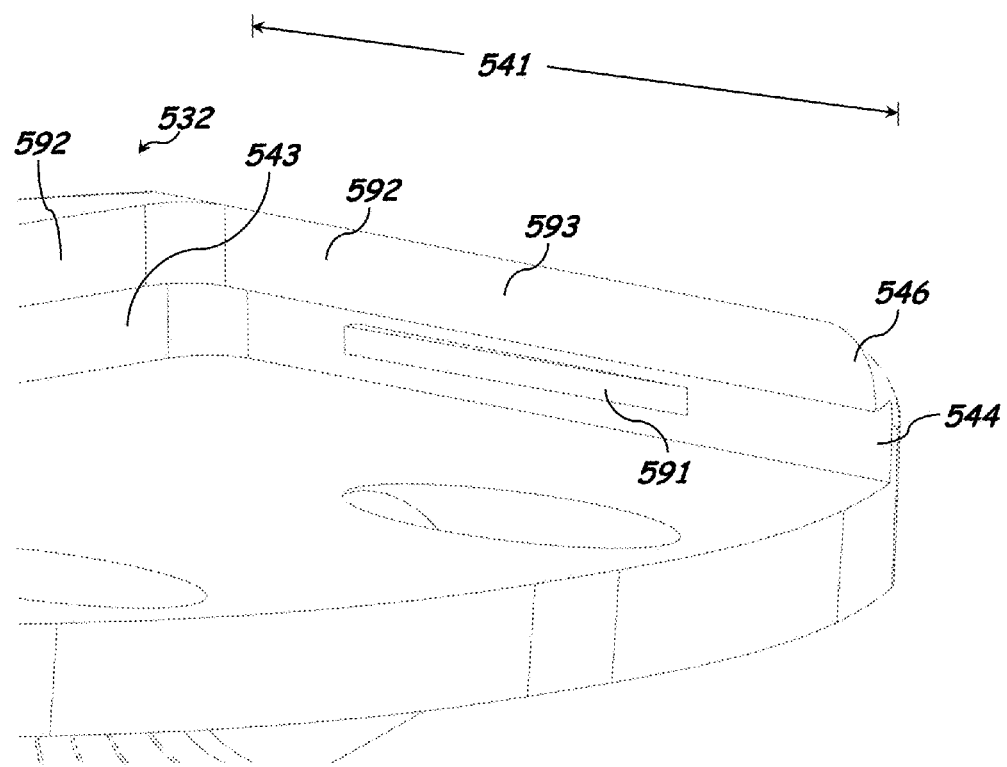
FIG. 21 is a magnified view of the area indicated in FIG. 20.
Figure 22:
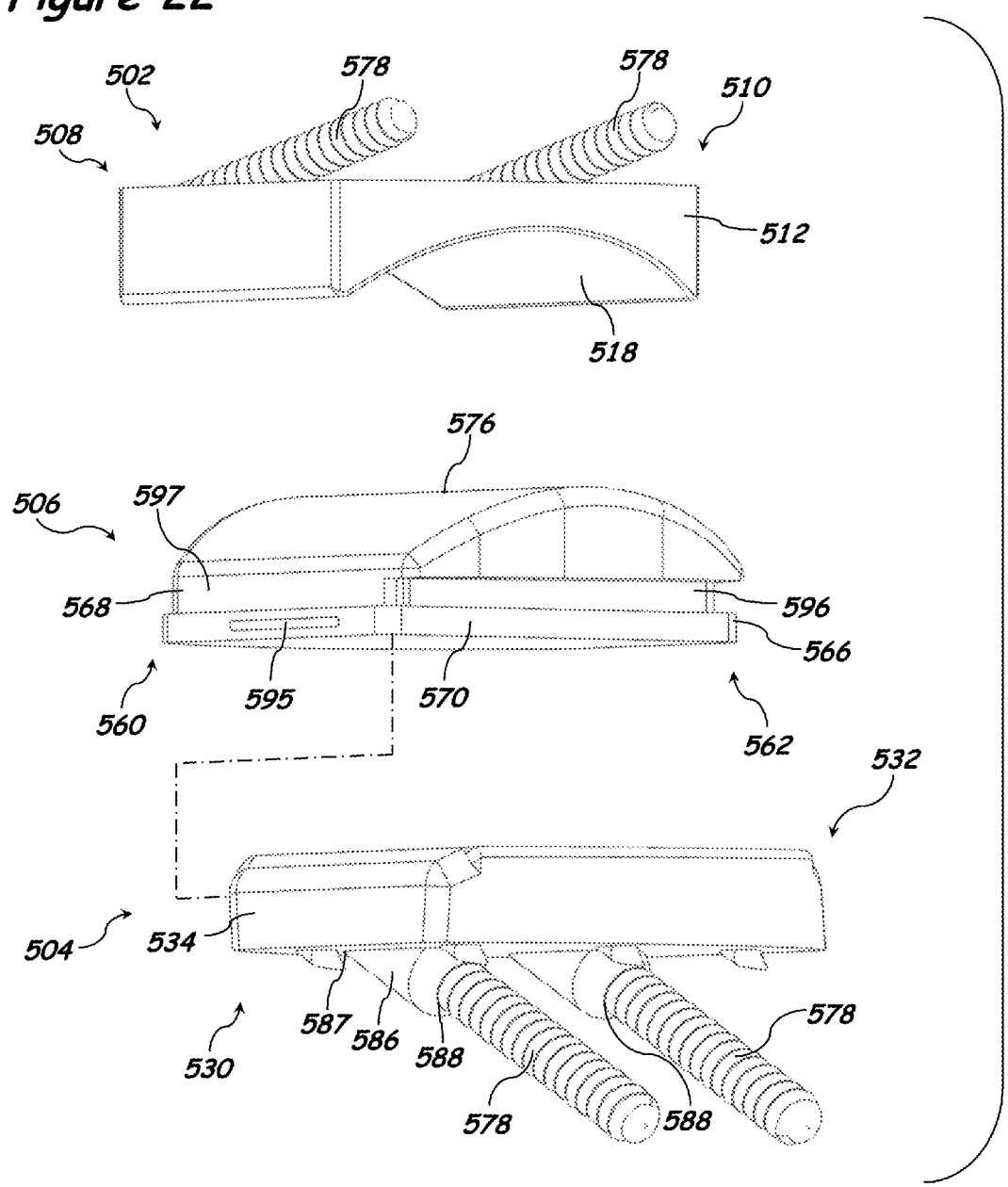
FIG. 22 is another exploded view of the exemplary implant system illustrated in FIG. 19.

In use, as shown in FIG. 19, as distally directed axial movement is placed on insert 506, shown as arrow 599, insert base 566 is inserted into recess first portion 544. As distally directed axial movement continues to be placed on insert 506, a first protuberance of the plurality of protuberances 591 will engage with a first recess of the plurality of first insert recesses 595 to attach insert 506 to second implant component 504.

Figure 23:
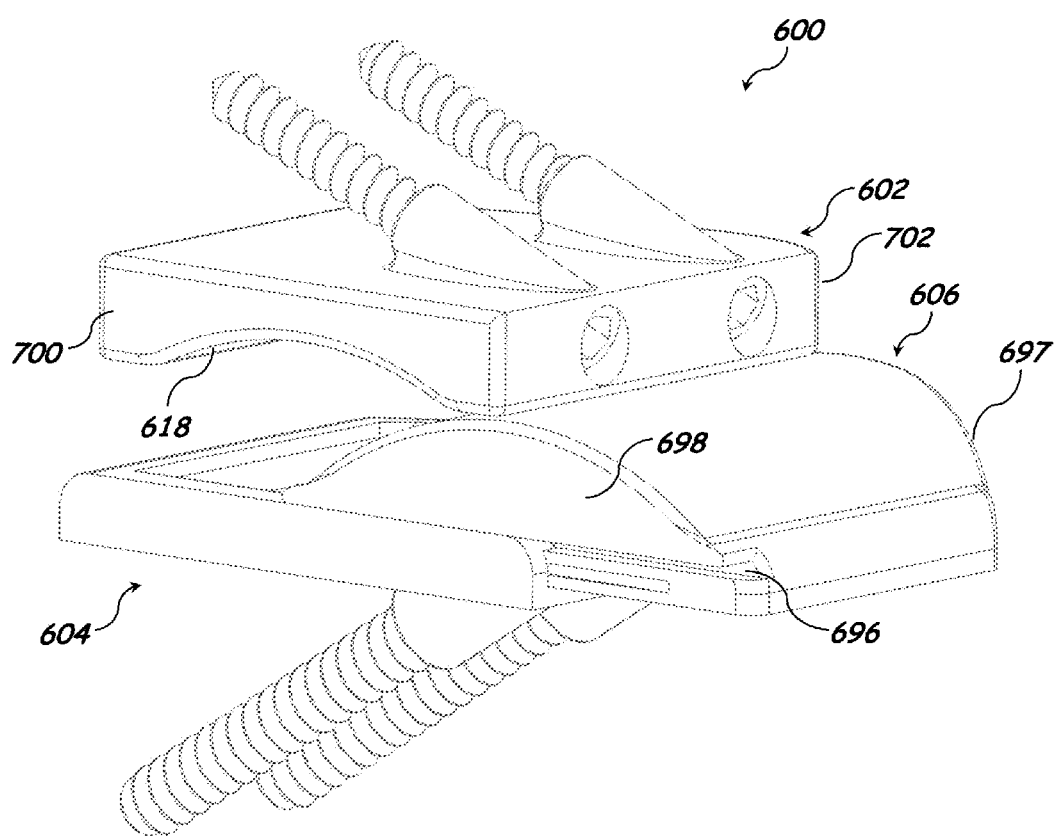
FIG. 23 is a perspective view of a sixth exemplary implant system with the insert partially disposed in the second implant component.
Figure 24:
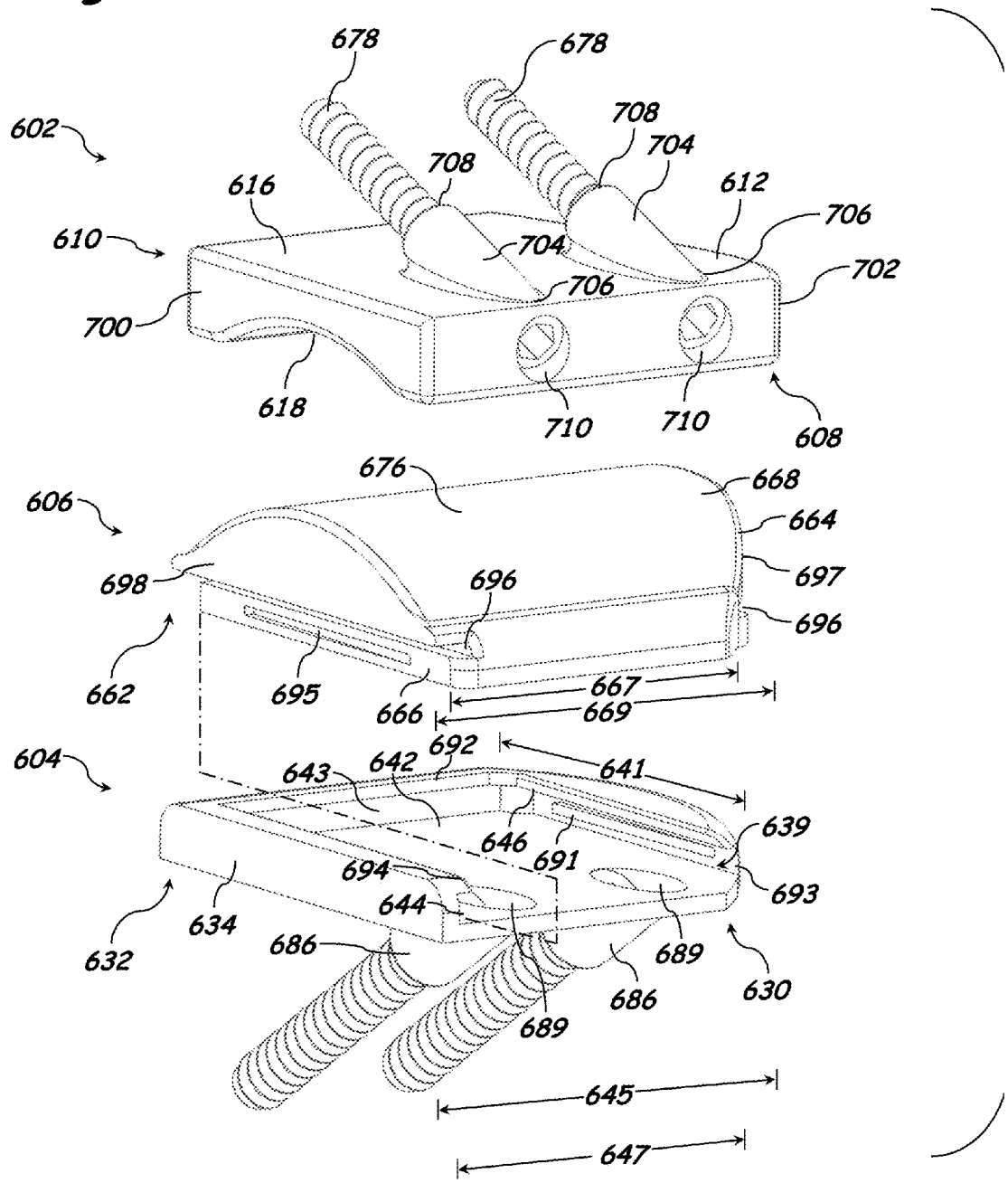
FIG. 24 is an exploded view of the exemplary implant system illustrated in FIG. 23.
Figure 25:
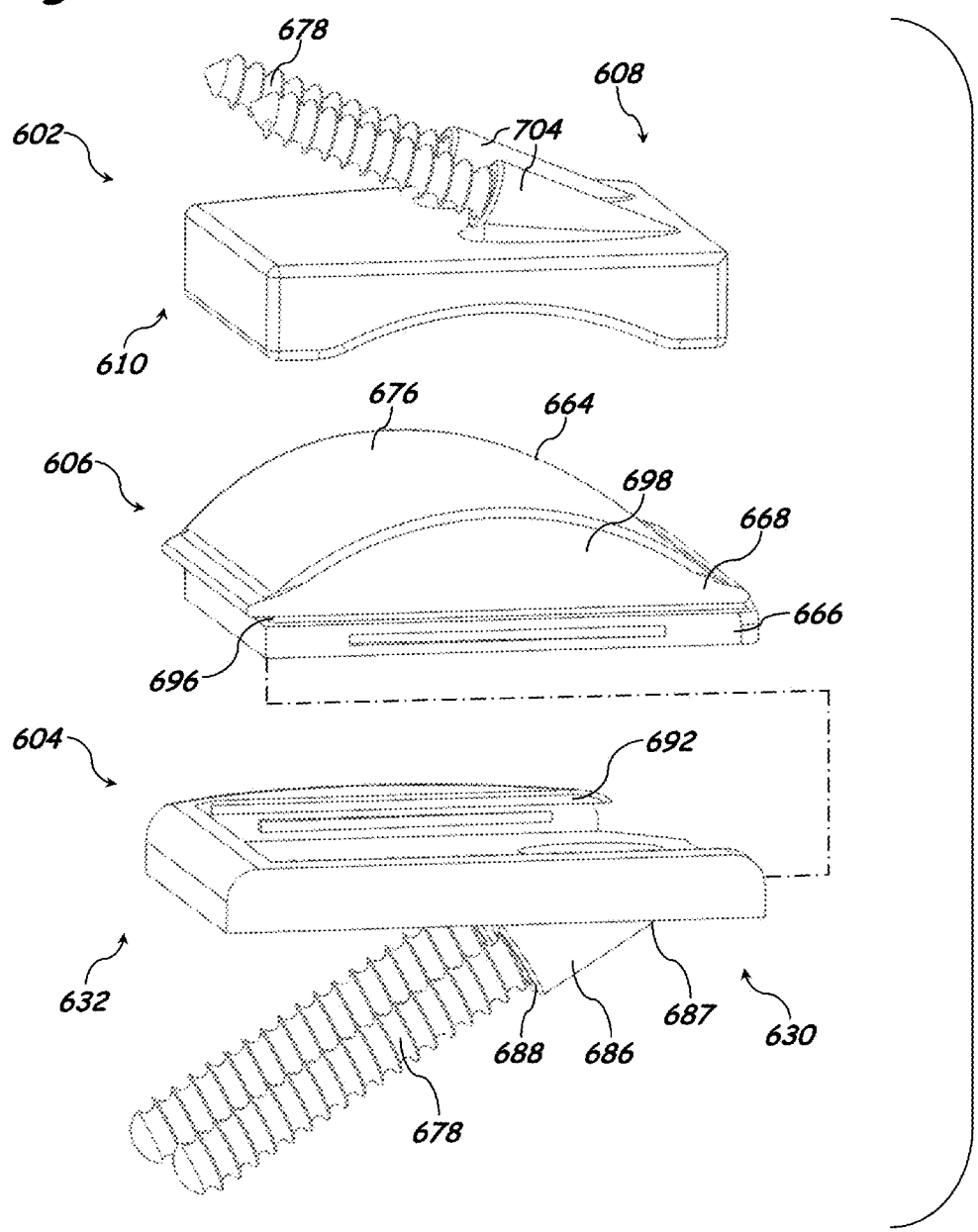
FIG. 25 is another exploded view of the exemplary implant system illustrated in FIG. 23.
Figure 26:
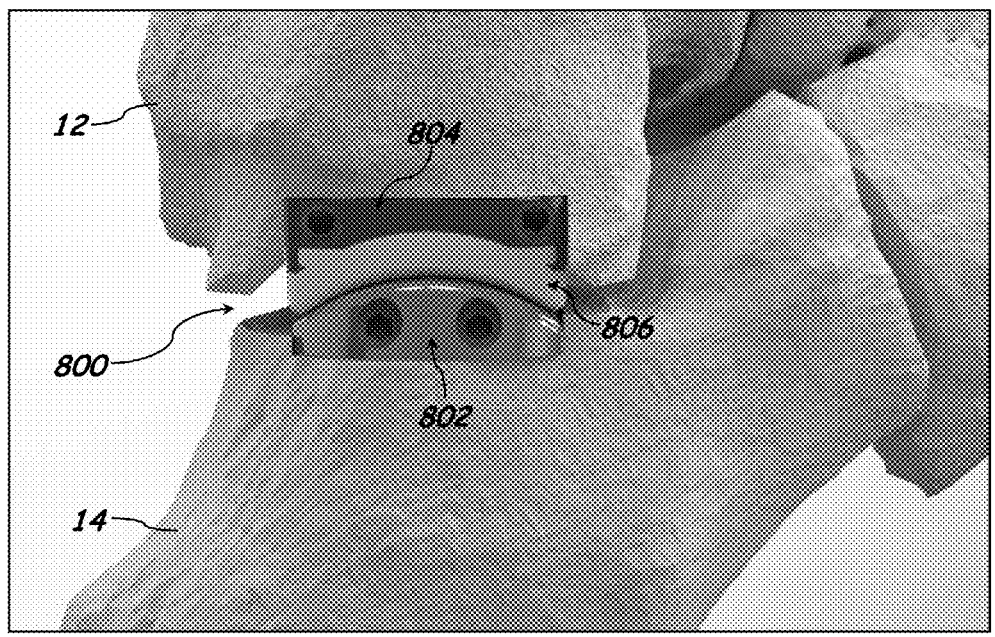
FIG. 26 is a perspective view of a seventh exemplary implant system disposed in the subtalar joint of a human foot.
Figure 27:
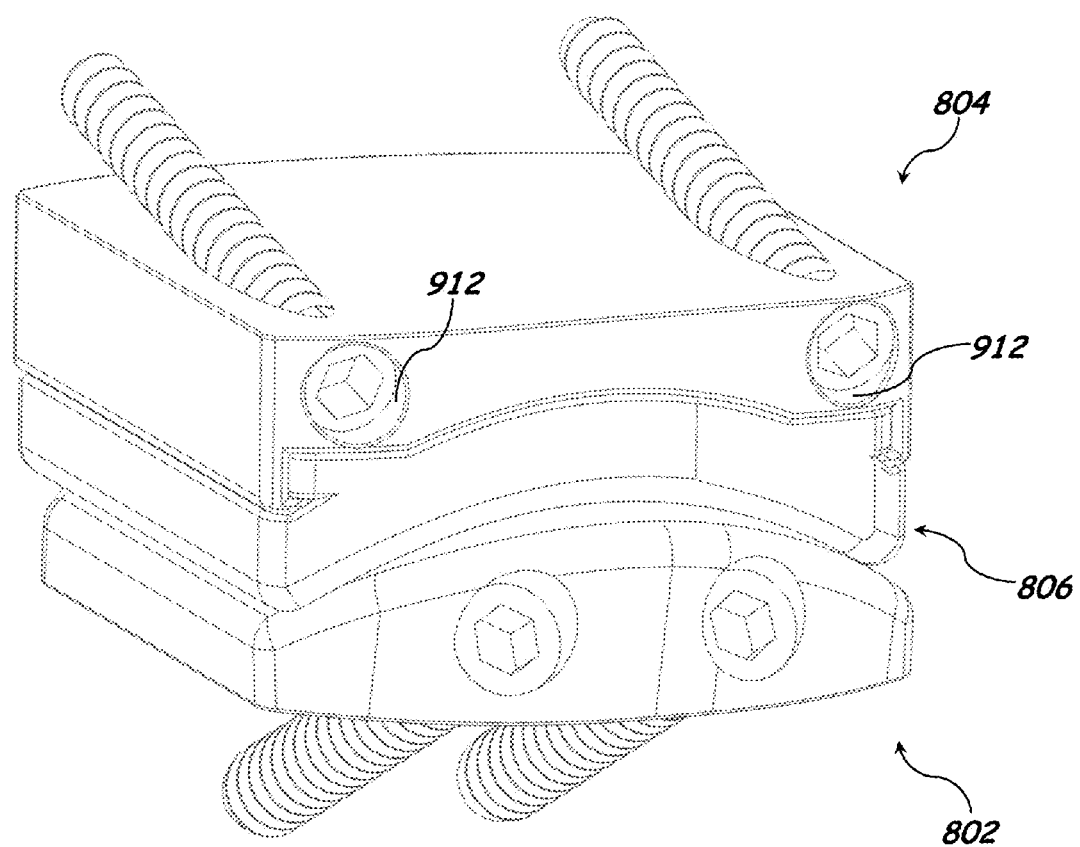
FIG. 27 is a perspective view of the seventh exemplary implant system illustrated in FIG. 26, free of the subtalar joint.
Figure 28:
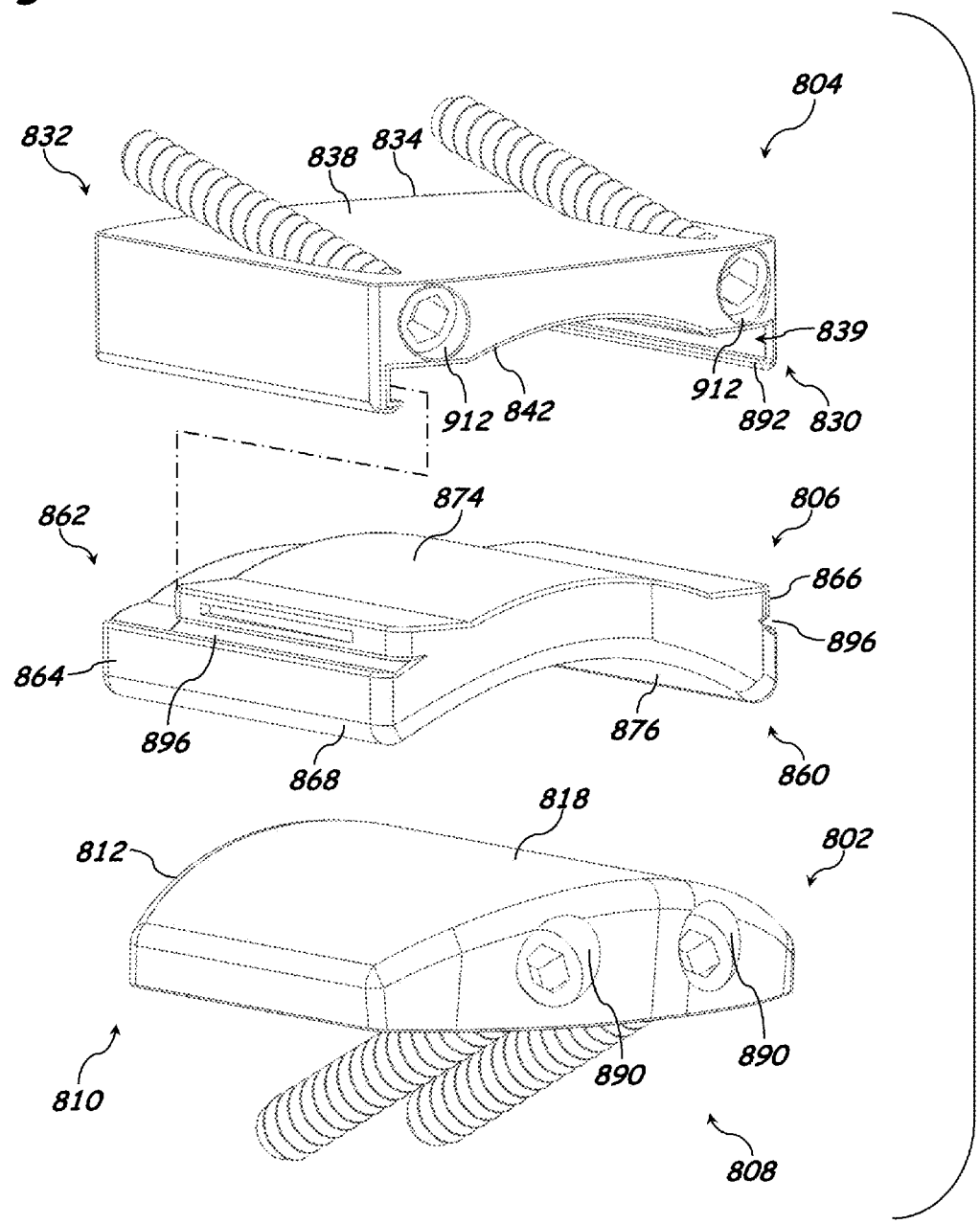
FIG. 28 is an exploded view of the exemplary implant system illustrated in FIG. 27.
Figure 29:
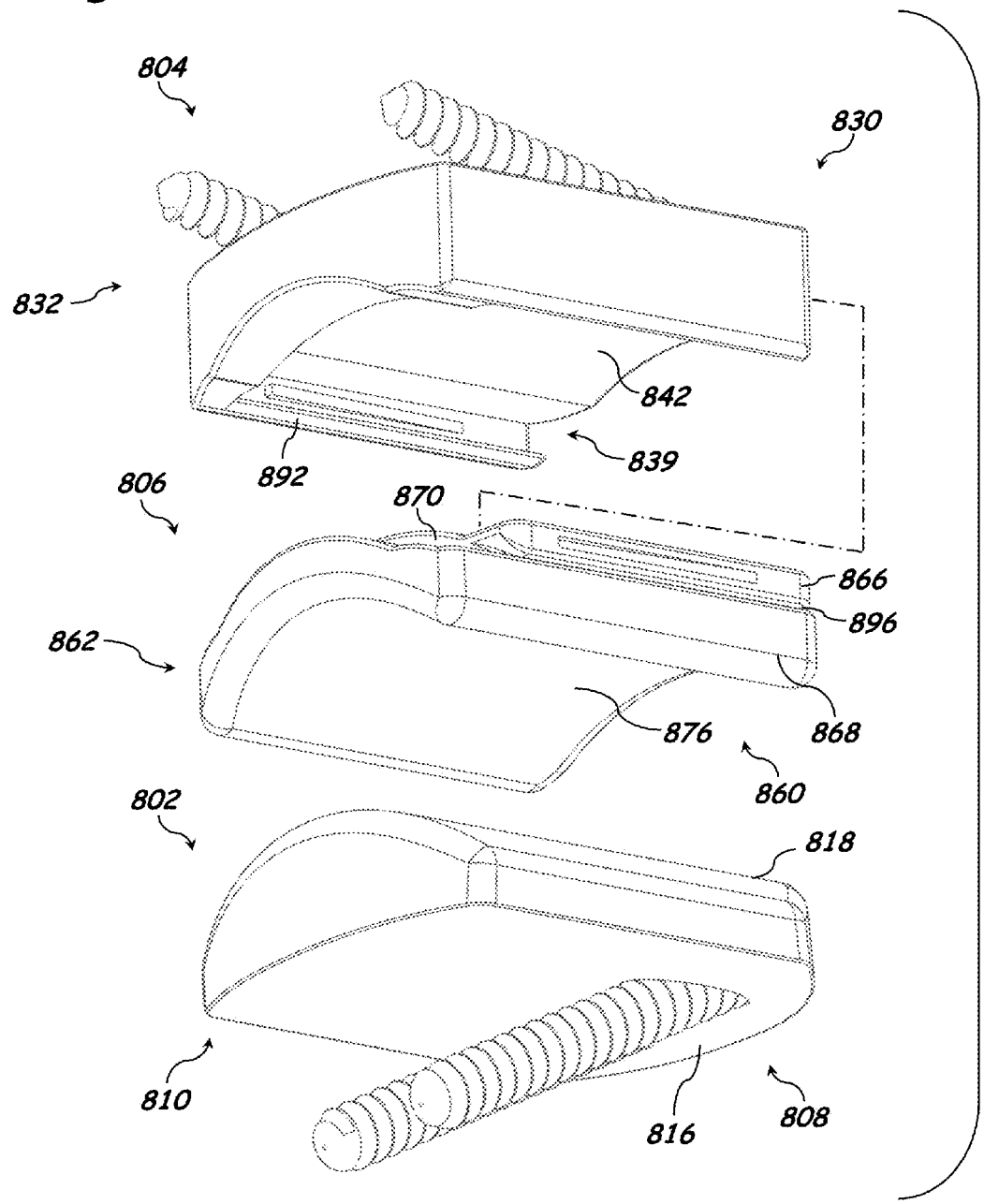
FIG. 29 is another exploded view of the exemplary implant system illustrated in FIG. 27.
Figure 32:
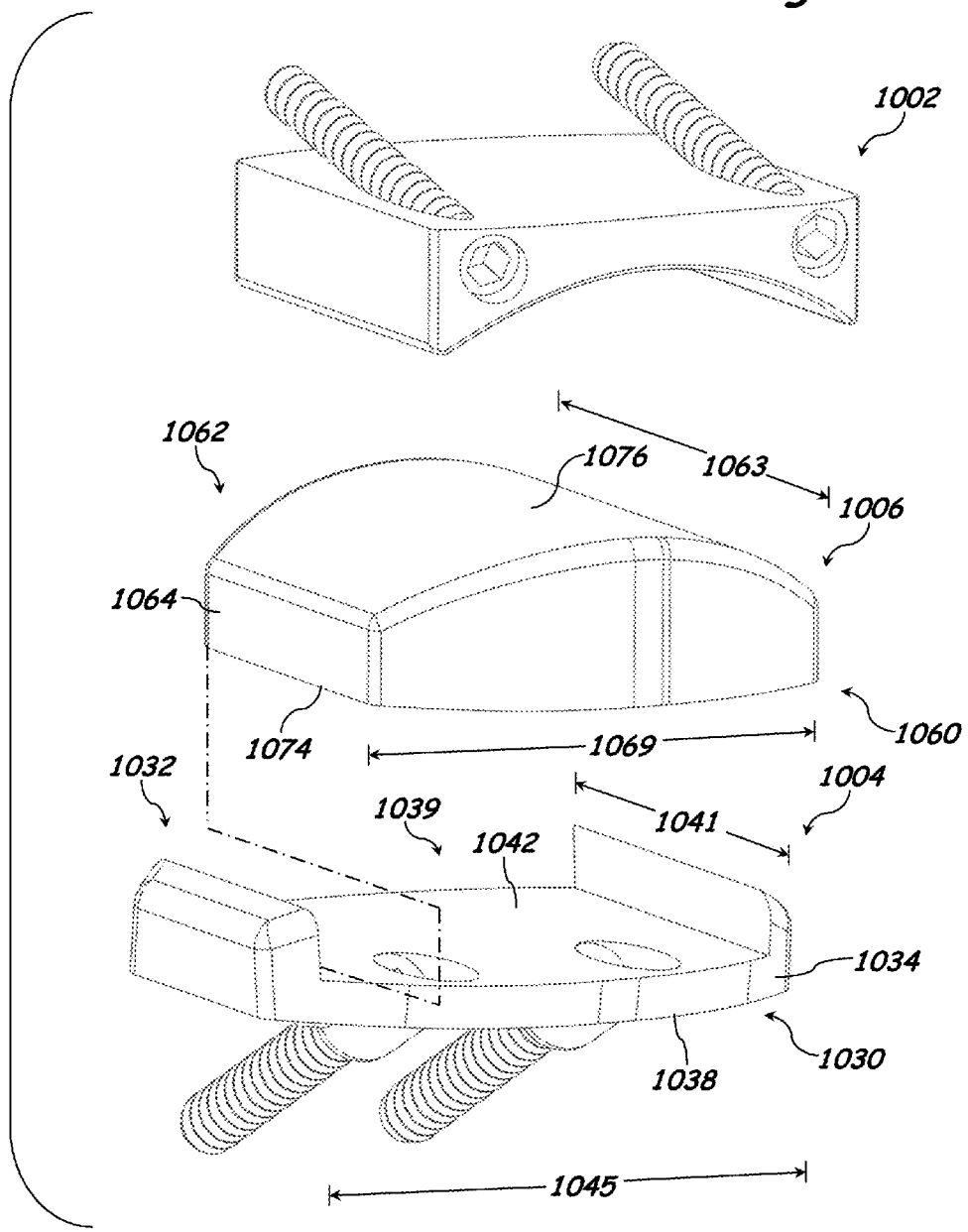
FIG. 32 is an exploded view of the exemplary implant system illustrated in FIG. 31.
Figure 33:
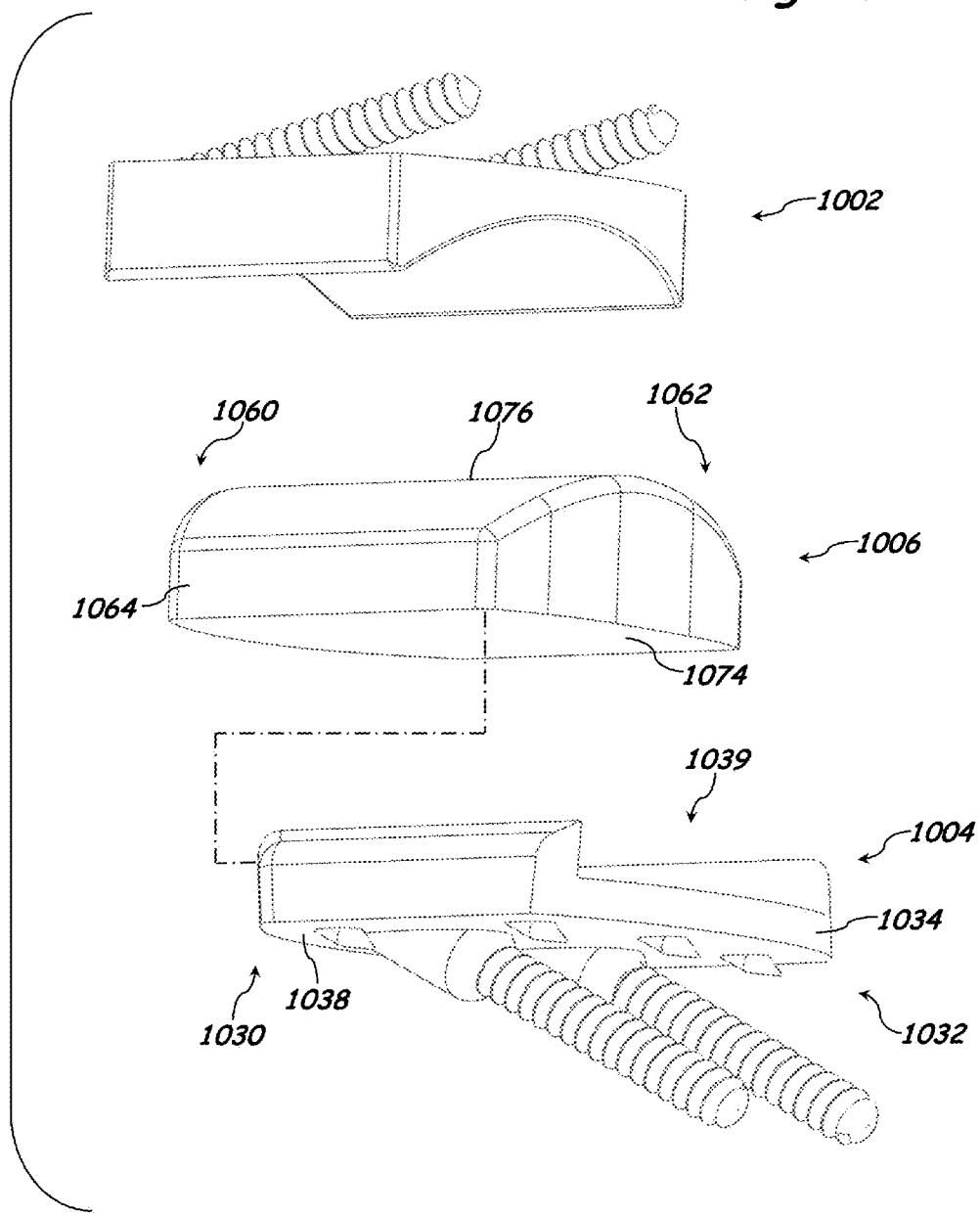
FIG. 33 is another exploded view of the exemplary implant system illustrated in FIG. 31.
Figure 34:
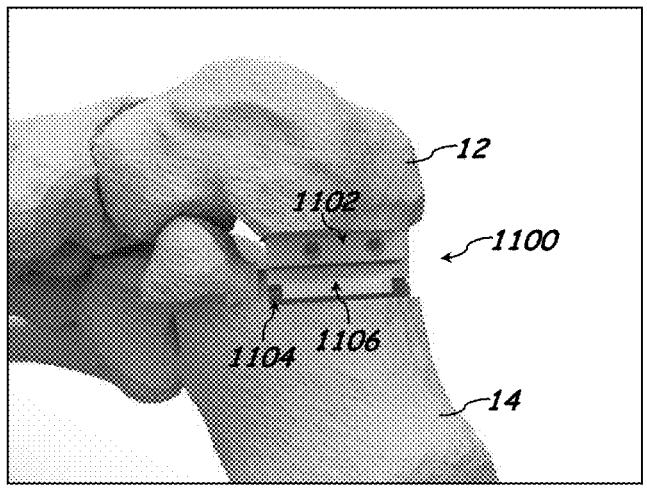
FIG. 34 is a perspective view of a ninth exemplary implant system disposed in the subtalar joint of a human foot.
Figure 35:
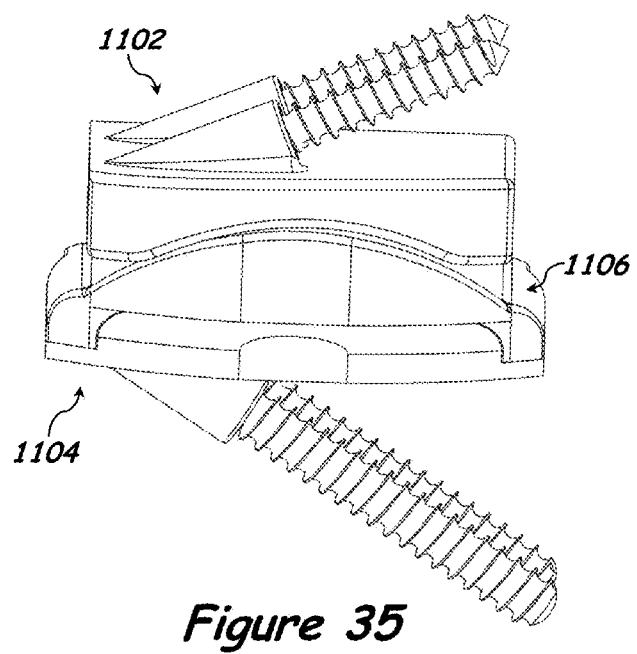
FIG. 35 is a perspective view of the ninth exemplary implant system illustrated in FIG. 34, free of the subtalar joint.
Figure 36:
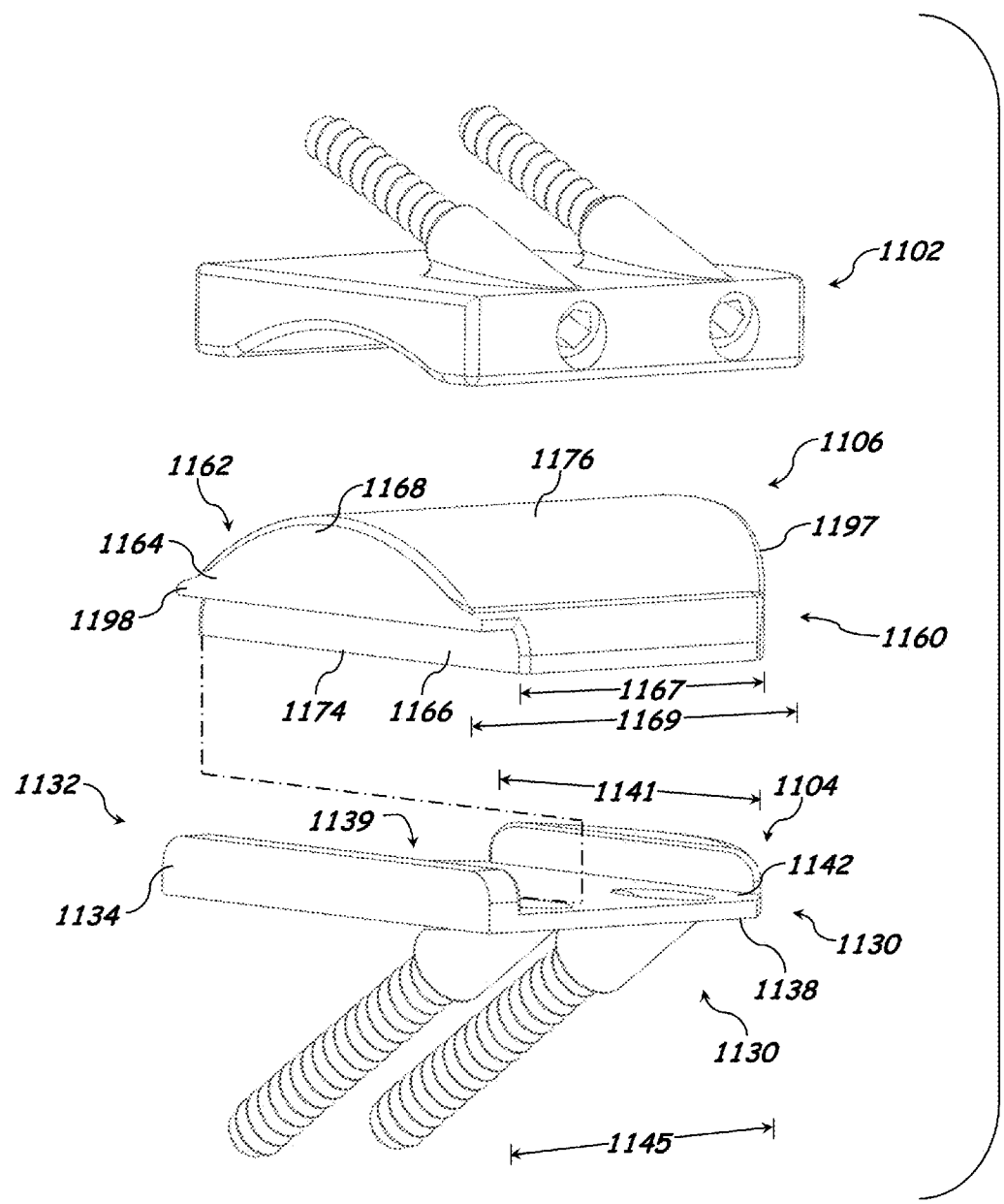
FIG. 36 is an exploded view of the exemplary implant system illustrated in FIG. 35.
Figure 37:
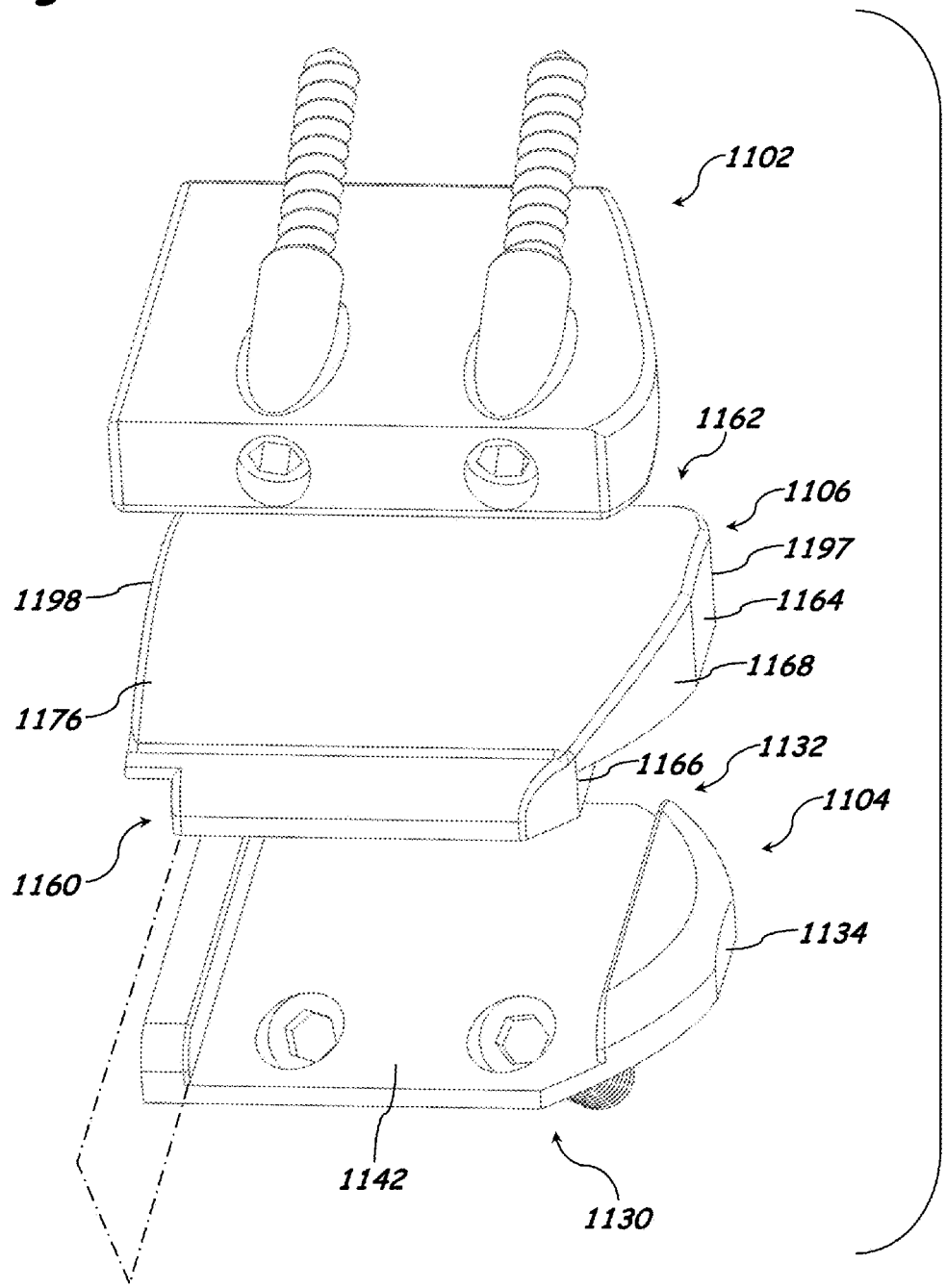
FIG. 37 is another exploded view of the exemplary implant system illustrated in FIG. 35.
Figure 38:
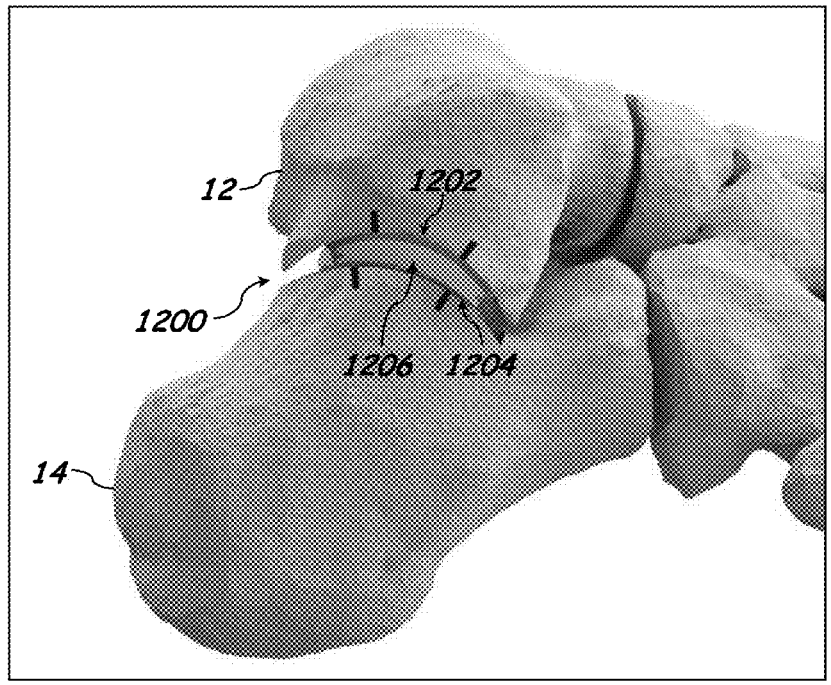
FIG. 38 is a perspective view of a tenth exemplary implant system disposed in the subtalar joint of a human foot.
Figure 39:
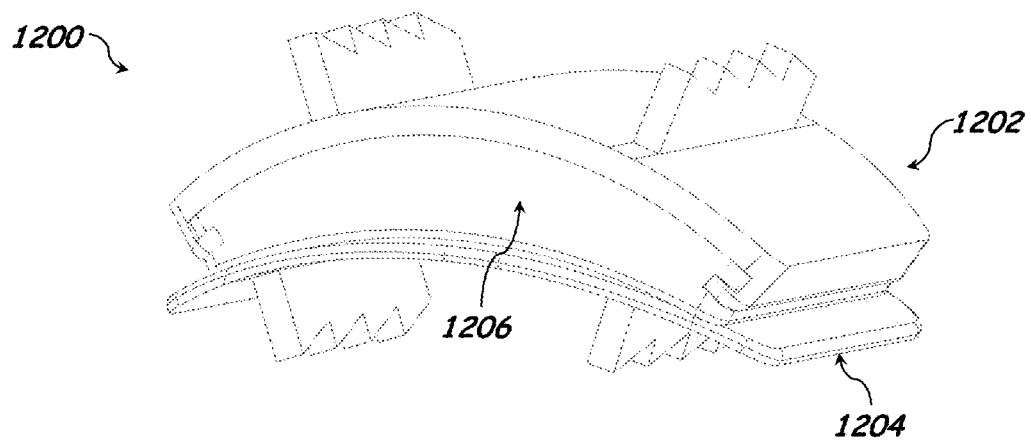
FIG. 39 is a perspective view of the tenth exemplary implant system illustrated in FIG. 38, free of the subtalar joint.
Figure 40:
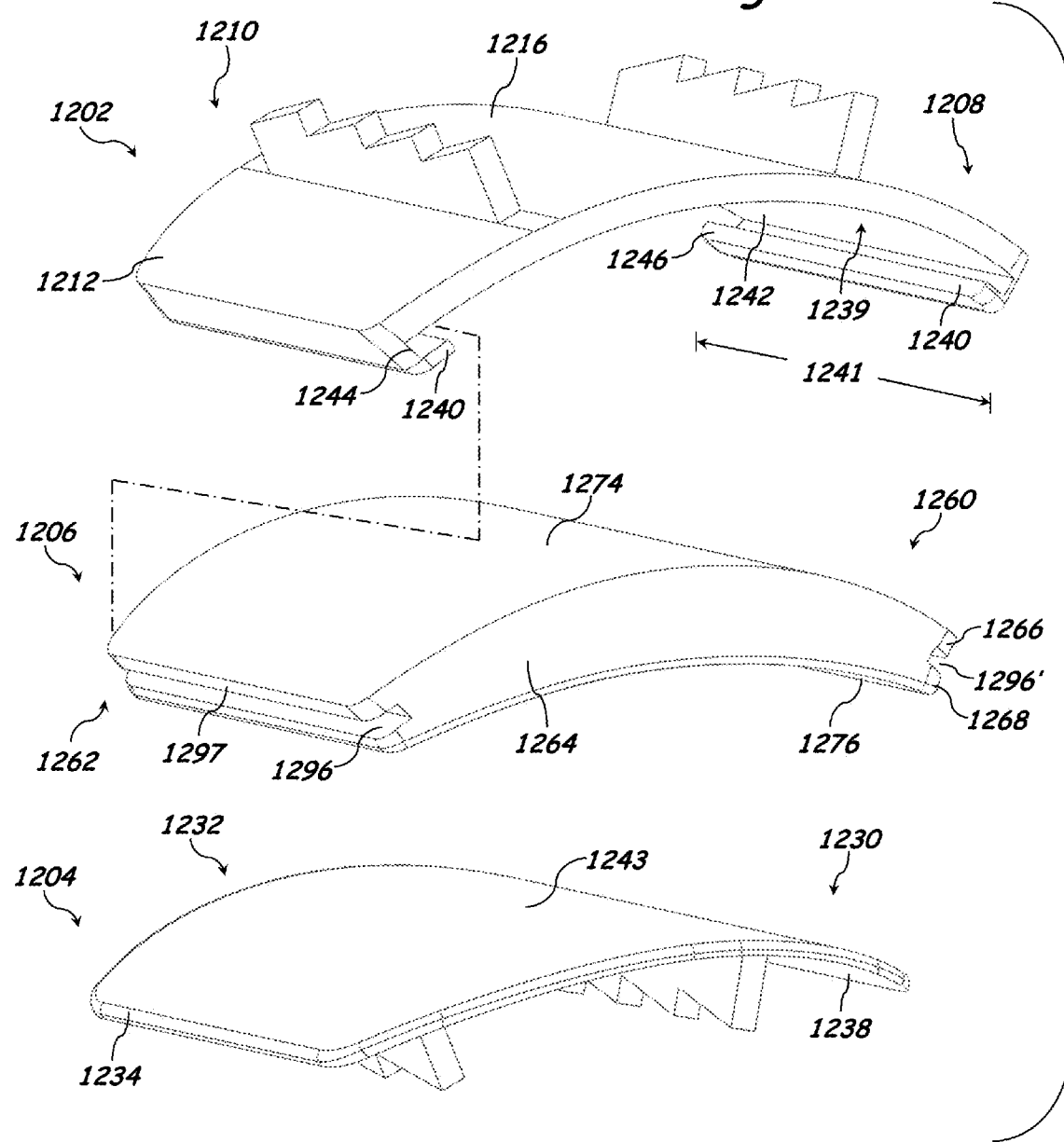
FIG. 40 is an exploded view of the exemplary implant system illustrated in FIG. 39.
Figure 41:
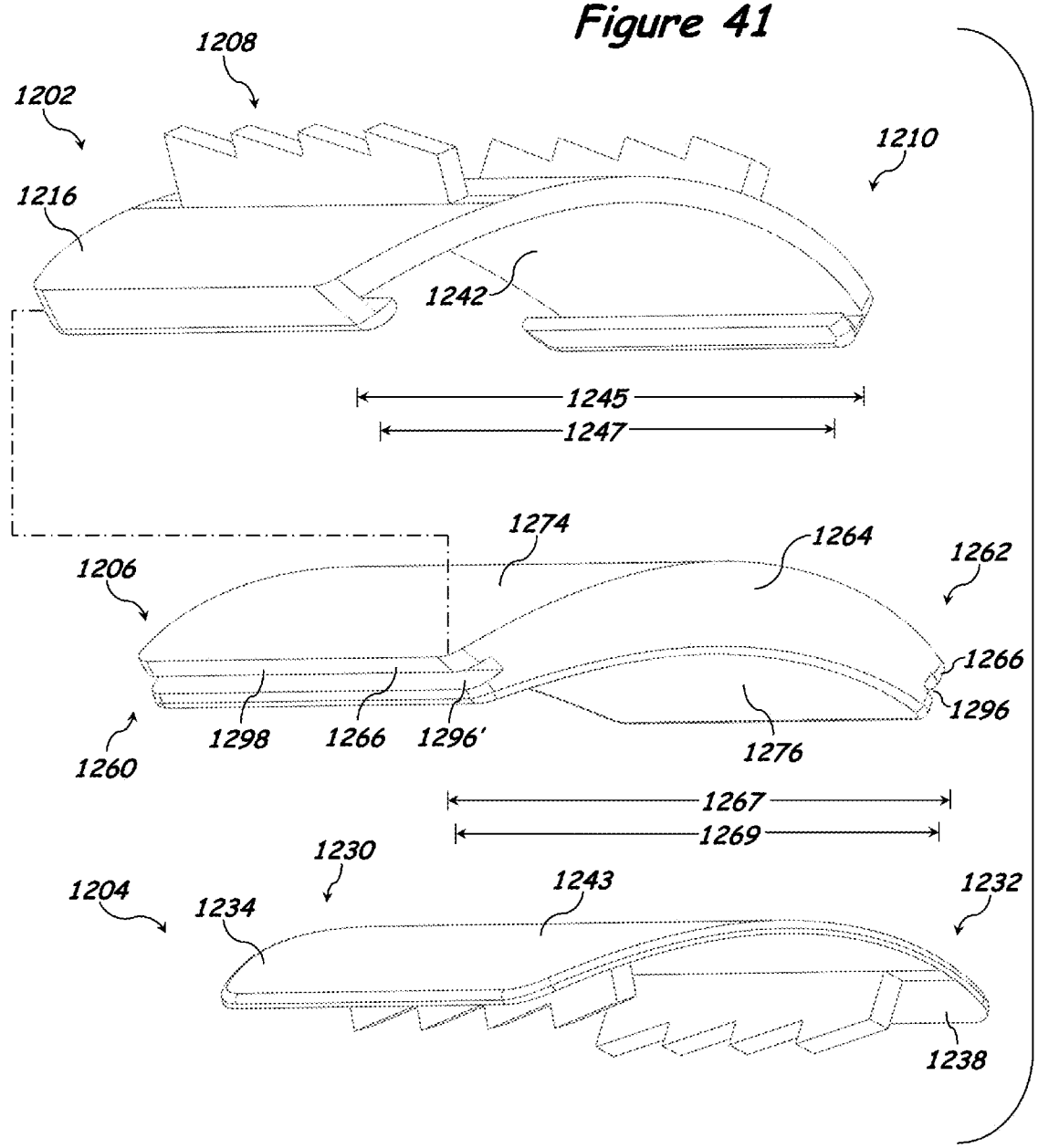
FIG. 41 is another exploded view of the exemplary implant system illustrated in FIG. 39.
Figure 44:
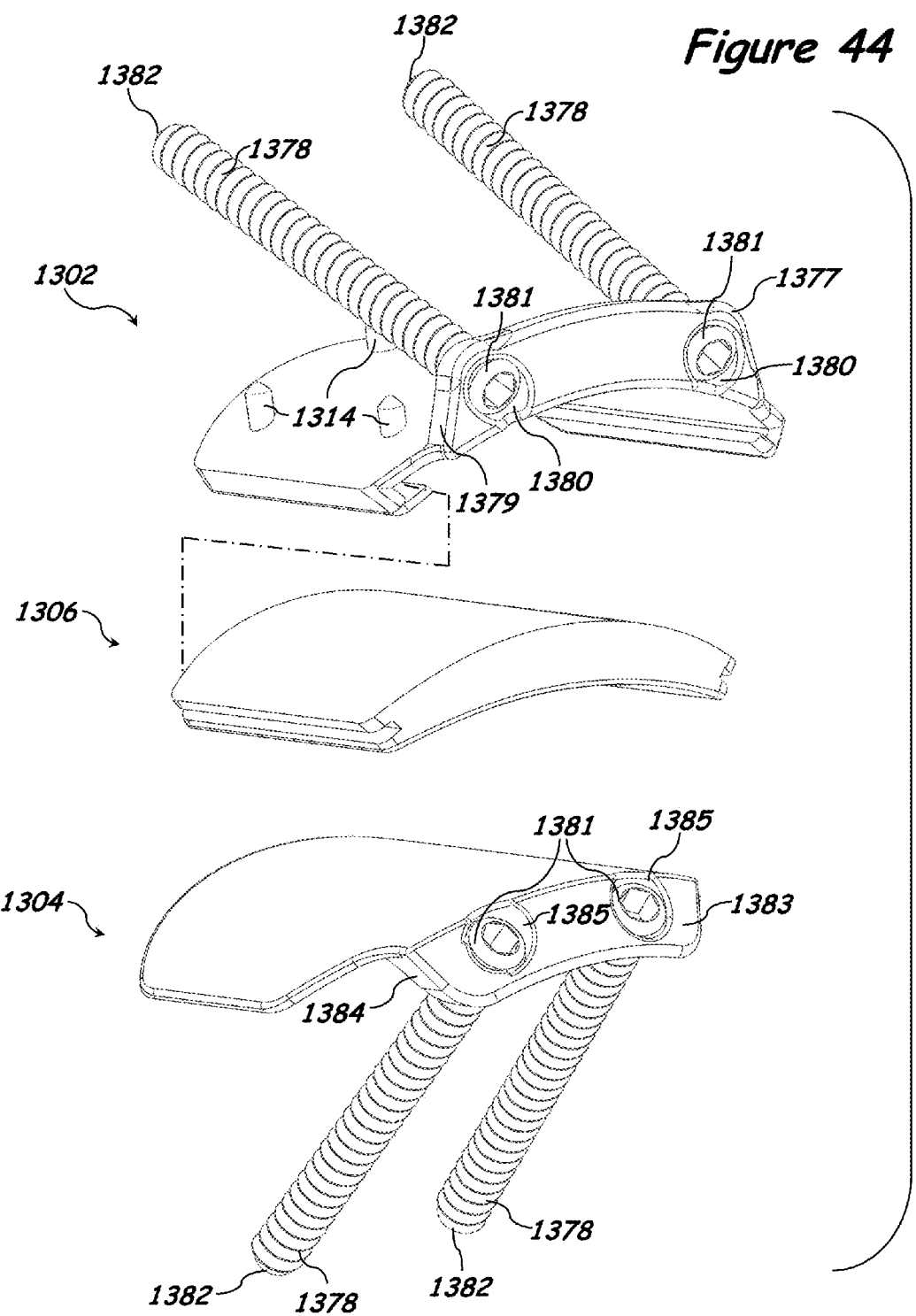
FIG. 44 is an exploded view of the exemplary implant system illustrated in FIG. 43.
Figure 45:
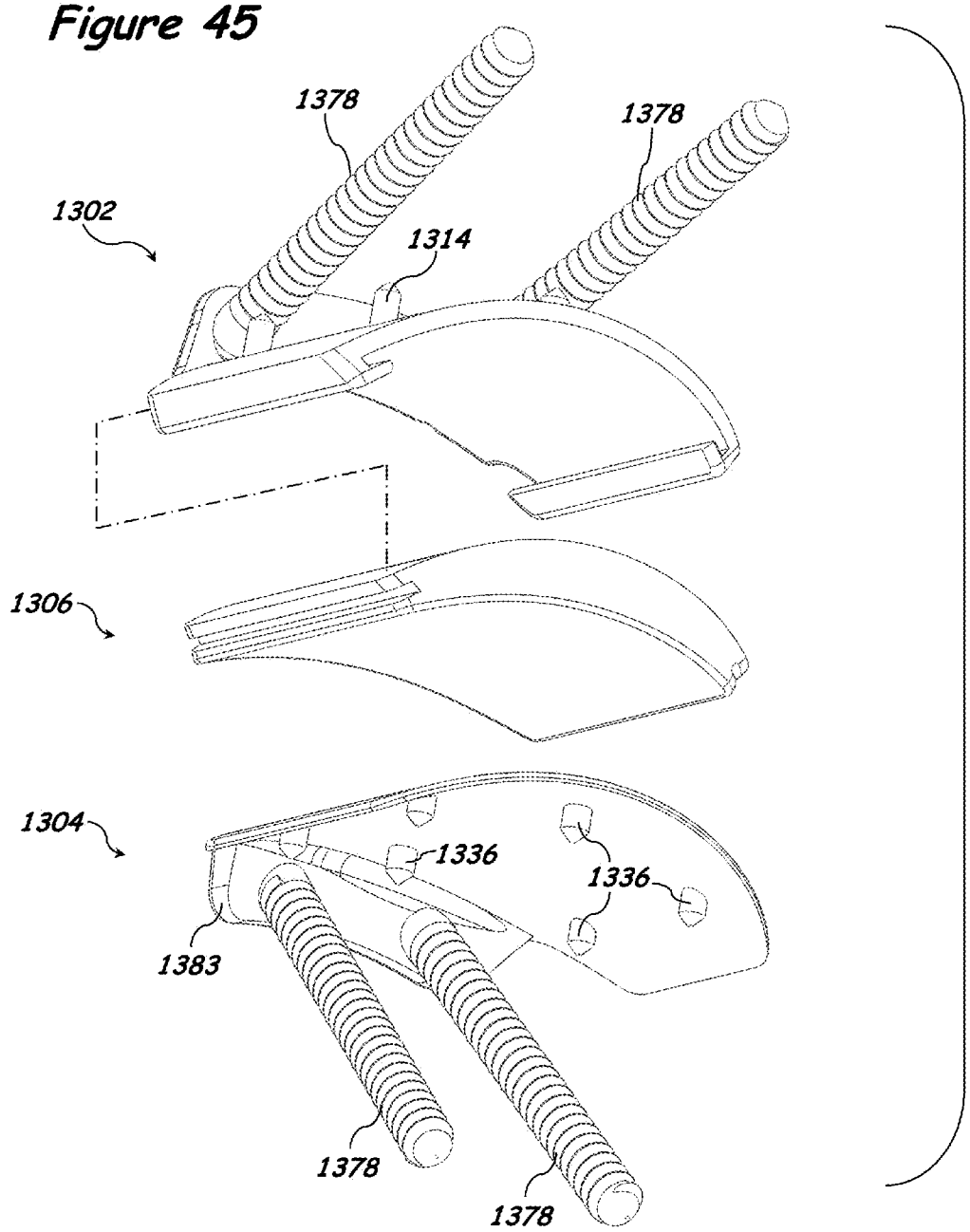
FIG. 45 is another exploded view of the exemplary implant system illustrated in FIG. 43.

FIGS. 23, 24, and 25 illustrate a sixth exemplary surgical implant system 600. The implant system 600 is similar to implant system 500 illustrated in FIGS. 19, 20, 21, and 22, and described above, except as detailed below. Reference numbers in FIGS. 23, 24, and 25 refer to the same structural element or feature referenced by the same number in FIGS. 19, 20, 21, and 22, offset by 100. Thus, implant system 600 comprises a first implant component 602, a second implant component 604, and an insert 606.

Alternative to introducing an implant system using a lateral and posterior approach, as described above, the illustrated embodiment provides an implant system 600 that can be introduced into a body using a medial and posterior approach.

In the illustrated embodiment, alternative to first implant body defining a first articulating surface that extends from the first implant proximal end to the first implant distal end, first implant body 612 defines a first articulating surface 618 that extends from a first implant first side 700 to a first implant second side 702. Each of the first implant first side 700 and first implant second side 702 extends from first implant proximal end 608 to first implant distal end 610.

In the illustrated embodiment, alternative to first implant body defining a plurality of bores that extend through the first implant proximal end and through the first implant surface, first implant body 612 defines a plurality of first implant protuberances 704. Each protuberance of the plurality of first implant protuberances 704 extends outward and away from the first implant surface 616 from a protuberance first end 706 toward first implant distal end 610 to a protuberance second end 708 at an acute, or substantially acute, angle with respect to first implant surface 616. The first implant body 612 defines a passageway 710 through each protuberance of the plurality of first implant protuberances 704 and that extends from a first opening defined on the first implant proximal end 608 to a second opening defined on the protuberance second end 708. Each passageway 710 provides access for passing a fastener of the plurality of fasteners 678 through a protuberance of the plurality of protuberances 704 to attach, or assist with attaching, first implant component 602 at an implant site. Optionally, each passageway 710 defined by first implant body 612, or a portion thereof, can be countersunk or counterbored to allow a fastener to sit flush with, or below, the outer surface of first implant 602. Thus, a first fastener is disposed through a first passageway defined by first implant body 612 and a second fastener is disposed through a second passageway defined by first implant body 612. A fastener can be disposed through each passageway defined by a first implant body.

In the illustrated embodiment, second implant component 604 comprises a second implant proximal end 630, second implant distal end 632, and a second implant body 634. Second implant body 634 defines recess 639 that extends into second implant body 634 from the second implant proximal end 630 toward the second implant distal end 632 and a ridge 692 that extends into recess 639.

In the illustrated embodiment, each passageway 710 defined by first implant body 612 has a passageway axis that extends through its center and each passageway 689 defined by second implant body 634 has a passageway axis that extends through its center. Each passageway axis of each passageway 710 defined by first implant body 612 is disposed on a first plane and each passageway axis of each passageway 689 defined by second implant body 634 is disposed on a second plane that intersects the first plane at an angle. The first plane and second plane can intersect at any suitable angle, and skilled artisans will be able to select a suitable angle for a first plane and a second plane to intersect according to a particular embodiment based on various considerations, including the structural arrangement at a treatment site. Example angles considered suitable for a first plane and a second plane to intersect include, but are not limited to, an angle between about 1 degree and 90 degrees, an angle between about 90 degrees and about 180 degrees, a 90 degree angle, a substantially 90 degree angle, a 45 degree angle, a substantially 45 degree angle, an acute angle, an obtuse angle, and any other angle considered suitable for a particular application. Alternatively, a first plane that contains each passageway axis of each passageway defined by a first implant component can extend parallel, or substantially parallel, to a second plane that contains each passageway axis of each passageway defined by a second implant component.

In the illustrated embodiment, insert 606 comprises an insert proximal end 660, insert distal end 662, and an insert body 664. Alternative to insert body defining an insert articulating surface that has radius of curvature that extends from the insert proximal end to the insert distal end (e.g., FIG. 19, FIG. 20), insert body 664 defines an insert articulating surface 676 that has a radius of curvature that extends from insert first side 697 to insert second side 698.

In addition, insert body 664 defines second insert recess 696 between insert base 666 and insert articulating surface 676. Second insert recess 696 extends along insert first side 697, insert second side 698, and insert distal end 662. Second insert recess 696 extends into insert body 664 a distance that is equal to, or substantially equal to, less than, or greater than, the distance that ridge 692 extends into recess 639. Insert base width 667 is equal to, substantially equal to, less than, or greater than, recess first portion width 645. Insert articulating width 669 is greater than insert base width 667.

While insert articulating width 669 has been described and illustrated as being greater than insert base width 667, the insert articulating portion of an insert can have any suitable width. Skilled artisans will be able to select a suitable width for the articulating portion of an insert according to a particular embodiment based on various considerations, including the structural arrangement at an implant site. Example widths considered suitable include, but are not limited to, an articulating portion that has a width greater than the width of a base portion of an insert, an articulating portion that has a width less than the width of a base portion of an insert, and an articulating portion that has a width equal to, or substantially equal to, than the width of a base portion of an insert.

FIGS. 26, 27, 28, and 29 illustrate a seventh exemplary surgical implant system 800. The implant system 800 is similar to implant system 500 illustrated in FIGS. 19, 20, 21, and 22, and described above, except as detailed below. Reference numbers in FIGS. 26, 27, 28, and 29 refer to the same structural element or feature referenced by the same number in FIGS. 19, 20, 21, and 22, offset by 300. Thus, implant system 800 comprises a first implant component 802, a second implant component 804, and an insert 806.

In the illustrated embodiment, alternative to second implant component being adapted to be attached to the calcaneus, as described above, second implant component 804 is adapted to be attached to the talus 12. Alternative to including a plurality of second implant protuberances and a plurality of second implant projections that extend from second implant surface, second implant body 834 defines a plurality of bores 912 that extend through the second implant proximal end 830 and through the second implant surface 838. Alternative to second implant body defining a recess base that is flat, or substantially flat, second implant body 834 defines a recess 839 having a recess base 842 that is concave, or substantially concave. Optionally, each bore of the plurality of second implant bores 912, or a portion thereof, can be countersunk or counterbored to allow a fastener to sit flush with, or below, the outer surface of second implant 804. Thus, a first fastener is disposed through a first bore defined by second implant body 834 and a second fastener is disposed through a second bore defined by second implant body 834. A fastener can be disposed through each bore defined by a second implant body.

In the illustrated embodiment, alternative to first implant component being adapted to be attached to the talus, as described above, first implant component 802 is adapted to be attached to the calcaneus 14. Alternative to first implant body defining a first articulating surface that is concave, or substantially concave, first implant body 812 defines a first articulating surface 818 that is convex, or substantially convex.

In the illustrated embodiment, each bore of the plurality of first implant bores 890 and each bore of the plurality of second implant bores 912 has a bore axis that extends through its center. Each bore axis of the plurality of first implant bores 890 is disposed on a first plane and each bore axis of the plurality of second implant bores 912 is disposed on a second plane that intersects the first plane at an angle. The first plane and second plane can intersect at any suitable angle, and skilled artisans will be able to select a suitable angle for a first plane and a second plane to intersect according to a particular embodiment based on various considerations, including the structural arrangement at a treatment site. Example angles considered suitable for a first plane and a second plane to intersect include, but are not limited to, an angle between about 1 degree and 90 degrees, an angle between about 90 degrees and about 180 degrees, a 90 degree angle, a substantially 90 degree angle, a 45 degree angle, a substantially 45 degree angle, an acute angle, an obtuse angle, and any other angle considered suitable for a particular application. Alternatively, a first plane that contains each bore axis of a plurality of first implant bores can extend parallel, or substantially parallel, to a second plane that contains each bore axis of a plurality of second implant bores.

In the illustrated embodiment, alternative to insert body defining an insert base surface having a flat, or substantially flat, surface, insert body 864 defines an insert base surface 874 that is convex, or substantially convex, such that it compliments recess base 842. In addition, alternative to insert body defining an insert articulating surface that is convex, or substantially convex, insert body 864 defines an insert articulating surface 876 that is concave, or substantially concave, such that it compliments first articulating surface 818. Insert articulating surface 876 is adapted to articulate with first articulating surface 818.

In addition, alternative to insert body defining an insert second recess that extends along the entirety, or a portion of, the insert distal end (e.g., second insert recess 596), insert body 864 defines a plurality of second insert recesses 896. Each recess of the plurality of second insert recesses 896 is disposed between the insert base surface 874 and insert articulating surface 876 and extends from the insert proximal end 860 toward the insert distal end 862 to insert shoulder 870. Each recess of the plurality of second insert recesses 896 extends into insert body 864 a distance that is equal to, or substantially equal to, less than, or greater than, the distance that ridge 892 extends into recess 839. Thus, each recess of the plurality of insert second recesses 896 is adapted to interact with ridge 892 of recess 839. In the illustrated embodiment, ridge 892 and each recess of the plurality of recesses 896 has a tapered configuration.

FIGS. 30, 31, 32, and 33 illustrate an eighth exemplary surgical implant system 1000. The implant system 1000 is similar to implant system 500 illustrated in FIGS. 19, 20, 21, and 22, and described above, except as detailed below. Reference numbers in FIGS. 30, 31, 32, and 33 refer to the same structural element or feature referenced by the same number in FIGS. 19, 20, 21, and 22, offset by 500. Thus, implant system 1000 comprises a first implant component 1002, a second implant component 1004, and an insert 1006.

In the illustrated embodiment, second implant body 1034 defines a recess 1039 that omits the inclusion of a recess second portion (e.g., recess second portion 546), a plurality of recess protuberances (e.g., plurality of recess protuberances 591), and ridge (e.g., ridge 592). Thus, recess 1039 extends from second implant proximal end 1030 to second implant distal end 1032 and from recess base 1042 away from second implant surface 1038. Recess 1039 has a recess length 1041 and a recess width 1045. Recess length 1041 extends from the second implant proximal end 1030 to the second implant distal end 1032 and recess width 1045 extends along the second implant proximal end 1030. Thus, second implant body 1034 defines a recess 1039 that extends the length of second implant component 1004 and that omits the inclusion of a ridge (e.g., ridge 592).

In the illustrated embodiment, insert 1006 comprises an insert proximal end 1060, insert distal end 1062, and an insert body 1064. Insert body 1064 defines an insert base surface 1074 and an insert articulating surface 1076. Insert base surface 1074 is flat, or substantially flat, and insert articulating surface 1076 has a radius of curvature that extends from the insert proximal end 1060 to the insert distal end 1062 and that is convex, or substantially convex.

Insert 1006 has an insert length 1063 that extends from the insert proximal end 1060 to the insert distal end 1062 and an insert width 1069 that extends along the insert proximal end 1060. Insert length 1063 is equal to, or substantially equal to, greater than, or less than, recess length 1041 and recess width 1069 is equal to, substantially equal to, less than, or greater than, recess width 1045.

FIGS. 34, 35, 36, and 37 illustrate a ninth exemplary surgical implant system 1100. The implant system 1100 is similar to implant system 600 illustrated in FIGS. 23, 24, and 25, and described above, except as detailed below. Reference numbers in FIGS. 34, 35, 36, and 37 refer to the same structural element or feature referenced by the same number in FIGS. 23, 24, and 25, offset by 500. Thus, implant system 1100 comprises a first implant component 1102, a second implant component 1104, and an insert 1106.

In the illustrated embodiment, second implant body 1134 defines a recess 1139 that omits the inclusion of a recess second portion (e.g., recess second portion 646), a plurality of recess protuberances (e.g., plurality of recess protuberances 691), and ridge (e.g., ridge 692). Thus, recess 1139 extends from the second implant proximal end 1130 to the second implant distal end 1132 and from recess base 1142 away from second implant surface 1138. Recess 1139 has a recess length 1141 and a recess width 1145. Recess length 1141 extends from the second implant proximal end 1130 to the second implant distal end 1132 and recess width 1145 extends along second implant proximal end 1130. Thus, second implant body 1134 defines a recess 1139 that extends the length of second implant component 1104 and that omits the inclusion of a ridge (e.g., ridge 692).

In the illustrated embodiment, insert 1106 omits the inclusion of a plurality of first insert recesses (e.g., plurality of first insert recesses 695) and second insert recess (e.g., second insert recess 696). Thus, insert 1006 comprises an insert proximal end 1160, insert distal end 1162, and an insert body 1164. Insert body 1164 defines an insert base 1166 and an insert articulating portion 1168. Insert base 1166 has an insert base surface 1174 and the insert articulating portion 1168 has an insert articulating surface 1176. Insert base surface 1174 extends from insert proximal end 1160 insert distal end 1162 and insert articulating surface 176 has a radius of curvature that extends from insert first side 1197 to insert second side 1198.

Insert base 1166 has an insert base width 1167 along the insert proximal end 1160 and the insert articulating portion 1168 has an insert articulating width 1169 along the insert proximal end 1160. Insert base width 1167 is equal to, substantially equal to, less than, or greater than, recess width 1145. Insert articulating width 1169 is greater than insert base width 1167.

FIGS. 38, 39, 40, and 41 illustrate a tenth exemplary surgical implant system 1200. The implant system 1200 is similar to implant system 100 illustrated in FIGS. 3, 4, 5, and 6, and described above, except as detailed below. Reference numbers in FIGS. 38, 39, 40, and 41 refer to the same structural element or feature referenced by the same number in FIGS. 3, 4, 5, and 6, offset by 1100. Thus, implant system 1200 comprises a first implant component 1202, a second implant component 1204, and an insert 1206.

In the illustrated embodiment, alternative to second implant component defining a recess and a plurality of recess projections, first implant body 1212 defines a convex, or substantially convex, first implant surface 1216, recess 1239, and a plurality of recess projections 1240. Recess 1239 is adapted to receive a portion, or the entirety, of insert 1206. Recess 1239 has a recess length 1241, recess base 1242, recess first portion 1244, and a recess second portion 1246. Recess 1239 extends into first implant body 1212 to recess base 1242 and from first implant proximal end 1208 to first implant distal end 1210. Recess length 1241 extends from first implant proximal end 1208 to first implant distal end 1210.

Each projection of the plurality of recess projections 1240 extends into recess 1239 along a portion, or the entirety, of recess length 1241 and has a tapered edge that is adapted to interact with a portion of insert 1206 to releasably attach insert 1206 to first implant component 1202. Recess base 1242 is opposably facing, or substantially opposably facing, first implant surface 1216, is concave, or substantially concave, and is smooth, substantially smooth, or uninterrupted. Recess base 1242 has a radius of curvature that extends from first implant proximal end 1208 to first implant distal end 1210. Recess first portion 1244 extends from recess base 1242 to the plurality of recess projections 1240 and has a recess first portion width 1245 along first implant proximal end 1208. Recess second portion 1246 has a recess second portion width 1247 along first implant proximal end 1208 that is measured from a first recess projection of the plurality of recess projections 1240 to a second recess projection of the plurality of recess projections 1240. The recess first portion width 1245 is greater than the recess second portion width 1247.

In the illustrated embodiment, second implant body 1234 defines a concave, or substantially concave, second implant surface 1238 and an opposably facing, or substantially opposably facing, convex, or substantially convex, second articulating surface 1243. Each of the second implant surface 1238 and second articulating surface 1243 has a radius of curvature that extends from second implant proximal end 1230 to second implant distal end 1232. Second implant surface 1238 is smooth, substantially smooth, or uninterrupted and second articulating surface 1243 is smooth, substantially smooth, or uninterrupted, such that articulation between articulating surface 1243 and insert 1206 can be accomplished, as described in more detail herein.

In the illustrated embodiment, insert 1206 comprises an insert proximal end 1260, insert distal end 1262, and an insert body 1264. Alternative to insert being attached to a second implant component, insert 1206 is adapted to be attached to first implant component 1202. In addition, alternative to insert body defining an insert recess and a recess shoulder, insert body 1264 defines an insert base 1266, insert articulating portion 1268, a first insert recess 1296, and a second insert recess 1296'.

Insert base 1266 has an insert base surface 1274 and the insert articulating portion 1268 has an insert articulating surface 1276. Each of insert base surface 1274 and insert articulating portion 1268 has a radius of curvature that extends from insert proximal end 1260 to insert distal end 1262. Insert base surface 1274 is convex, or substantially convex, and is opposably facing, or substantially opposably facing, insert articulating surface 1276, which is concave, or substantially concave. Insert base surface 1274 is smooth, substantially smooth, or uninterrupted, and is complementary to recess base 1242 such that insert 1206 is slidable along recess base 1242 and releasable attachment between insert 1206 and first implant component 1202 can be accomplished. Insert articulating surface 1276 is smooth, substantially smooth, or uninterrupted, and is complementary to second articulating surface 1243 such that insert 1206 can articulate with second implant component 1204. Thus, insert articulating surface 1276 is adapted to articulate with second articulating surface 1243.

Insert base 1266 has an insert base width 1267 along insert proximal end 1260 and insert articulating portion 1268 has an insert articulating width 1269 along insert proximal end 1260. Insert base width 1267 is equal to, substantially equal to, less than, or greater than, recess first portion width 1245. Insert articulating width 1269 is greater than, recess second portion width 1247.

Each of first insert recess 1296 and second insert recess 1296' extends into recess body 1264 between insert base 1266 and insert articulating surface 1276. First insert recess 1296 extends along insert first side 1297 and second insert recess 1296' extends along insert second side 1298. Each of the first insert recess 1296 and second insert recess 1296' extends into insert body 1264 a distance that is equal to, or substantially equal to, less than, or greater than, the distance that a projection of the plurality of projections 1270 extends into recess 1239. It is considered advantageous to include an insert 1206 having a insert articulating width 1269 that is greater than the recess second portion width 1247 and a first insert recess 1296 and second insert recess 1296' at least because this structural arrangement provides a mechanism for achieving a slideably engagement between a first implant component 1202 and an insert.

FIGS. 42, 43, 44, and 45 illustrate an eleventh exemplary surgical implant system 1300. The implant system 1300 is similar to implant system 1200 illustrated in FIGS. 38, 39, 40, and 41, and described above, except as detailed below. Reference numbers in FIGS. 42, 43, 44, and 45 refer to the same structural element or feature referenced by the same number in FIGS. 38, 39, 40, and 41, offset by 100. Thus, implant system 1300 comprises a first implant component 1302, a second implant component 1304, and an insert 1306.

In the illustrated embodiment, first implant component 1302 includes a plurality of first implant projections 1314, a first implant tab 1377, and a plurality of fasteners 1378 and second implant component 1304 includes a plurality of second implant projections 1336, a second implant tab 1383, and a plurality of fasteners 1378. The plurality of first implant projections 1314 is similar to the plurality of first implant projections 214 illustrated in FIGS. 7, 8, 9, and 10. First implant tab 1377 is similar to first implant tab 277 illustrated in FIGS. 7, 8, 9, and 10. The plurality of fasteners 1378 is similar to the plurality of fasteners 278 illustrated in FIGS. 7, 8, 9, and 10. The plurality of second implant projections 1336 is similar to the plurality of second implant projections 236 illustrated in FIGS. 7, 8, 9, and 10. Second implant tab 1383 is similar to second implant tab 283 illustrated in FIGS. 7, 8, 9, and 10. Reference numbers relating to the plurality of first implant projections 1314, first implant tab 1377, plurality of fasteners 1378, plurality of second implant projections 1336, second implant tab 1383 in FIGS. 42, 43, 44, and 45 refer to the same structural element or feature referenced by the same number in FIGS. 7, 8, 9, and 10, offset by 1100.

Thus, first implant tab 1377 comprises a first implant tab wall 1379 that defines a plurality of first implant bores 1380, each fastener of the plurality of fasteners 1378 has a fastener first end 1381 and a fastener second end 1382, and second implant tab comprises a second implant tab wall 1384 that defines a plurality of second implant bores 1385. Optionally, each bore of the plurality of first implant bores 1380, or a portion thereof, can be countersunk or counterbored to allow a fastener to sit flush with, or below, the outer surface of first implant 1302 and each bore of the plurality of second implant bores 1385, or a portion thereof, can be countersunk or counterbored to allow a fastener to sit flush with, or below, the outer surface of second implant 1304. Thus, a first fastener is disposed through a first bore defined by first implant tab wall 1379 and a second fastener is disposed through a second bore defined by first implant tab wall 1379 and a first fastener is disposed through a first bore defined by second implant tab wall 1384 and a second fastener is disposed through a second bore defined by second implant tab wall 1384. A fastener can be disposed through each bore defined by a first implant tab wall and/or second implant tab wall.

In the illustrated embodiment, each bore of the plurality of first implant bores 1380 and each bore of the plurality of second implant bores 1385 has a bore axis that extends through its center. Each bore axis of the plurality of first implant bores 1380 is disposed on a first plane and each bore axis of the plurality of second implant bores 1385 is disposed on a second plane that intersects the first plane at an angle. The first plane and second plane can intersect at any suitable angle, and skilled artisans will be able to select a suitable angle for a first plane and a second plane to intersect according to a particular embodiment based on various considerations, including the structural arrangement at a treatment site. Example angles considered suitable for a first plane and a second plane to intersect include, but are not limited to, an angle between about 1 degree and 90 degrees, an angle between about 90 degrees and about 180 degrees, a 90 degree angle, a substantially 90 degree angle, a 45 degree angle, a substantially 45 degree angle, an acute angle, an obtuse angle, and any other angle considered suitable for a particular application. Alternatively, a first plane that contains each bore axis of a plurality of first implant bores can extend parallel, or substantially parallel, to a second plane that contains each bore axis of a plurality of second implant bores.

While particular combinations of implant components, inserts, and features thereof have been described and illustrated herein, an implant system can combine any suitable implant component, insert, and/or feature thereof in any suitable manner to form an implant system. Skilled artisans will be able to select a suitable implant component, insert, and/or feature thereof to form an implant system according to a particular embodiment based on various considerations, including the structural arrangement at an implant site.

Various methods of treatment are described and illustrated. While the methods described herein are shown and described as a series of acts, it is to be understood and appreciated that the methods are not limited by the order of acts, as one or more acts may, in accordance with these methods, occur in different orders with one or more other acts described herein, or any other suitable act(s), concurrently with one or more other acts described herein, or any other suitable act(s), and/or in the alternative to one or more other acts described herein, or any other suitable act(s).

Figure 46:
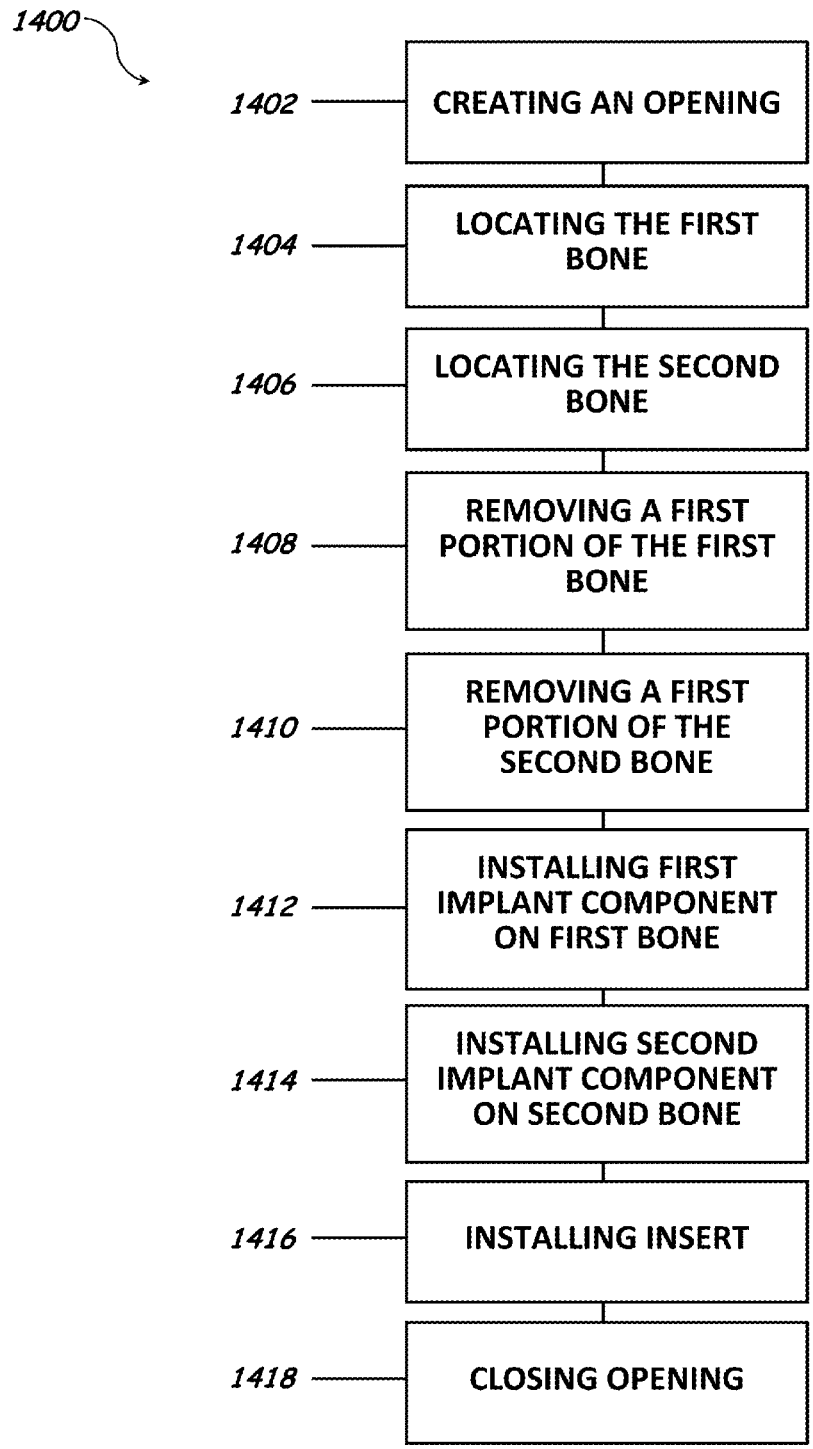
FIG. 46 is a flowchart representation of an exemplary method of treatment.

FIG. 46 is a flowchart representation of an exemplary method 1400 of modifying a joint.

An initial step 1402 comprises creating an opening in a body to provide access to a joint formed between a first bone and a second bone. Another step 1404 comprises locating the first bone of the joint. Another step 1406 comprises locating the second bone of the joint. Another step 1408 comprises removing a first portion of the first bone to configure the first bone to receive a first implant component. Another step 1410 comprises removing a first portion of the second bone to configure the second bone to receive a second implant component. Another step 1412 comprises installing the first implant component on the first bone. Another step 1414 comprises installing the second implant component on the second bone. Another step 1416 comprises installing an insert on one of the first implant component or second implant component. Another step 1418 comprises closing the opening.

The step 1402 of creating an opening can be accomplished using any suitable tool and/or method of creating an opening (e.g., in a body) and can be created at any suitable location on a body, and skilled artisans will be able to select a suitable tool and/or method to create an opening and a suitable location on a body to create an opening according to a particular embodiment based on various considerations, including the size and location of the opening. Example methods and/or tools considered suitable for creating an opening include, but are not limited to, scalpels, lasers, and any other tool and/or method considered suitable for a particular application. Example locations considered suitable to create an opening on a body include, but are not limited to, on the foot, on the ankle, lateral portion of the foot, posterior and lateral portion of the foot, medial portion of the foot, posterior and medial portion of the foot, and any other location considered suitable for a particular application.

While step 1402 has been illustrated and described as being an initial step to methodology 1400, any other suitable step can be completed prior to the step of creating on opening to provide access to a joint, and skilled artisans will be able to select a suitable step to complete prior to creating an opening to provide access to a joint according to a particular embodiment based on various considerations, including the location of the joint intended to be treated. An example step that can be completed prior to the step of creating an opening includes, but is not limited to, preparing the location of a desired opening for an incision (e.g., cleaning the area).

The step 1404 of locating the first bone of the joint, and the step 1406 of locating the second bone of the joint, can each be accomplished using any suitable method of visualization, and skilled artisans will be able to select a suitable method of visualization to locate a first bone and/or a second bone according to a particular embodiment based on various considerations, including the location of the first bone and/or second bone. Example methods of visualization considered suitable include, but are not limited to, direct visualization, using a scope, and any other method of visualization considered suitable for a particular application.

The step 1408 of removing a first portion of the first bone to configure the first bone to receive a first implant component, and the step 1410 of removing a first portion of the second bone to configure the second bone to receive a second implant component, can each be accomplished using any suitable technique and/or tool for removing a portion of a bone (e.g., to prepare a bone to receive an implant component). Skilled artisans will be able to select a suitable technique and/or tool for removing a portion of a bone to configure the bone to receive an implant component according to a particular embodiment based on various considerations, including the size and location of the implant site.

Example methods of removing a portion of a bone to configure the bone to receive an implant component include, but are not limited to, conventional techniques, drilling, sanding, cutting, and any other method considered suitable for a particular application. Example tools considered suitable for removing a portion of a bone to configure the bone to receive an implant component include, but are not limited to, conventional tools, drills, sanders, saws (e.g., bone saws), and any other tool considered suitable for a particular application.

An optional step comprises testing the fit between the first implant component and the first bone. Another optional step comprises testing the fit between the second implant component and the second bone. Each of the steps of testing the fit between the first implant component and the first bone, and testing the fit between the second implant component and the second bone, can be accomplished by advancing the implant component toward the implant site, contacting the implant component on the bone, and determining if a desired fit between the bone and the implant component has been achieved. If a desired fit between the bone and the implant component has not been achieved, another optional step comprises removing a second portion of the first bone, and/or removing a second portion of the second bone, to configure the first bone and/or the second bone to receive an implant component. Alternative to, or in combination with, the step of removing a second portion of the first bone and/or removing a second portion of the second bone, a step comprising fitting another implant component different than the first implant component and/or second implant component between the first bone and/or second bone can be completed.

Another optional step comprises preparing the surface of the bone (e.g., first bone, second bone) to receive an implant component. This step can be accomplished using any suitable method, material, and/or tool, and skilled artisans will be able to select a suitable method, material, and/or tool to prepare the surface of a bone to receive an implant component according to a particular embodiment based on various considerations, including the type of attachment desired between an implant component and the bone. Examples methods, materials, and/or tools considered suitable to prepare the surface of the bone to receive an implant component include, but are not limited to, using an abrasive, using an air-powered abrasive unit, etching the bone, cleaning the bone, and any other method, material, and/or tool considered suitable for a particular application.

The step 1412 of installing the first implant component on the first bone, and the step 1414 of installing the second implant component on the second bone, can each be accomplished using any suitable method of attachment and/or any suitable tool. Example methods of attachment and/or tools considered suitable include, but are not limited to, using a peg, tab, keel, fastener, screw, bolt, adhesive, cement, and any other method of attachment and/or tool considered suitable for a particular application.

The step 1416 of installing an insert on one of the first implant component or second implant component can be accomplished by advancing the insert toward the implant site, and/or by inserting the insert into one of the first implant component or second implant component. For example, this step can be accomplished by placing an insert in a recess defined by an implant component.

An optional step comprises attaching the insert to one of the first implant component or second implant component. This step can be accomplished using any suitable method of attachment and/or any suitable tool. Example methods of attachment and/or tools considered suitable include, but are not limited to, using a fastener, screw, bolt, adhesive, cement, and any other method of attachment and/or tool considered suitable for a particular application.

The step 1418 of closing the opening can be accomplished using any suitable method of closing an opening, and/or by using any suitable device, and skilled artisans will be able to select a suitable method and/or device for closing an opening according to a particular embodiment based on various considerations, including the location and size of the opening. Example methods and/or devices considered suitable for closing an opening include, but are not limited to, using sutures, staples, strips, glues (e.g., liquid tissue glues), and any other method and/or device considered suitable for a particular application.

Methodology 1400 can accomplished on any suitable joint (e.g., in a body), and skilled artisans will be able to select a suitable joint to perform a method described herein according to a particular embodiment based on various considerations, including the desired treatment intended to be performed. Example joints considered suitable to perform a methodology described herein include, but are not limited to, the subtalar joint, talonavicular joint, calcaneocuboid joint, and any other joint considered suitable for a particular application.

While various steps, alternative steps, and/or optional steps have been described above with respect to an exemplary method of treatment 1400, these steps, alternative steps, and/or optional steps can be included in, accomplished concurrently with, and/or accomplished in the alternative to, the methodologies, steps, alternative steps, and/or optional steps described herein with respect to exemplary method of treatment 1500, exemplary method of treatment 1600, and/or exemplary method of treatment 1700.

Figure 47:
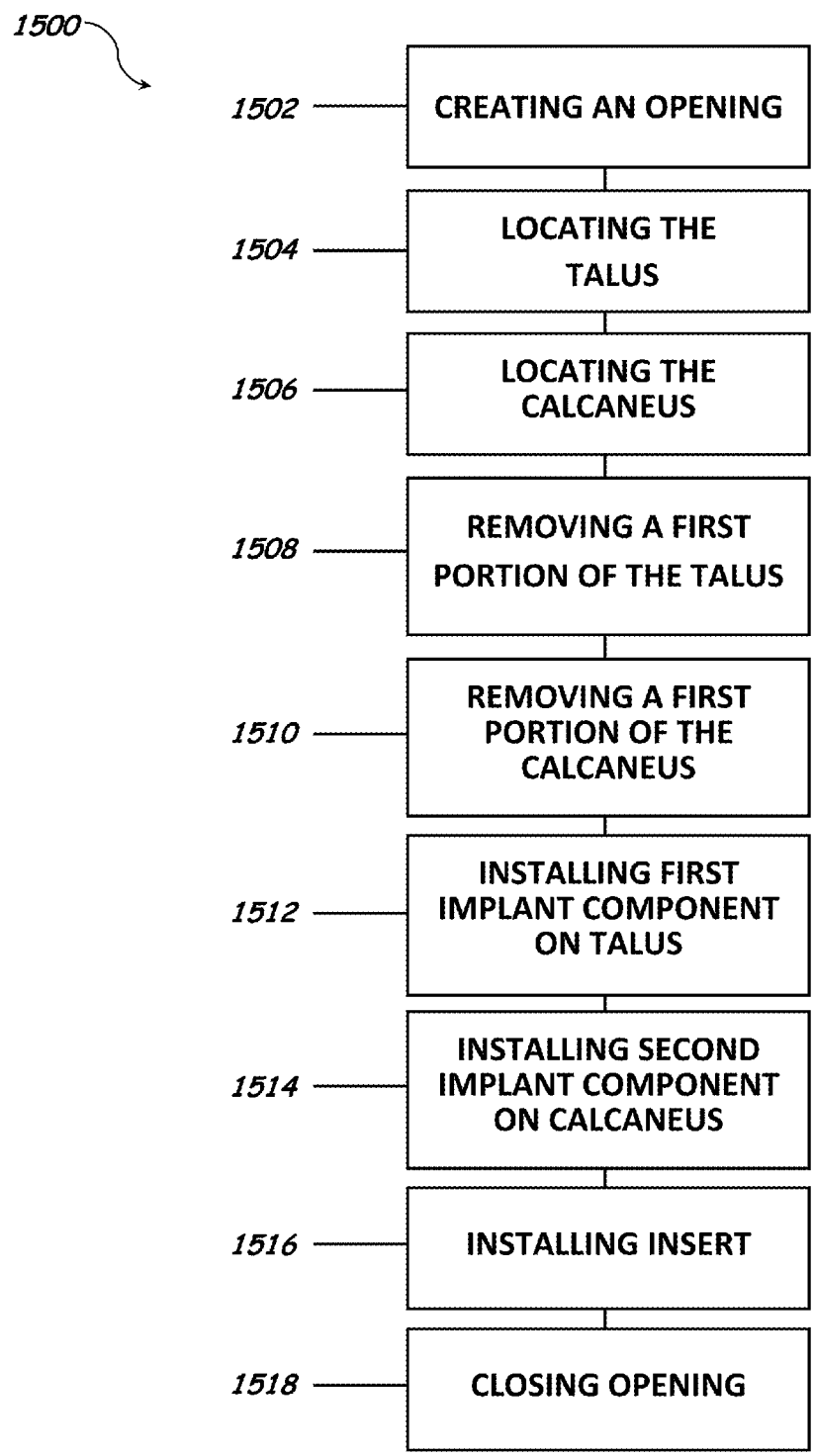
FIG. 47 is a flowchart representation of a second exemplary method of treatment.

FIG. 47 is a flowchart representation of an exemplary method 1500 of modifying the subtalar joint.

An initial step 1502 comprises creating an opening to provide access to the subtalar joint formed between the talus and calcaneus. Another step 1504 comprises locating the talus. Another step 1506 comprises locating the calcaneus. Another step 1508 comprises removing a first portion of the talus to configure the talus to receive a first implant component. Another step 1510 comprises removing a first portion of the calcaneus to configure the calcaneus to receive a second implant component. Another step 1512 comprises installing the first implant component on the talus. Another step 1514 comprises installing the second implant component on the calcaneus. Another step 1516 comprises installing an insert on one of the first implant component or second implant component. Another step 1518 comprises closing the opening.

The step 1502 of creating an opening to provide access to the subtalar joint formed between the talus and calcaneus can be accomplished by creating an opening at any suitable location, and skilled artisans will be able to select a suitable location to create an opening according to a particular embodiment based on various considerations, including the size of the implant components intended to be used. Example locations considered suitable to create an opening include, but are not limited to, creating an opening such that a lateral approach of the subtalar joint can be accomplished, creating an opening such that a medial approach of the subtalar joint can be accomplished, creating an opening such that a posterior and lateral approach of the subtalar joint can be accomplished, creating an opening such that a posterior and medial approach of the subtalar joint can be accomplished, and any other location considered suitable for a particular application. For example, an opening can be created at, near, behind, and/or around the peroneal tendons (e.g., between the peroneal tendons and the Achilles tendon).

An alternative step to the step 1512 of installing the first implant component on the talus comprises installing a second implant component on the talus. An alternative step to the step 1514 of installing the second implant component on the calcaneus comprises installing a first implant component on the calcaneus.

While various steps, alternative steps, and/or optional steps have been described above with respect to an exemplary method of treatment 1500, these steps, alternative steps, and/or optional steps can be included in, accomplished concurrently with, and/or accomplished in the alternative to, the methodologies, steps, alternative steps, and/or optional steps described herein with respect to exemplary method of treatment 1400, exemplary method of treatment 1600, and/or exemplary method of treatment 1700.

Figure 48:
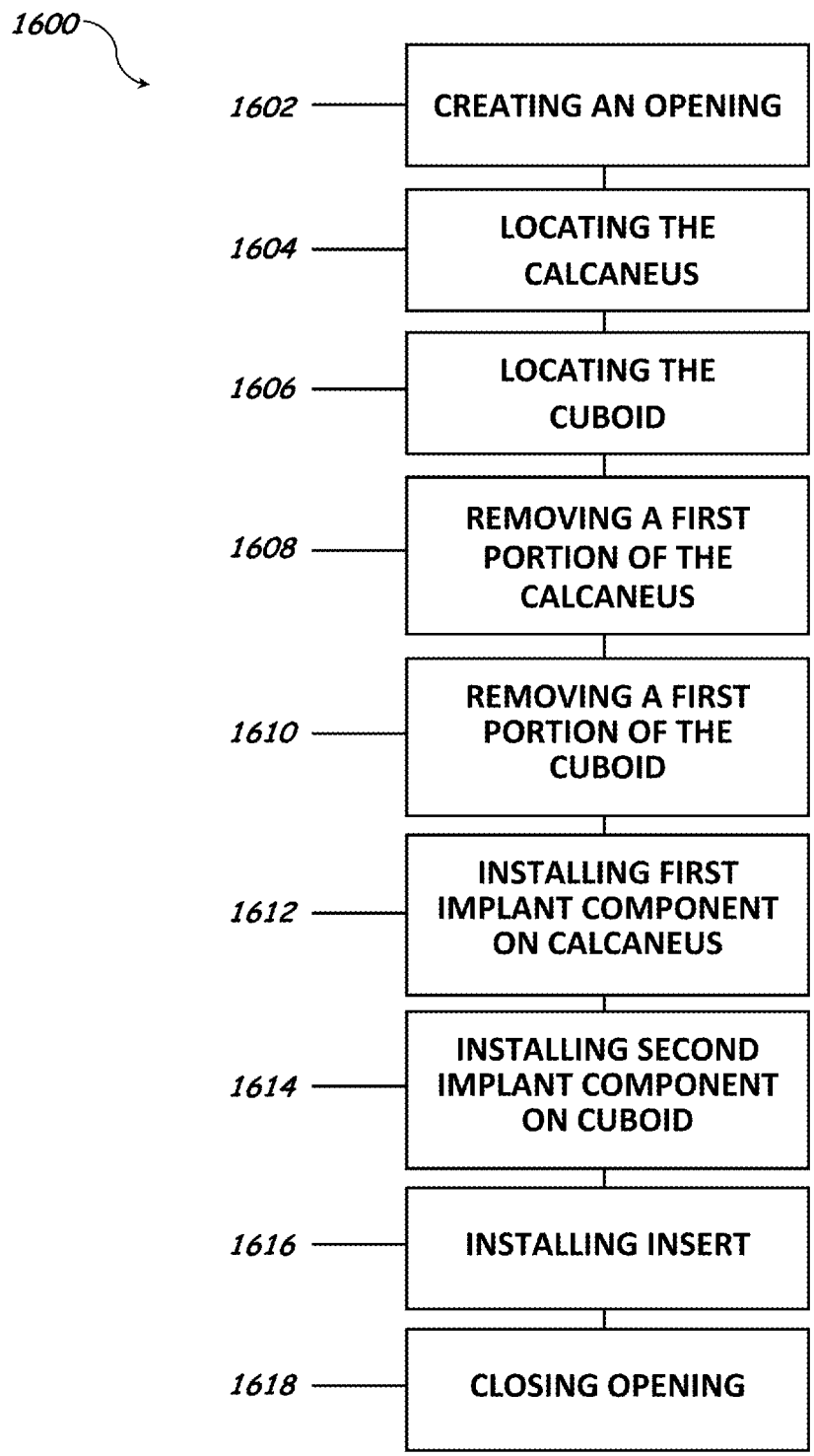
FIG. 48 is a flowchart representation of a third exemplary method of treatment.

FIG. 48 is a flowchart representation of an exemplary method 1600 of modifying the calcaneocuboid joint.

An initial step 1602 comprises creating an opening to provide access to the calcaneocuboid joint formed between the calcaneus and cuboid. Another step 1604 comprises locating the calcaneus. Another step 1606 comprises locating the cuboid. Another step 1608 comprises removing a first portion of the calcaneus to configure the calcaneus to receive a first implant component. Another step 1610 comprises removing a first portion of the cuboid to configure the cuboid to receive a second implant component. Another step 1612 comprises installing the first implant component on the calcaneus. Another step 1614 comprises installing the second implant component on the cuboid. Another step 1616 comprises installing an insert on one of the first implant component or second implant component. Another step 1618 comprises closing the opening.

The step 1602 of creating an opening to provide access to the calcaneocuboid joint formed between the calcaneus and cuboid can be accomplished by creating an opening at any suitable location, and skilled artisans will be able to select a suitable location to create an opening according to a particular embodiment based on various considerations, including the size of the implant components intended to be used. Example locations considered suitable to create an opening include, but are not limited to, creating an opening such that a lateral approach of the calcaneocuboid joint can be accomplished, creating an opening such that a medial approach of the calcaneocuboid joint can be accomplished, and any other location considered suitable for a particular application. For example, an opening can be created at, near, behind, and/or around the extensor brevis.

An alternative step to the step 1612 of installing the first implant component on the calcaneus comprises installing a second implant component on the calcaneus. An alternative step to the step 1614 of installing the second implant component on the cuboid comprises installing a first implant component on the cuboid.

While various steps, alternative steps, and/or optional steps have been described above with respect to an exemplary method of treatment 1600, these steps, alternative steps, and/or optional steps can be included in, accomplished concurrently with, and/or accomplished in the alternative to, the methodologies, steps, alternative steps, and/or optional steps described herein with respect to exemplary method of treatment 1400, exemplary method of treatment 1500, and/or exemplary method of treatment 1700.

Figure 49:
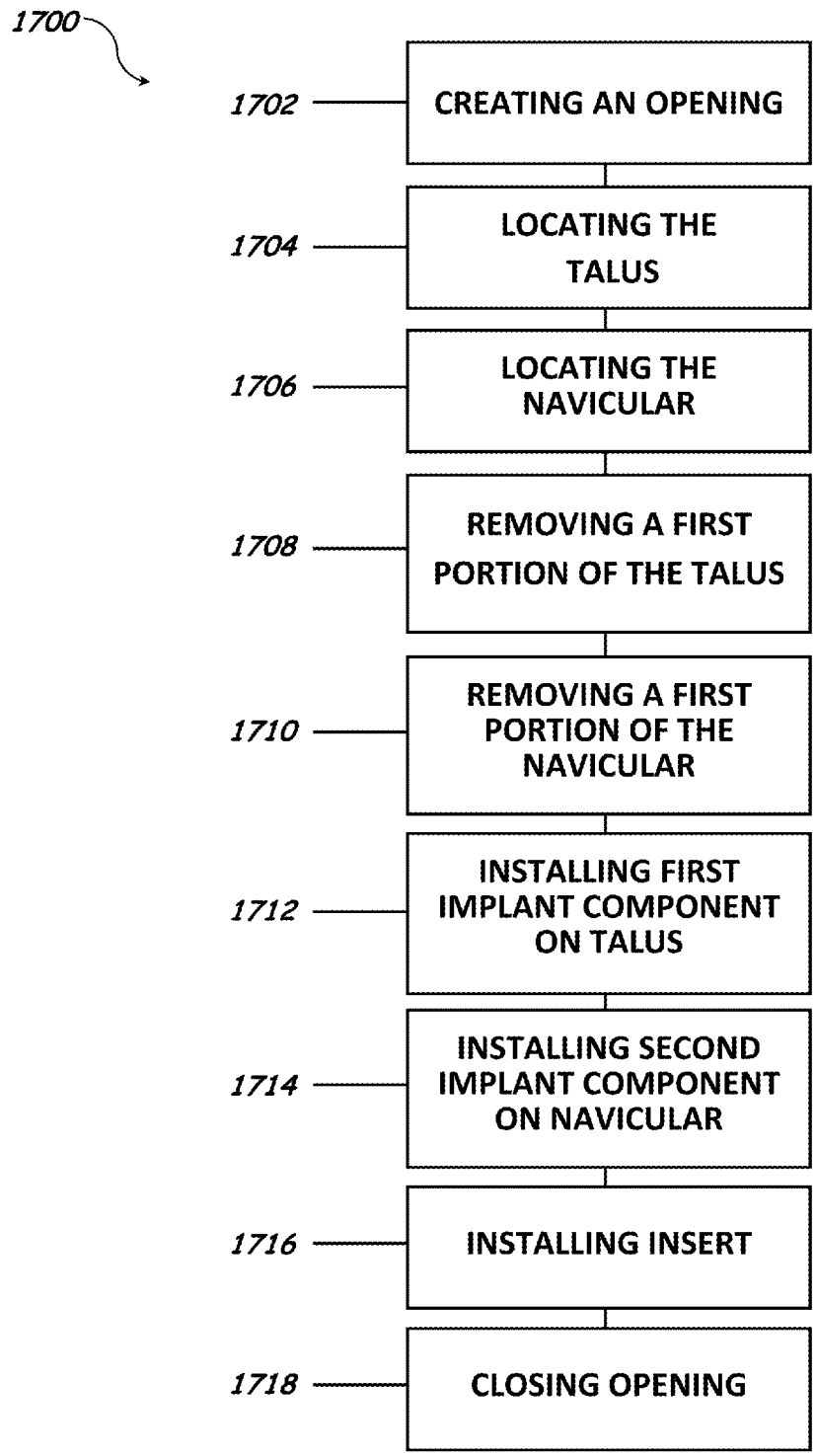
FIG. 49 is a flowchart representation of a fourth exemplary method of treatment.
Figure 50:
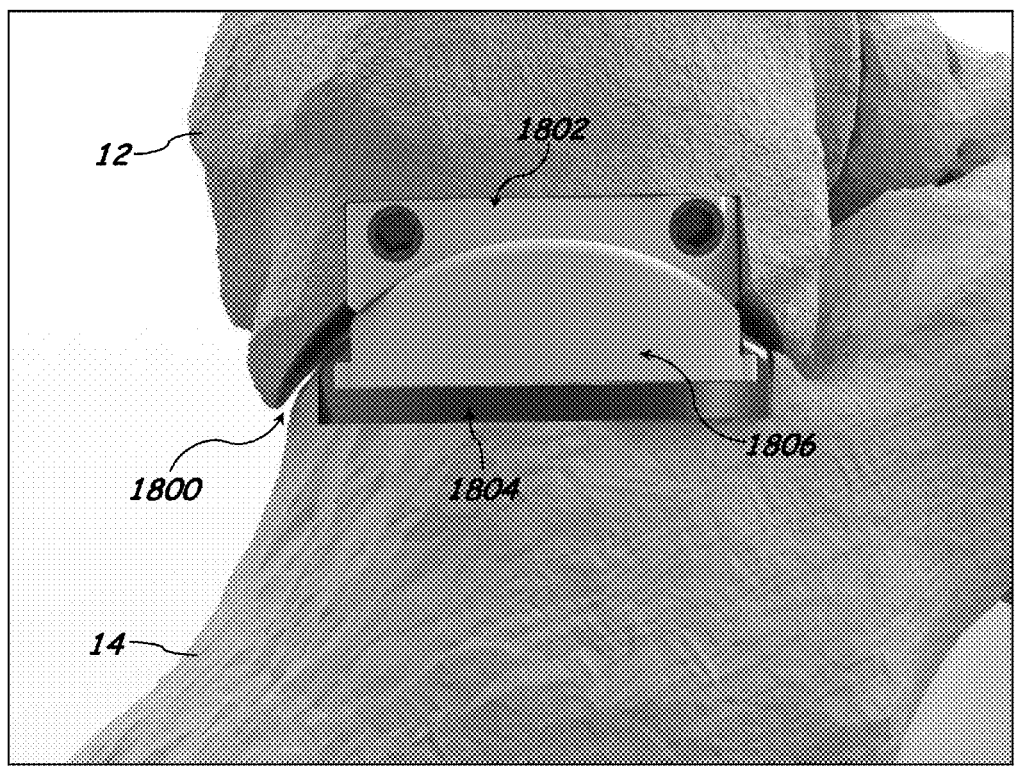
FIG. 50 is a perspective view of a twelfth exemplary implant system disposed in the subtalar joint of a human foot.
Figure 51:
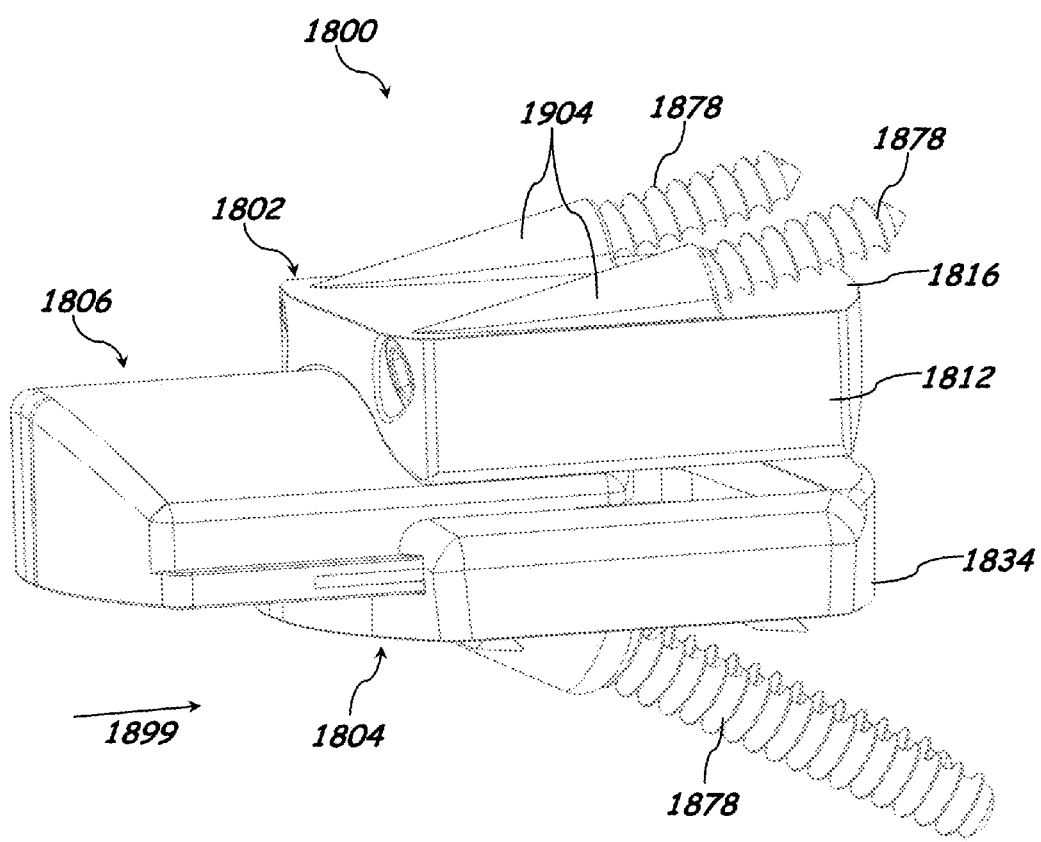
FIG. 51 is a perspective view of the exemplary implant system illustrated in FIG. 50, free of the subtalar joint, with the insert partially disposed in the second implant component.
Figure 52:
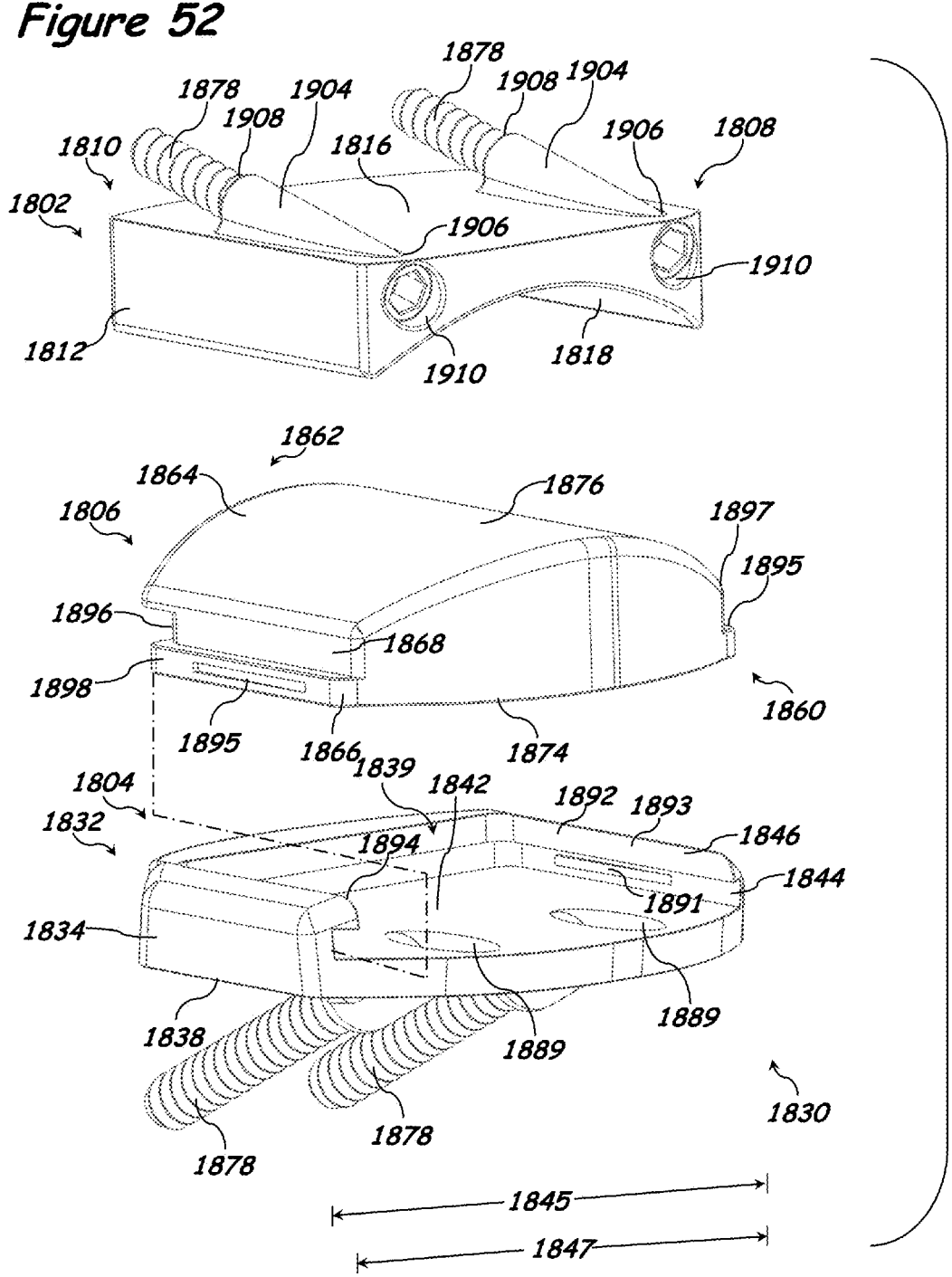
FIG. 52 is an exploded view of the exemplary implant system illustrated in FIG. 51.
Figure 53:
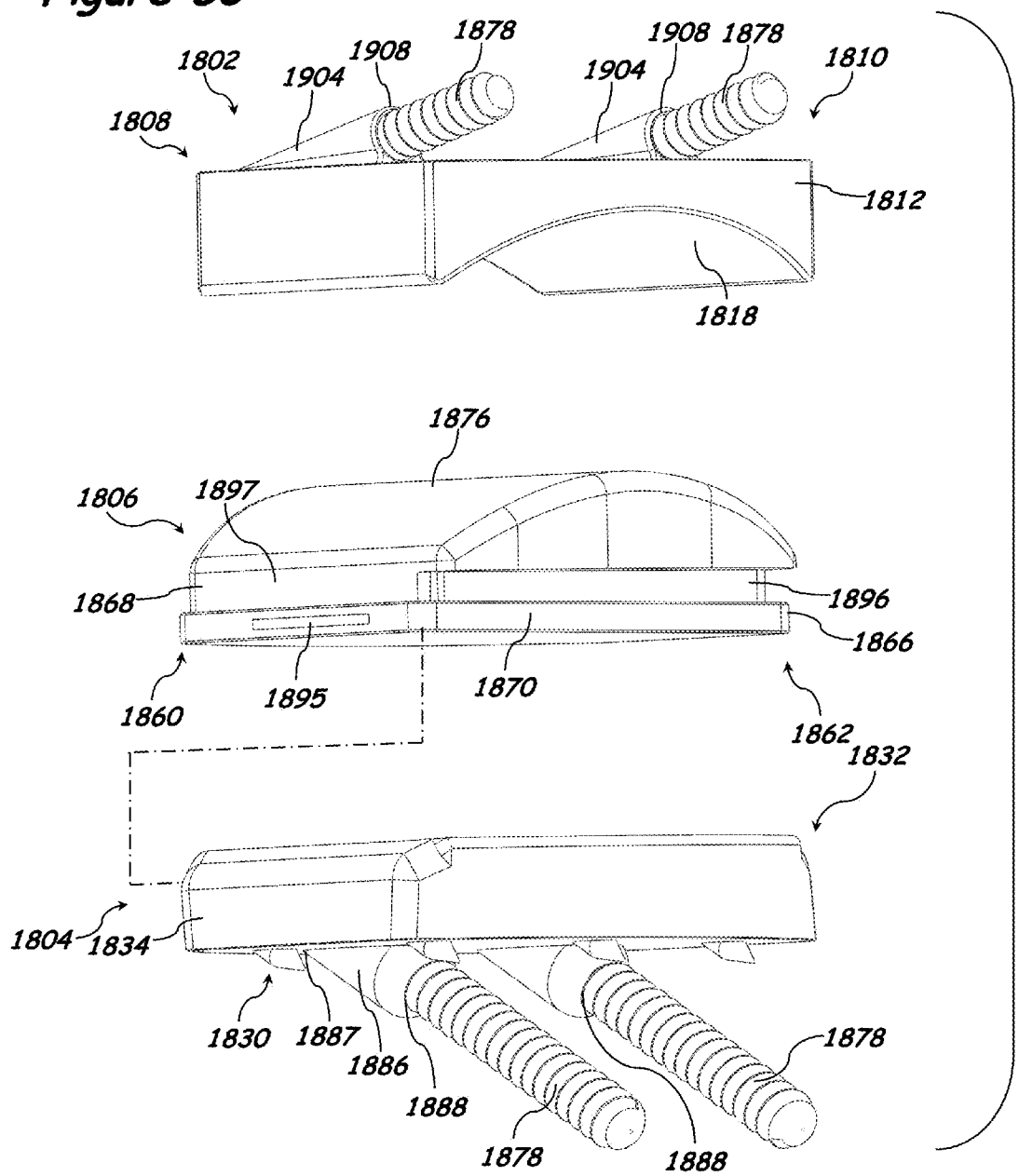
FIG. 53 is another exploded view of the exemplary implant system illustrated in FIG. 51.
Figure 54:
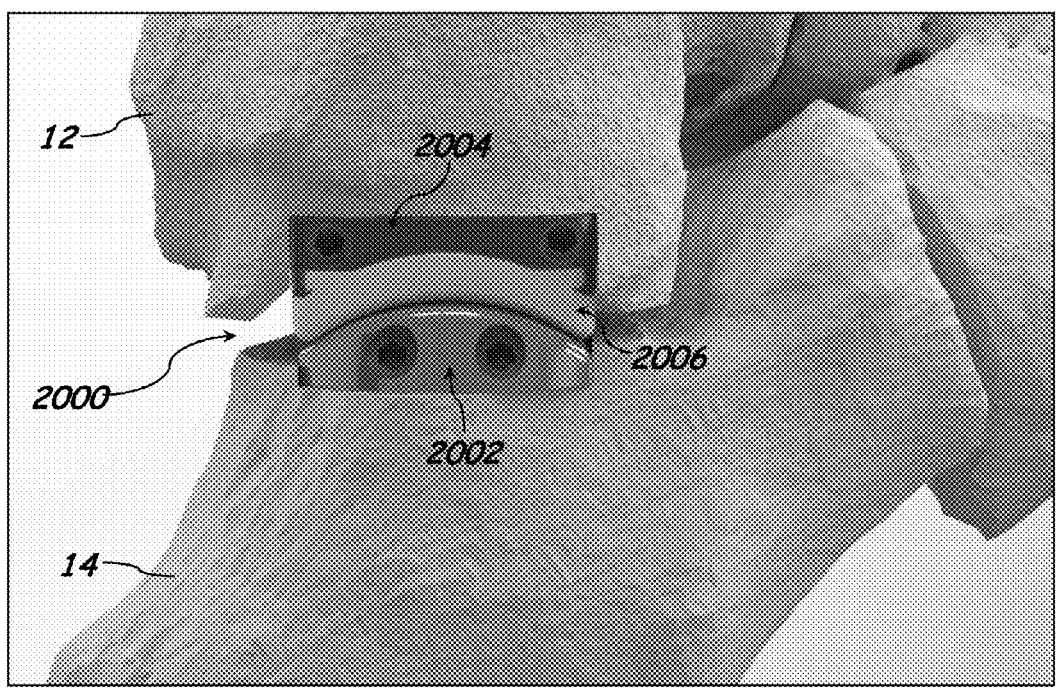
FIG. 54 is a perspective view of a thirteenth exemplary implant system disposed in the subtalar joint of a human foot.
Figure 55:
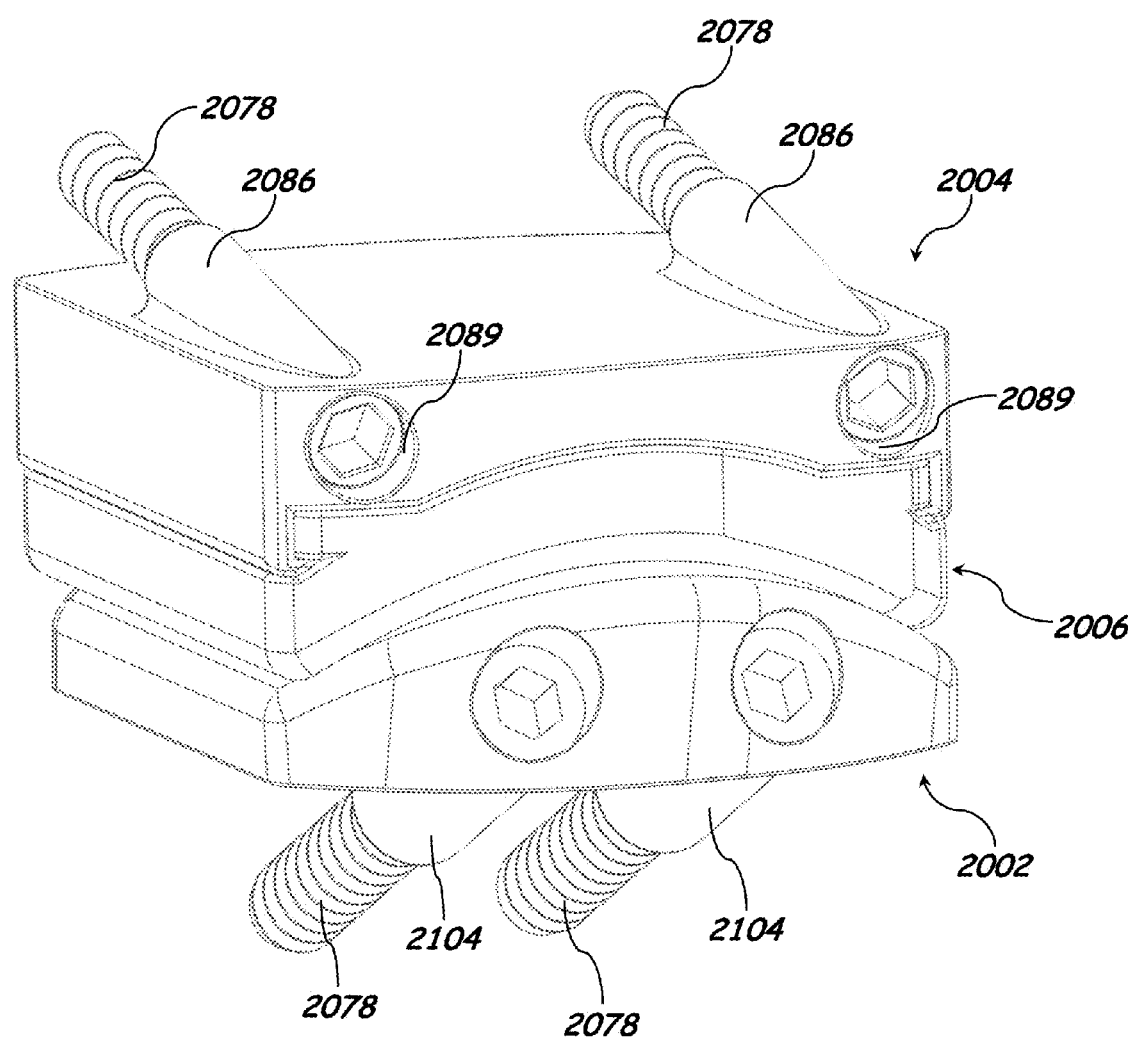
FIG. 55 is a perspective view of the exemplary implant system illustrated in FIG. 54, free of the subtalar joint.
Figure 56:
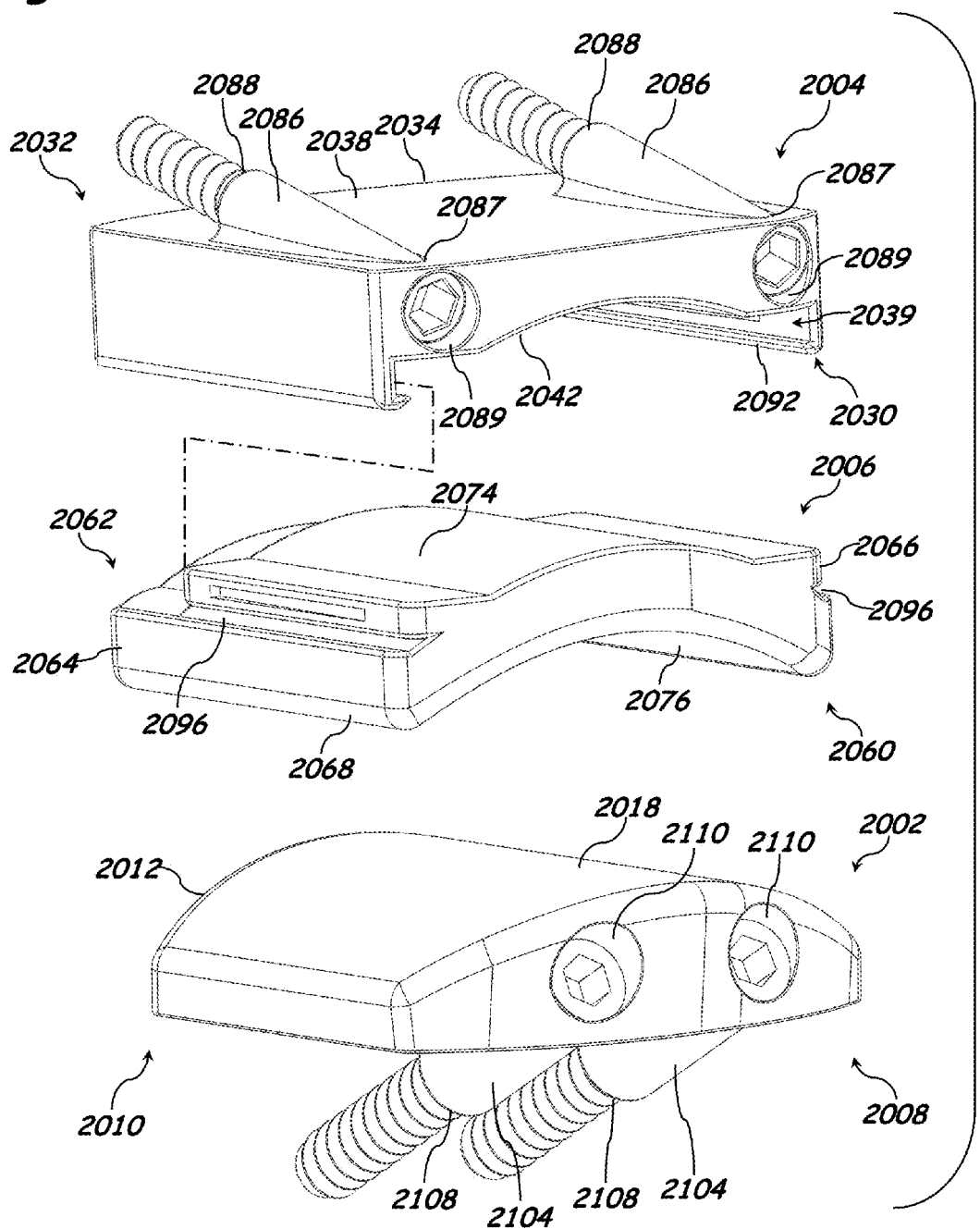
FIG. 56 is an exploded view of the exemplary implant system illustrated in FIG. 54.
Figure 57:
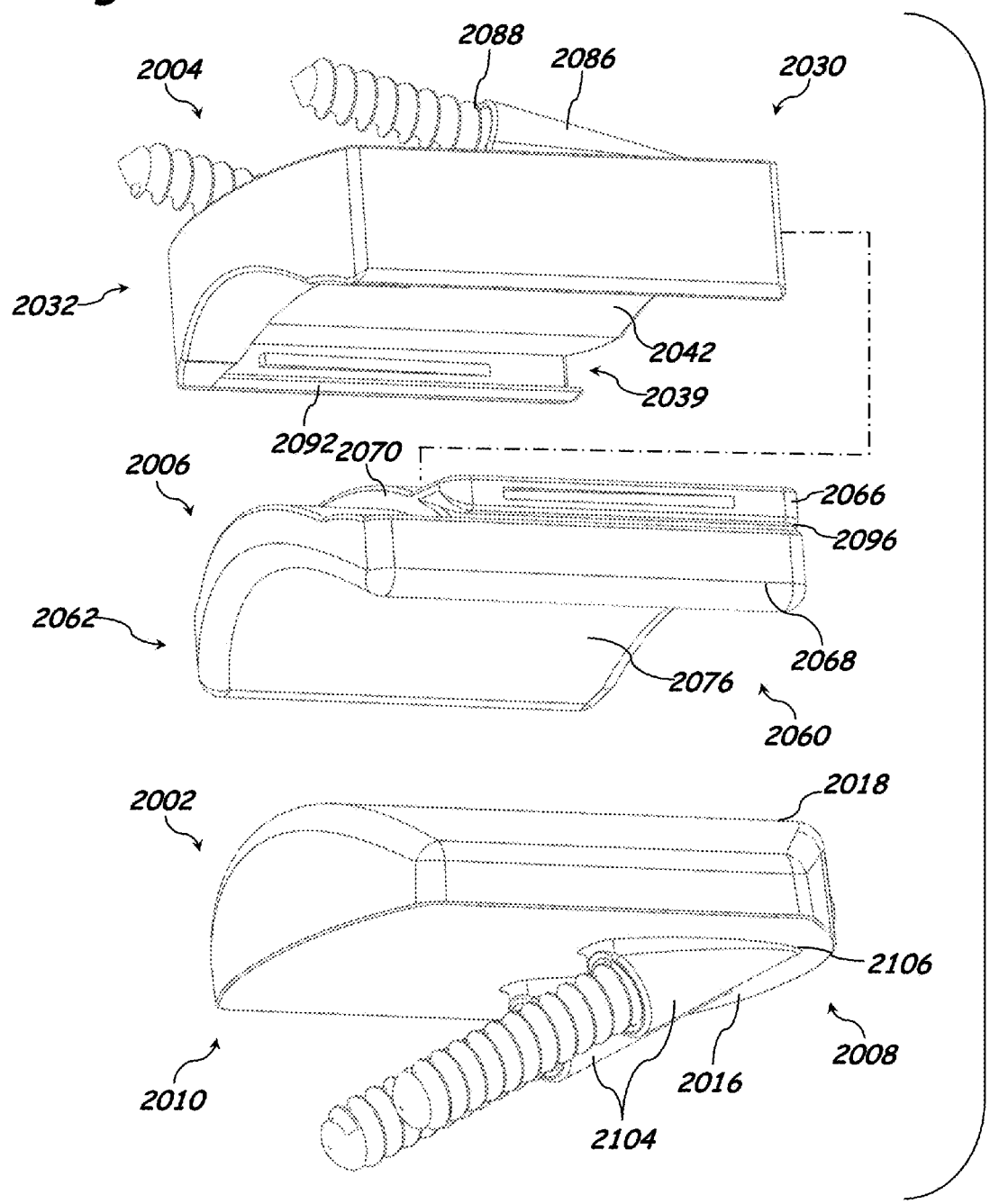
FIG. 57 is another exploded view of the exemplary implant system illustrated in FIG. 54.

FIG. 49 is a flowchart representation of an exemplary method 1700 of modifying the talonavicular joint.

An initial step 1702 comprises creating an opening to provide access to the talonavicular joint formed between the talus and navicular. Another step 1704 comprises locating the talus. Another step 1706 comprises locating the navicular. Another step 1708 comprises removing a first portion of the talus to configure the talus to receive a first implant component. Another step 1710 comprises removing a first portion of the navicular to configure the navicular to receive a second implant component. Another step 1712 comprises installing the first implant component on the talus. Another step 1714 comprises installing the second implant component on the navicular. Another step 1716 comprises installing an insert on one of the first implant component or second implant component. Another step 1718 comprises closing the opening.

The step 1702 of creating an opening to provide access to the talonavicular joint formed between the talus and navicular can be accomplished by creating an opening at any suitable location, and skilled artisans will be able to select a suitable location to create an opening according to a particular embodiment based on various considerations, including the size of the implant components intended to be used. Example locations considered suitable to create an opening include, but are not limited to, creating an opening such that a lateral approach of the talonavicular joint can be accomplished, creating an opening such that a medial approach of the talonavicular joint can be accomplished, and any other location considered suitable for a particular application.

An alternative step to the step 1712 of installing the first implant component on the talus comprises installing a second implant component on the talus. An alternative step to the step 1714 of installing the second implant component on the navicular comprises installing a first implant component on the navicular.

While various steps, alternative steps, and/or optional steps have been described above with respect to an exemplary method of treatment 1700, these steps, alternative steps, and/or optional steps can be included in, accomplished concurrently with, and/or accomplished in the alternative to, the methodologies, steps, alternative steps, and/or optional steps described herein with respect to exemplary method of treatment 1400, exemplary method of treatment 1500, and/or exemplary method of treatment 1600.

FIGS. 50, 51, 52, and 53 illustrate a twelfth exemplary surgical implant system 1800. The implant system 1800 is similar to implant system 500 illustrated in FIGS. 19, 20, 21, and 22, and described above, except as detailed below. Reference numbers in FIGS. 50, 51, 52, and 53 refer to the same structural element or feature referenced by the same number in FIGS. 19, 20, 21, and 22, offset by 1500. Thus, implant system 1800 comprises a first implant component 1802, a second implant component 1804, and an insert 1806.

In the illustrated embodiment, alternative to first implant body defining a plurality of bores that extend through the first implant proximal end and through the first implant surface, first implant body 1812 defines a plurality of first implant protuberances 1904. Each protuberance of the plurality of first implant protuberances 1904 extends outward and away from the first implant surface 1816 from a protuberance first end 1906 toward first implant distal end 1810 to a protuberance second end 1908 at an acute, or substantially acute, angle with respect to first implant surface 1816. The first implant body 1812 defines a passageway 1910 through each protuberance of the plurality of first implant protuberances 1904 and that extends from a first opening defined on the first implant proximal end 1808 to a second opening defined on the protuberance second end 1908. Each passageway 1910 provides access for passing a fastener of the plurality of fasteners 1878 through a protuberance of the plurality of protuberances 1904 to attach, or assist with attaching, first implant component 1802 at an implant site. Optionally, each passageway 1910 defined by first implant body 1812, or a portion thereof, can be countersunk or counterbored to allow a fastener to sit flush with, or below, the outer surface of first implant 1802. Thus, a first fastener is disposed through a first passageway defined by first implant body 1812 and a second fastener is disposed through a second passageway defined by first implant body 1812. A fastener can be disposed through each passageway defined by a first implant body.

In the illustrated embodiment, each passageway 1910 defined by first implant body 1812 has a passageway axis that extends through its center and each passageway 1889 defined by second implant body 1834 has a passageway axis that extends through its center. Each passageway axis of each passageway 1910 defined by first implant body 1812 is disposed on a first plane and each passageway axis of each passageway 1889 defined by second implant body 1834 is disposed on a second plane that intersects the first plane at an angle. The first plane and second plane can intersect at any suitable angle, and skilled artisans will be able to select a suitable angle for a first plane and a second plane to intersect according to a particular embodiment based on various considerations, including the structural arrangement at a treatment site. Example angles considered suitable for a first plane and a second plane to intersect include, but are not limited to, an angle between about 1 degree and 90 degrees, an angle between about 90 degrees and about 180 degrees, a 90 degree angle, a substantially 90 degree angle, a 45 degree angle, a substantially 45 degree angle, an acute angle, an obtuse angle, and any other angle considered suitable for a particular application. Alternatively, a first plane that contains each passageway axis of each passageway defined by a first implant component can extend parallel, or substantially parallel, to a second plane that contains each passageway axis of each passageway defined by a second implant component.

While a plurality of first implant protuberances 1904 have been illustrated and described, the body of an implant component can define any suitable number of protuberances, and skilled artisans will be able to select a suitable number of protuberances for inclusion in an implant component according to a particular embodiment based on various considerations, including the structural configuration at an implant site. Example number of protuberances considered suitable include to include in an implant component include, but are not limited to, one, at least one, two, three, four, a plurality, and any other number considered suitable for a particular application.

While second implant component 1804 is shown as including a plurality of second implant projections 1836, a second implant component can omit the inclusion of a plurality of second implant projections. Alternatively, in addition to second implant 1804 including a plurality of second implant projections 1836, a first implant can include a plurality of first implant projections.

FIGS. 54, 55, 56, and 57 illustrate a thirteenth exemplary surgical implant system 2000. The implant system 2000 is similar to implant system 800 illustrated in FIGS. 26, 27, 28, and 29, and described above, except as detailed below. Reference numbers in FIGS. 54, 55, 56, and 57 refer to the same structural element or feature referenced by the same number in FIGS. 26, 27, 28, and 29, offset by 1200. Thus, implant system 2000 comprises a first implant component 2002, a second implant component 2004, and an insert 2006.

In the illustrated embodiment, alternative to including a plurality of bores that extend through the second implant proximal end and through the second implant surface, second implant body 2034 defines a plurality of second implant protuberances 2086. Each protuberance of the plurality of second implant protuberances 2086 extends outward and away from the second implant surface 2038 from a protuberance first end 2087 toward second implant distal end 2032 to a protuberance second end 2088 at an acute, or substantially acute, angle with respect to second implant surface 2038. The second implant body 2034 defines a passageway 2089 through each protuberance of the plurality of second implant protuberances 2086 and that extends from a first opening defined on the second implant proximal end 2030 to a second opening defined on the protuberance second end 2088. Each passageway 2089 provides access for passing a fastener of the plurality of fasteners 2078 through a protuberance of the plurality of protuberances 2086 to attach, or assist with attaching, second implant component 2004 at an implant site. Thus, a first fastener is disposed through a first passageway defined by second implant body 2034 and a second fastener is disposed through a second passageway defined by second implant body 2034. A fastener can be disposed through each passageway defined by a second implant body.

In the illustrated embodiment, alternative to first implant body defining a plurality of bores that extend through the first implant proximal end and through the first implant surface, first implant body 2012 defines a plurality of first implant protuberances 2104. Each protuberance of the plurality of first implant protuberances 2104 extends outward and away from the first implant surface 2016 from a protuberance first end 2106 toward first implant distal end 2010 to a protuberance second end 2108 at an acute, or substantially acute, angle with respect to first implant surface 2016. The first implant body 2012 defines a passageway 2110 through each protuberance of the plurality of first implant protuberances 2104 and that extends from a first opening defined on the first implant proximal end 2008 to a second opening defined on the protuberance second end 2108. Each passageway 2110 provides access for passing a fastener of the plurality of fasteners 2078 through a protuberance of the plurality of protuberances 2104 to attach, or assist with attaching, first implant component 2002 at an implant site. Optionally, each passageway 2089 defined by second implant body 2034, or a portion thereof, can be countersunk or counterbored to allow a fastener to sit flush with, or below, the outer surface of second implant 2004 and each passageway 2110 defined by first implant body 2012, or a portion thereof, can be countersunk or counterbored to allow a fastener to sit flush with, or below, the outer surface of first implant 2002. Thus, a first fastener is disposed through a first passageway defined by first implant body 2012 and a second fastener is disposed through a second passageway defined by first implant body 2012. A fastener can be disposed through each passageway defined by a first implant body.

In the illustrated embodiment, each passageway 2110 defined by first implant body 2012 has a passageway axis that extends through its center and each passageway 2089 defined by second implant body 2034 has a passageway axis that extends through its center. Each passageway axis of each passageway 2110 defined by first implant body 2012 is disposed on a first plane and each passageway axis of each passageway 2089 defined by second implant body 2034 is disposed on a second plane that intersects the first plane at an angle. The first plane and second plane can intersect at any suitable angle, and skilled artisans will be able to select a suitable angle for a first plane and a second plane to intersect according to a particular embodiment based on various considerations, including the structural arrangement at a treatment site. Example angles considered suitable for a first plane and a second plane to intersect include, but are not limited to, an angle between about 1 degree and 90 degrees, an angle between about 90 degrees and about 180 degrees, a 90 degree angle, a substantially 90 degree angle, a 45 degree angle, a substantially 45 degree angle, an acute angle, an obtuse angle, and any other angle considered suitable for a particular application. Alternatively, a first plane that contains each passageway axis of each passageway defined by a first implant component can extend parallel, or substantially parallel, to a second plane that contains each passageway axis of each passageway defined by a second implant component.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:
1. A system for use in a joint arthroplasty, the system comprising:
 a first implant component comprising a first implant proximal end, a first implant distal end, and a first implant body, the first implant body defining a first implant surface, the first implant surface being convex, the first implant body further defining a first articulating surface opposably facing the first implant surface, the first articulating surface being concave;

a second implant component comprising a second implant proximal end, a second implant distal end having a curvature matching the second implant proximal end, a second implant body defining a second implant surface, the second implant surface being concave, the second implant body further defining a second insert surface opposably facing the second implant surface, the second insert surface being convex, and a recess structure including a pair of recess sidewalls extending along edges of the second insert surface from the second implant proximal end to the second implant distal end, and a recess wall extending between the recess sidewalls along the second implant distal end, each recess sidewall defining a groove; and an insert comprising an insert base surface and an insert shoulder having a pair of shoulder walls configured to be releasably received by the pair of recess sidewalls to attach the insert to the second implant component, the insert base surface being concave, and an insert articulating portion comprising an insert articulating surface configured to articulate with the first articulating surface, the insert articulating surface being convex.

2. The system of claim 1, wherein at least one recess sidewall includes a recess first portion extending away from the insert base surface and a recess second portion extending away from the recess first portion, the recess first portion defines a recess first portion width, the recess second portion defines a recess second portion width, and the recess first portion width is different than the recess second portion width.

3. The system of claim 2, wherein the insert defines an insert base width along the insert base, the insert base width being greater than or equal to the recess first portion width.

4. The system of claim 2, wherein the insert articulating portion defines an insert articulating width, the insert articulating width being greater than or equal to the recess second portion width.

5. The system of claim 1, wherein the first implant component further comprises a plurality of first implant projections extending outward and away from the first implant surface from a first implant first projection end to a first implant projection second end for each of the plurality of first implant projections, the plurality of first implant projections configured to increase the amount of attachment between the first implant component and a first implant site.

6. The system of claim 5, wherein each first implant projection second end includes a plurality of first projection declining surfaces, the first projection declining surfaces angled such that a first end of each first projection declining surface is disposed at a first projection distance from the first implant surface and the second end of each first projection declining surface is disposed at a second projection distance from the first implant surface, the first projection distance being greater than the second projection distance.

7. The system of claim 6, wherein the first implant distal end is on a same side of the system as the second implant distal end when the first implant component articulates with the insert and the insert is attached to the second implant component; and wherein each first end of each first projection declining surface is closer to the first implant proximal end than the corresponding second end of each first projection declining surface, and each first end of each second projection declining surface is closer to the second implant proximal end than the corresponding second end of each second projection declining surface.

8. The system of claim 1, wherein the second implant component further comprises a plurality of second implant projections extending outward and away from the second implant surface from a second implant projection first end to a second implant projection second end for each of the plurality of second implant projections, the plurality of first implant projections configured to increase the amount of attachment between the second implant component and a second implant site spaced from the first implant site.

9. The system of claim 8, wherein each second implant projection second end includes a plurality of second projection declining surfaces, the second projection declining surfaces angled such that a first end of each second projection declining surface is disposed at a third projection distance from the second implant surface and the second end of each second projection declining surface is disposed at a fourth projection distance from the second implant surface, the third projection distance being greater than the fourth projection distance.

10. The system of claim 1, wherein the second implant component further comprises a plurality of recess projections extending into the recess structure along a portion of a length of the recess structure, each recess projection having a tapered edge configured to releasably attach the second implant component to the insert.

11. The system of claim 1, wherein the insert shoulder further comprises an insert recess extending into a body of the insert from an insert distal end towards an insert proximal end, the insert shoulder configured to mechanically stop axial movement of the insert when the insert is introduced into the recess structure of the second implant component.

12. The system of claim 1, wherein the first implant surface has a first radius of curvature, the insert articulating surface has a second radius of curvature substantially equal to the first radius of curvature.

13. The system of claim 1, wherein the second insert surface has a third radius of curvature, and the insert base surface has a fourth radius of curvature substantially equal to the third radius of curvature.

* * * * *